(12) United States Patent
Bhat et al.

(10) Patent No.: US 11,059,813 B2
(45) Date of Patent: Jul. 13, 2021

(54) POLYMORPHIC FORMS OF DASATINIB

(71) Applicant: BIOCON LIMITED, Electronic (IN)

(72) Inventors: Ramakrishna Parameshwar Bhat, Uttara Kannada (IN); Jithendrababu Raghunadhachetty, Chittoor District (IN); Raghavendracharyulu Venkata Palle, Hyderabad (IN); Mariappan Kaliappan, Madurai (IN); Reddy VijayBhaskar Regalla, Krishna District (IN)

(73) Assignee: BIOCON LIMITED, Electronic (IN)

( * ) Notice: Subject to any disclaimer, the term of this patent is extended or adjusted under 35 U.S.C. 154(b) by 0 days.

(21) Appl. No.: 16/628,746

(22) PCT Filed: Jul. 7, 2018

(86) PCT No.: PCT/IB2018/055022
§ 371 (c)(1),
(2) Date: Jan. 6, 2020

(87) PCT Pub. No.: WO2019/008555
PCT Pub. Date: Jan. 10, 2019

(65) Prior Publication Data
US 2020/0377495 A1 Dec. 3, 2020

(30) Foreign Application Priority Data

| Jul. 7, 2017 | (IN) | 201741024067 |
| Aug. 24, 2017 | (IN) | 201741029965 |
| Jan. 11, 2018 | (IN) | 201841001249 |
| Feb. 28, 2018 | (IN) | 201841007613 |

(51) Int. Cl.
C07D 417/12 (2006.01)
C07D 417/14 (2006.01)

(52) U.S. Cl.
CPC ........ C07D 417/14 (2013.01); *C07B 2200/13* (2013.01); *C07D 417/12* (2013.01)

(58) Field of Classification Search
CPC .................................................. C07D 417/12
See application file for complete search history.

(56) References Cited

U.S. PATENT DOCUMENTS

| 6,596,746 | B1 | 4/2003 | Hargraves |
| 7,491,725 | B2 | 2/2009 | Lajeunesse et al. |
| 7,973,045 | B2 | 7/2011 | Simo et al. |
| 8,067,423 | B2 | 11/2011 | Simo et al. |
| 2006/0004067 | A1 | 1/2006 | Chen et al. |

FOREIGN PATENT DOCUMENTS

| CN | 102030745 B | 5/2012 |
| WO | 2000062778 A1 | 10/2000 |
| WO | 2007035874 A1 | 3/2007 |
| WO | 2010062715 A3 | 6/2010 |
| WO | 2010067374 A2 | 6/2010 |
| WO | 2013186726 A2 | 12/2013 |
| WO | 2016001025 A1 | 1/2016 |
| WO | 2017002131 A1 | 1/2017 |
| WO | 2017034615 A1 | 3/2017 |
| WO | 2017098391 A1 | 6/2017 |
| WO | 2017134617 A1 | 8/2017 |

OTHER PUBLICATIONS

International Search Report and Written Opinion of WO 2019/008555 A1 (PCT/2018/055022) with a publication date of Jan. 10, 2019.
O. Almarsson, MJ Zaworotko "Crystal engineering of the composition of pharmaceutical phases. Do pharmaceutical co-crystals represent a new path to improved medicines?" Chem Commun 2004,17,pp. 1889-1896.
I. Miroshnyk; Expert Opinion on Drug Delivery, 2009; 6(4): 333-341.

*Primary Examiner* — Emily A Bernhardt
(74) *Attorney, Agent, or Firm* — Katten Muchin Rosenman LLP

(57) ABSTRACT

The present invention provides for the dasatinib-thymine co-crystal and dasatinib-adenine co-crystal. The present invention further provides dasatinib-butanediol solvate. The present invention further provides for crystalline dasatinib-(±)-1, 2-Butanediol, crystalline dasatinib (R)-1, 2-Butanediol, crystalline dasatinib (S)-1, 2-Butanediol and crystalline dasatinib (±)-2, 3-Butanediol and processes for preparation thereof. The present invention also provides for a process for preparation of amorphous dasatinib using dasatinib-butanediol solvate. The present invention further provides for the preparation of anhydrous dasatinib. The present invention also provides for a process for preparation of dasatinib monohydrate from anhydrous dasatinib.

14 Claims, 17 Drawing Sheets

POLYMORPHIC FORMS OF DASATINIB

RELATED APPLICATION

This application is a U.S. National Stage entry of International Application No. PCT/IB2018/055022 filed Jul. 7, 2018, which claims the benefit of IN Patent Application 201841007613, filed Feb. 28, 2018, IN Patent Application 201841001249, filed Jan. 11, 2018, IN Patent Application 201741029965, filed Aug. 24, 2017, and IN Patent Application No. 201741024067, filed Jul. 7, 2017, each of which is herein incorporated by reference in its entirety for all purposes.

TECHNICAL FIELD

The present invention relates to polymorphic forms of dasatinib. In particular, the invention relates to co-crystals and solvates of dasatinib and processes for the preparation thereof.

Formula I

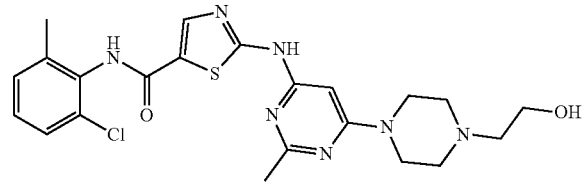

BACKGROUND AND PRIOR ART OF THE DISCLOSURE

SPRYCEL® (Dasatinib monohydrate) is a kinase inhibitor. The chemical name for Dasatinib monohydrate is N-(2-chloro-6-methylphenyl)-2-[[6-[4-(2-hydroxyethyl)-1-piperazinyl]-2-methyl-4-pyrimidinyl] amino]-thiazolecarboxamide, monohydrate which is having molecular Formula $C_{22}H_{26}ClN_7O_2S \cdot H_2O$ and molecular weight 506.02 (monohydrate) and its structural Formula is as follows,

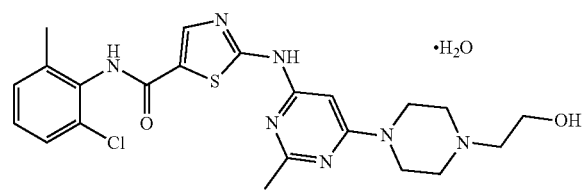 [SMILES: Cc1nc(Nc2ncc(C(=O)Nc3c(C)cccc3Cl)s2)cc(N2CCN(CCO)CC2)n1 ; O]

SPRYCEL® is a kinase inhibitor indicated for the treatment of newly diagnosed adults with Philadelphia chromosome-positive (Ph+) chronic myeloid leukemia (CML) in chronic phase, adults with chronic, accelerated or myeloid or lymphoid blast phase Ph+ CML with resistance or intolerance to prior therapy including imatinib and adults with Philadelphia chromosome-positive acute lymphoblastic leukemia (Ph+ ALL) with resistance or intolerance to prior therapy.

Dasatinib which was disclosed in PCT Publication No. WO 00/62778 and in U.S. Pat. No. 6,596,746. Dasatinib, chemically N-(2-chloro-6-methylphenyl)-2-[[6-[4-(2-hydroxyethyl)-1-piperazinyl]-2-methyl-4-pyrimidinyl] amino]-5-thiazole carboxamide.

Dasatinib is known to exist in various solid-state forms: a monohydrate, four anhydrous and unsolvated forms that are described in U.S. Pat. No. 7,491,725 B2, US2006/0004067A1, U.S. Pat. No. 7,973,045 B2 and WO2010/067374 and therein referred to as forms N-6, T1H1-7, B and I.

U.S. Pat. No. 8,067,423 B2 discloses an amorphous form and solvates of IPA, THF, 2-MeTHF, 1,4-Dioxane, Pyridine, Toluene, MIBK, Mono acetone, 2-Butanol-DMSO, IPA-DMF, n-Propanol-DMF, n-Propanol, 2-Butanol-DMF, 2-Butanol, n-Butanol-DMSO, DMF-water, DMF, MIPK, Dimethoxy ethane, Cellosolve, Methyl acetate, Methanol, Ethyl acetate, 2-Pentanone, Dimethyl carbonate, Isopropyl acetate, Dichloromethane, Methyl formate, t-Butanol, MEK, Monochloro benzene, PGME, Cyclopentyl methyl ether, MTBE, Amyl alcohol, Dimethyl carbonate, Ethylene glycol and glycerol.

PCT publication WO2007/035874 A1 discloses crystalline form of a mono-hydrochloric acid salt of Dasatinib comprising Form CA-2, second crystalline form of a mono-hydrochloric acid salt of Dasatinib comprising Form HAC2-1, crystalline form of a di-hydrochloric acid salt of Dasatinib comprising Form H3-1, crystalline form of a monosulfuric acid salt of Dasatinib comprising Form SB-2, second crystalline form of a monosulfuric acid salt of Dasatinib comprising Form SD-2, crystalline form of a hemisulfuric acid salt of Dasatinib comprising Form SA-I, second crystalline form of a hemisulfuric acid salt of Dasatinib comprising Form SC-I, crystalline form of an acetic acid salt of Dasatinib comprising Form NMP-I, a crystalline form of a phosphoric acid salt of Dasatinib comprising Form SA-I, a crystalline form of a hydrobromic acid salt of Dasatinib comprising Form H1.5-1, a crystalline form of a fumaric acid salt of Dasatinib comprising Form TO-I, a crystalline form of a salicylic acid salt of Dasatinib comprising Form SS-2, a crystalline form of a tartaric acid salt of Dasatinib, a crystalline form of a methanesulfonic acid salt of Dasatinib comprising Form PG-I, a crystalline form of a maleic acid salt of Dasatinib comprising Form E-1, a crystalline form of a maleic acid salt of Dasatinib comprising Form H3-2 and a crystalline form of a p-toluenesulfonic acid salt of Dasatinib comprising Form N-1.

Chinese patent CN102030745 discloses a crystalline solvate YE of Dasatinib and isopropyl ether.

Furthermore, Dasatinib solvates are known from US2006/0004067A, WO2010/062715, and in particular, patent application WO 2010/062715 includes the solvates of isosorbide dimethyl ether, N,N'-dimethylethylene urea and N,N'-dimethyl-N,N'-propylene urea. Isosorbide dimethyl ether is used in cosmetic and pharmaceutical Formulations.

PCT publication WO2013/186726 A2 discloses various co-crystals with Dasatinib such as Dasatinib-Methyl-4-hydroxy-benzoate co-crystal (3:1), Dasatinib-Nicotinamide co-crystal (3:1), Dasatinib-Ethyl gallate co-crystal (3:1), Dasatinib-Vanillin co-crystal (3:1), Dasatinib-Methyl gallate co-crystal (3:1) and Dasatinib-(1R,2S,5R)-(−)-Menthol co-crystal (3:1).

This invention as disclosed in WO2013/186726 A2 suffers from following disadvantages.

Dasatinib and co-former molar ratio in co-crystal is the same as the molar ratio of input.

The volume of the solvent used is huge (>75 vol) which may not be suitable for the scale up.

The isolation procedure involves the complete evaporation of the reaction mass under dry nitrogen flow, which may not be suitable for scale up.

The input for the formation of Dasatinib co-crystals is Dasatinib monohydrate. PCT publication WO2016/001025 A1 discloses various co-crystals such as Dasatinib-(1R,2S,5R)-(−)-Menthol co-crystal (2:1) and Dasatinib-Vanillin co-crystal (1:1).

This invention as disclosed in WO2016/001025 A1 suffers from following disadvantages.

The process for the preparation of Dasatinib-(1R,2S,5R)-(−)-Menthol co-crystal (2:1) involves heating to 120° C. under neat condition which may not be suitable for scale up.

The process for the preparation of Dasatinib-(1R,2S,5R)-(−)-Menthol co-crystal (2:1) involves filtration at 90° C. which may not be suitable for scale up.

The process for the preparation of Dasatinib-Vanillin co-crystal (1:1) involves heating to 120° C. under neat condition, which may not be suitable for scale up.

The input for the formation of Dasatinib co-crystals is Dasatinib monohydrate.

PCT publication WO2017/002131 A1 discloses Dasatinib-1,2-Propanediol solvate and process for the preparation of Dasatinib-1,2-Propanediol solvate.

This invention as disclosed in WO2017/002131 A1 suffers from following disadvantages.

Solvent required to prepare and get Dasatinib-1,2-Propanediol solvate is huge as around 21 volume of solvent is used.

Process involves wet solid isolation followed by 40 volume of solvent usage to get the pure solvate, which means an impure wet solid is used.

PCT Publication WO 20171/034615 A1 also discloses Dasatinib-1,2-Propanediol solvate and process for the preparation of Dasatinib-1,2-Propanediol solvate.

Dasatinib-1,2-Propanediol solvate formation requires 12 volumes of solvent, which again is not economical.

BHT is used in the solvate formation to prevent the formation of N-oxide related impurities.

SUMMARY OF THE INVENTION

Aspects of the present application provides co-crystals and solvates of dasatinib and safe, simpler & economical processes for the preparation thereof. Each step of the process disclosed herein are contemplated both in the context of the multistep sequences described and individually.

First aspect of the present invention is crystalline Dasatinib-Thymine co-crystal of Formula Ia.

Second aspect of the present invention, the crystalline Dasatinib-Thymine co-crystal of Formula Ia is characterized by $^1$H NMR which is in accordance with the FIG. 1.

Third aspect of the present invention, the crystalline Dasatinib-Thymine co-crystal of Formula Ia is further characterised by DSC having endotherm at around 260° C. and the DSC pattern in accordance with the FIG. 2.

Fourth aspect of the present invention, the crystalline Dasatinib-Thymine co-crystal of Formula Ia is further characterised by PXRD having the main 2-theta values 6.83±0.2, 7.15±0.2, 12.15±0.2, 13.27±0.2, 13.64±0.2, 14.29±0.2, 16.31±0.2, 16.67±0.2, 17.30±0.2, 18.32±0.2, 18.78±0.2, 19.18±0.2, 20.56±0.2, 21.42±0.2, 21.90±0.2, 22.40±0.2, 23.94±0.2, 24.39±0.2, 26.76±0.2, 27.37±0.2, 27.70±0.2, 28.77±0.2, 29.28±0.2, 30.21±0.2, 31.39±0.2, 34.32±0.2, 36.14±0.2, 43.75±0.2 and the PXRD pattern in accordance with the FIG. 3.

TABLE 1

| Num. | Gonio | d | Int | I/Imax |
|---|---|---|---|---|
| 1 | 6.8396 | 12.9133 | 495 | 22.1 |
| 2 | 7.1567 | 12.342 | 2245 | 100.0 |
| 3 | 12.1553 | 7.27546 | 124 | 5.5 |
| 4 | 13.2770 | 6.66323 | 250 | 11.2 |
| 5 | 13.6481 | 6.48289 | 203 | 9.0 |
| 6 | 14.2953 | 6.19078 | 516 | 23.0 |
| 7 | 16.3106 | 5.43014 | 90 | 4.0 |
| 8 | 16.6718 | 5.3133 | 158 | 7.1 |
| 9 | 17.3082 | 5.11933 | 37 | 1.6 |
| 10 | 18.3283 | 4.83664 | 58 | 2.6 |
| 11 | 18.7851 | 4.72004 | 42 | 1.9 |
| 12 | 19.1824 | 4.62317 | 70 | 3.1 |
| 13 | 20.5697 | 4.3144 | 61 | 2.7 |
| 14 | 21.4246 | 4.14412 | 66 | 3.0 |
| 15 | 21.9015 | 4.05495 | 108 | 4.8 |
| 16 | 22.4019 | 3.96549 | 41 | 1.8 |
| 17 | 23.9490 | 3.71272 | 91 | 4.0 |
| 18 | 24.3900 | 3.64658 | 78 | 3.5 |
| 19 | 26.7672 | 3.32787 | 38 | 1.7 |
| 20 | 27.3775 | 3.25506 | 112 | 5.0 |
| 21 | 27.7041 | 3.21742 | 67 | 3.0 |
| 22 | 28.7768 | 3.09988 | 40 | 1.8 |
| 23 | 29.2859 | 3.04713 | 36 | 1.6 |
| 24 | 30.2100 | 2.956 | 64 | 2.9 |
| 25 | 31.3934 | 2.84722 | 36 | 1.6 |
| 26 | 34.3268 | 2.61032 | 32 | 1.4 |
| 27 | 36.1430 | 2.48321 | 26 | 1.2 |
| 28 | 43.7583 | 2.06708 | 28 | 1.2 |

Fifth aspect of the present invention provides the process for the preparation of crystalline Dasatinib-Thymine co-crystal of Formula Ia.

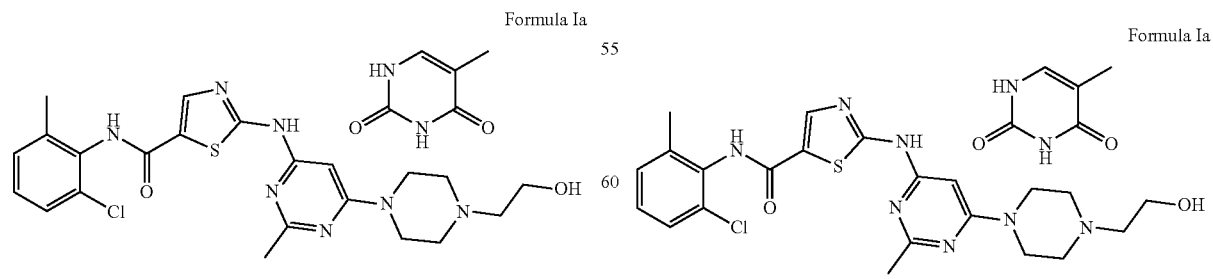

Formula Ia wherein the process does not involve the isolation of Dasatinib as intermediate.

Sixth aspect of the present invention provides the process for the preparation of crystalline Dasatinib-Thymine co-crystal of Formula Ia.

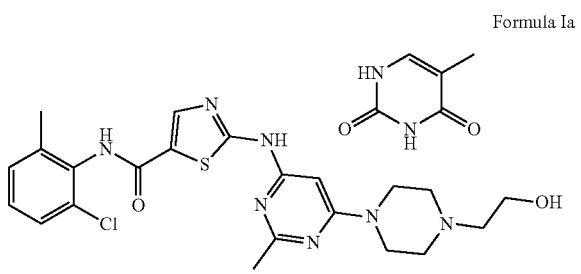

Formula Ia comprising the following steps,
Treating the Dichloro intermediate of Formula II

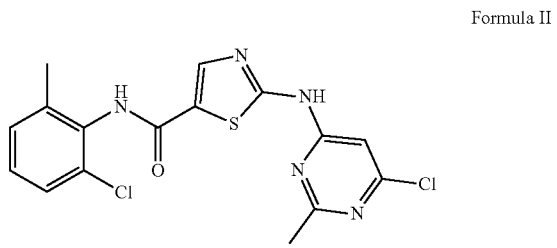

Formula II with 2-(piperazin-1-yl)ethan-1-ol of Formula III

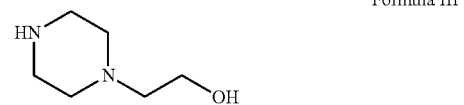

Formula III in a suitable organic solvent at a suitable temperature to obtain Formula I in situ

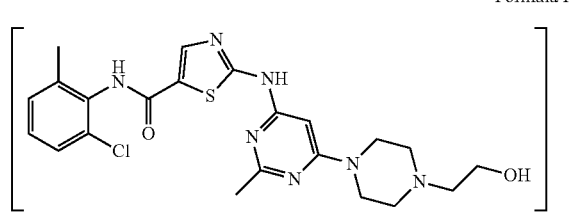

Formula I treating with Thymine in a suitable solvent/s at a suitable temperature,

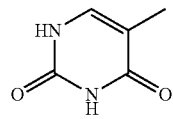

to obtain crystalline Dasatinib-Thymine co-crystal of Formula Ia.

Further, the present invention relates to the process for the preparation for crystalline Dasatinib-Thymine co-crystal of Formula Ia comprising following steps,
a) Charging Dichloro intermediate of Formula II into a reactor
b) Adding 2-(piperazin-1-yl) ethan-1-ol of Formula III
c) Adding a suitable organic solvent
d) Heating the reaction mass to a suitable temperature
e) Maintaining the reaction mass at a suitable temperature
f) Cooling the reaction mass to a suitable temperature
g) Adding Thymine at a suitable temperature
h) Adding a suitable organic solvent to the reaction mass at a suitable temperature
i) Heating the reaction mixture to a suitable temperature
j) Maintaining the reaction mixture at a suitable temperature
k) Cooling the reaction mixture to a suitable temperature
l) Stirring the reaction mixture at a suitable temperature
m) Adding water to the reaction mixture at a suitable temperature
n) Stirring the reaction mixture at a suitable temperature
o) Filtering the reaction mixture under vacuum
p) Washing the solid with a suitable organic solvent
q) Suck drying the wet solid under vacuum
r) Drying the wet solid at a suitable temperature under vacuum to obtain crystalline Dasatinib-Thymine co-crystal of Formula Ia.

Further, according to step c), as described above, a suitable organic solvent is selected from the group consisting of solvents selected from N,N-Dimethylacetamide, N,N-Dimethylformamide and the like.

Further, according to step d) and step e), suitable temperature is selected from the range consisting of 40 to 80° C., preferably 70 to 8° C.

Further, in step f), step g) and step h), a suitable temperature is selected from the range consisting of 20 to 60° C., preferably 20 to 40° C., more preferably 20 to 30° C.

Further, in step i) and step j), a suitable temperature is selected from the range consisting of 30 to 62° C., preferably 50 to 62° C.

Further, in step k), step l), step m) and step n), a suitable temperature is selected from the range consisting of 10 to 40° C., preferably 10 to 30° C., more preferably 20 to 30° C.

Further, in step h) and step p), a suitable organic solvent is selected from the group consisting of Alcoholic solvents selected from methanol, ethanol, propanol, n-butanol & isopropanol.

Further, in step r), a suitable temperature is selected from the range consisting of 30 to 65° C., preferably 45 to 65° C., more preferably 50 to 60° C.

Seventh aspect of the present invention provides the process for the preparation of crystalline Dasatinib-Thymine co-crystal of Formula Ia.

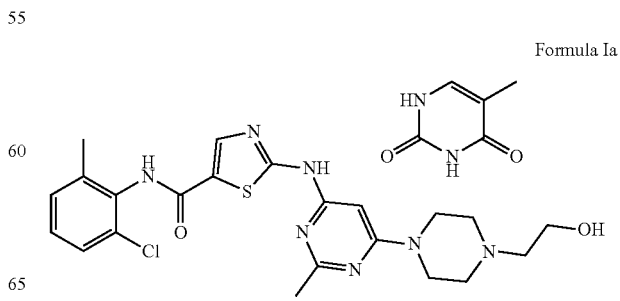

Formula Ia comprising the following steps,
Treating the Dichloro intermediate of Formula II

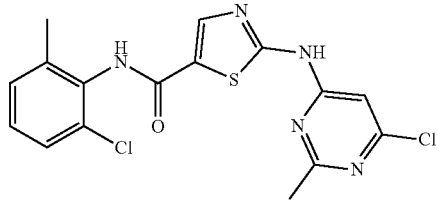
Formula II with 2-(piperazin-1-yl)ethan-1-ol of Formula III

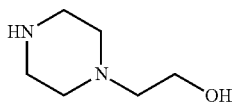
Formula III in a suitable organic solvent at a suitable temperature and isolating Formula I as a wet solid using a suitable organic solvent at a suitable temperature.

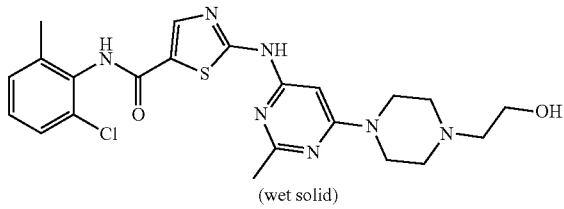
Formula I (wet solid)

Treating the wet solid of Formula I with Thymine

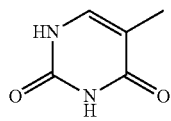

In a suitable solvent/s at a suitable temperature, to obtain crystalline Dasatinib-Thymine co-crystal of Formula Ia,

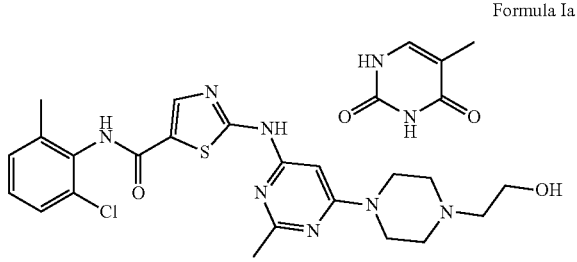
Formula Ia

Eighth aspect of the present invention relates to the alternate process for the preparation of a crystalline Dasatinib-Thymine co-crystal of Formula Ia, comprising the following steps, Treating the Dichloro intermediate of Formula I

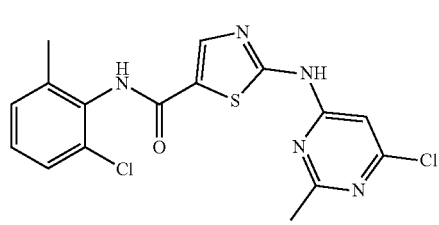
Formula II

S with 2-(piperazin-1-yl)ethan-1-ol of Formula III

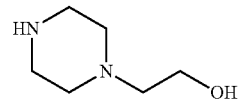
Formula III and Thymine,

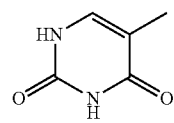

in a suitable solvent at a suitable temperature, to obtain a crystalline Dasatinib-Thymine co-crystal of Formula n,

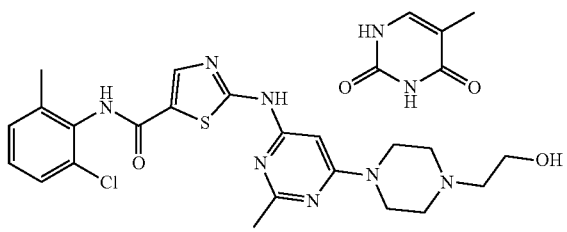
Formula Ia

Further, the present invention relates to the alternate process for the preparation of crystalline Dasatinib-Thymine co-crystal of Formula I, comprising the following steps,
a) charging Dichloro intermediate of Formula II into a reactor
b) adding 2-(piperazin-1-yl)ethan-1-ol of Formula III
c) adding Thymine at a suitable temperature
d) adding a suitable organic solvent
e) heating the reaction mass to a suitable temperature
f) maintaining the reaction mass at a suitable temperature
g) adding a suitable organic solvent at a suitable temperature
h) maintaining the reaction mass at a suitable temperature
i) cooling the reaction mass to a suitable temperature
j) stirring the reaction mixture at a suitable temperature
k) filtering the reaction mixture under vacuum
l) washing the solid with a suitable organic solvent
m) suck drying the wet solid under vacuum
n) drying the wet solid at a suitable temperature under vacuum to obtain a crystalline Dasatinib-Thymine co-crystal of Formula Ia Further, in step d), step g) and step l), a suitable organic solvent is selected from the group consisting of alcoholic solvents, preferably Methanol.

Further, in step e), step f), step g) and step h), a suitable temperature is selected from the range consisting of 30 to 69° C., preferably 50 to 69° C., more preferably 65 to 69° C.

Further, in step i) and step j), a suitable temperature is selected from the range consisting of 10 to 40° C., preferably 10 to 30° C., more preferably 20 to 30° C.

Further, in step n), a suitable temperature is selected from the range consisting of 30 to 65° C., preferably 45 to 65° C., more preferably 50 to 60° C.

Ninth aspect of the present invention is crystalline Dasatinib-Adenine co-crystal of Formula Ib.

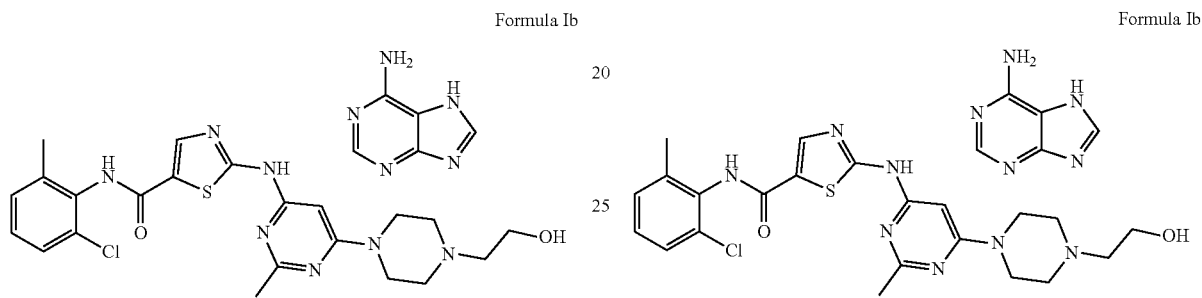

Formula Ib

Tenth aspect of the present invention, the crystalline Dasatinib-Adenine co-crystal of Formula Ib is characterized by $^1$H NMR which is in accordance with the FIG. 4.

Eleventh aspect of the present invention, the crystalline Dasatinib-Adenine co-crystal of Formula Ib is further characterized by DSC having endotherm at around 274.4° C. and the DSC pattern in accordance with the FIG. 5.

Twelfth aspect of the present invention, the crystalline Dasatinib-Adenine co-crystal of Formula Ib is further characterized by PXRD having the main 2-theta values 6.91±0.2, 7.25±0.2, 12.37±0.2, 13.25±0.2, 13.78±0.2, 14.47±0.2, 15.99±0.2, 16.57±0.2, 16.74±0.2, 17.21±0.2, 18.53±0.2, 19.25±0.2, 20.99±0.2, 21.89±0.2, 22.07±0.2, 22.51±0.2, 23.12±0.2, 23.82±0.2, 24.31±0.2, 24.82±0.2, 25.29±0.2, 27.99±0.2, 32.22±0.2, 38.72±0.2. and the PXRD pattern in accordance with the FIG. 6.

TABLE 2

| Num | Gonio | d | Int | T/Imax |
|---|---|---|---|---|
| 1 | 6.9166 | 12.7698 | 1256 | 100.0 |
| 2 | 7.2536 | 12.1773 | 241 | 19.2 |
| 3 | 12.3736 | 7.14762 | 141 | 11.3 |
| 4 | 13.2538 | 6.67486 | 411 | 32.7 |
| 5 | 13.7862 | 6.41824 | 521 | 41.5 |
| 6 | 14.4786 | 6.11283 | 165 | 13.1 |
| 7 | 15.9937 | 5.53701 | 338 | 26.9 |
| 8 | 16.5710 | 5.34538 | 114 | 9.1 |
| 9 | 16.7485 | 5.28913 | 135 | 10.7 |
| 10 | 17.2129 | 5.14746 | 66 | 5.2 |
| 11 | 18.5321 | 4.7839 | 77 | 6.1 |
| 12 | 19.2549 | 4.60592 | 68 | 5.4 |
| 13 | 20.9917 | 4.22859 | 48 | 3.8 |
| 14 | 21.8952 | 4.05611 | 89 | 7.1 |
| 15 | 22.0765 | 4.02321 | 104 | 8.3 |
| 16 | 22.5182 | 3.94528 | 46 | 3.7 |
| 17 | 23.1230 | 3.84344 | 52 | 4.1 |
| 18 | 23.8207 | 3.73241 | 63 | 5.0 |
| 19 | 24.3132 | 3.65791 | 81 | 6.4 |
| 20 | 24.8265 | 3.58343 | 70 | 5.6 |

TABLE 2-continued

| Num | Gonio | d | Int | T/Imax |
|---|---|---|---|---|
| 21 | 25.2906 | 3.51872 | 50 | 4.0 |
| 22 | 27.9983 | 3.18427 | 166 | 13.2 |
| 23 | 32.2280 | 2.77536 | 34 | 2.7 |
| 24 | 38.7229 | 2.3235 | 29 | 2.3 |

Thirteenth aspect of the present invention provides the process for the preparation of crystalline Dasatinib-Adenine co-crystal of Formula Ib.

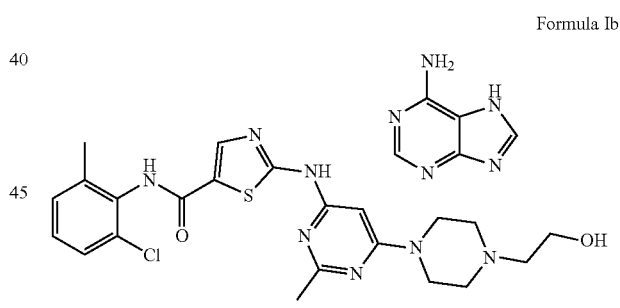

Formula Ib wherein the process does not involve the isolation of Dasatinib.

Fourteenth aspect of the present invention provides the process for the preparation of crystalline Dasatinib-Adenine co-crystal of Formula Ib.

Formula Ib

Comprising the following steps,

Treating the Dichloro intermediate of Formula II

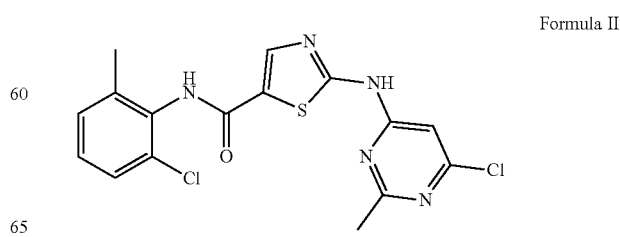

Formula II with 2-(piperazin-1-yl)ethan-1-ol of Formula III

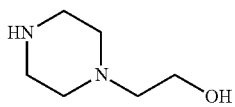

Formula III in a suitable organic solvent at a suitable temperature to obtain Formula I in situ

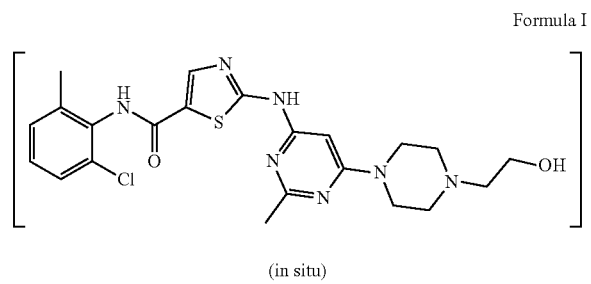

Formula I (in situ)

Treating the with Adenine

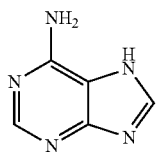

In a suitable solvent/s at a suitable temperature, to obtain crystalline Dasatinib-Adenine co-crystal of Formula Ib,

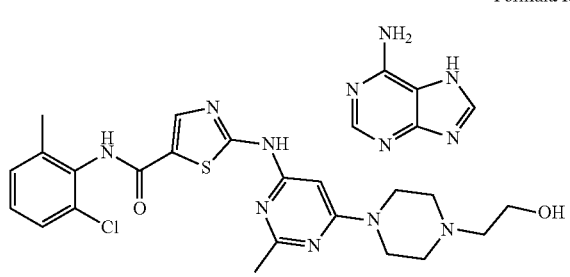

Formula Ib

Further, the present invention relates to the process for the preparation for crystalline Dasatinib-Adenine co-crystal of Formula Ib comprising following steps,
a) Charging Dichloro intermediate of Formula II into a reactor
b) Adding 2-(piperazin-1-yl) ethan-1-ol of Formula III
c) Adding a suitable organic solvent
d) Heating the reaction mass to a suitable temperature
e) Maintaining the reaction mass at a suitable temperature
f) Cooling the reaction mass to a suitable temperature
g) Adding Adenine at a suitable temperature
h) Adding a suitable organic solvent to the reaction mass at a suitable temperature
i) Heating the reaction mixture to a suitable temperature
j) Maintaining the reaction mixture at a suitable temperature k) Cooling the reaction mixture to a suitable temperature
l) Stirring the reaction mixture at a suitable temperature
m) Adding water to the reaction mixture at a suitable temperature
n) Stirring the reaction mixture at a suitable temperature
o) Filtering the reaction mixture under vacuum
p) Washing the solid with a suitable organic solvent
q) Suck drying the wet solid under vacuum
r) Drying the wet solid at a suitable temperature under vacuum to obtain crystalline Dasatinib-Adenine co-crystal of Formula Ib.

Further, according to step c), as described above, a suitable organic solvent is selected from the group consisting of solvents selected from N,N-Dimethylacetamide, N,N-Dimethylformamide and the like.

Further, according to step d) and step e), suitable temperature is selected from the range consisting of 40 to 80° C., preferably 70 to 80° C.

Further, in step f), step g) and step h), a suitable temperature is selected from the range consisting of 20 to 60° C., preferably 20 to 40° C., more preferably 20 to 30° C.

Further, in step i) and step j), a suitable temperature is selected from the range consisting of 30 to 62° C., preferably 50 to 62° C.

Further, in step k), step l), step m) and step n), a suitable temperature is selected from the range consisting of 10 to 40° C., preferably, 10 to 30° C., more preferably 20 to 30° C.

Further, in step h) and step p), a suitable organic solvent is selected from the group consisting of Alcoholic solvents selected from methanol, ethanol, propanol, n-butanol & isopropanol.

Further, in step r), a suitable temperature is selected from the range consisting of 30 to 65° C., preferably 45 to 65° C., more preferably 50 to 60° C.

Fifteenth aspect of the present invention relates to the alternate process for the preparation of a crystalline Dasatinib-Adenine co-crystal Formula Ib, comprising the following steps, Treating the Dichloro intermediate of Formula II

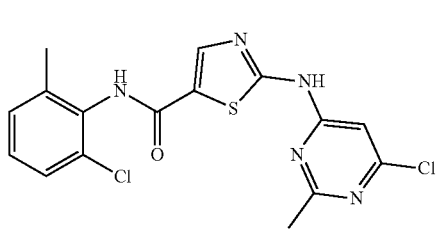

Formula II with 2-(piperazin-1-yl)ethan-1-ol of Formula III

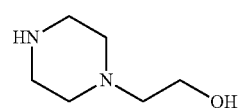

Formula III in a suitable organic solvent at a suitable temperature to obtain Formula I (wet)

Formula I

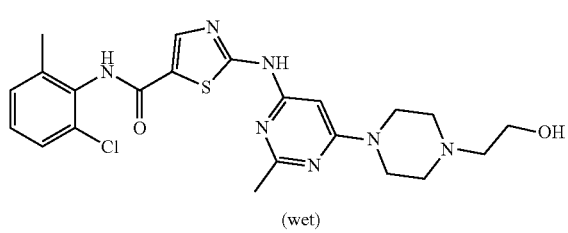

(wet)

treating the wet Formula I with Adenine

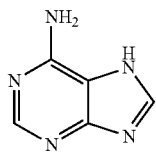

in a suitable solvent/s at suitable temperature, to obtain crystalline Dasatinib-Adenine co-crystal of Formula Ib, Formula Ib

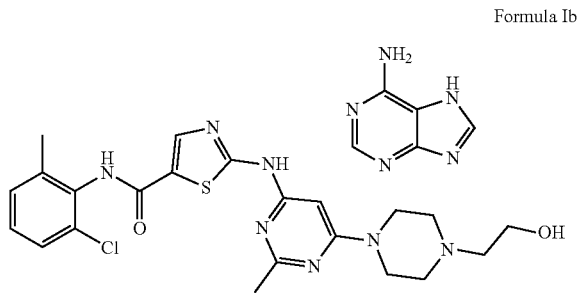

Further, the present invention relates to the alternate process for the preparation of a crystalline Dasatinib-Adenine co-crystal comprising the following steps,
a) charging Dichloro intermediate of Formula I into a reactor
b) adding 2-(piperazin-1-yl)ethan-1-ol of Formula III
c) adding a suitable organic solvent
d) heating the reaction mass to a suitable temperature
e) maintaining the reaction mass at a suitable temperature
f) cooling the reaction mass to a suitable temperature
g) adding a suitable organic solvent at a suitable temperature
h) stirring the reaction mixture at a suitable temperature
i) filtering the reaction mixture under vacuum
j) washing the solid with a suitable organic solvent
k) suck drying the wet solid under vacuum
l) transferring the wet solid into a reactor
m) adding Adenine
n) adding a suitable organic solvent
o) heating the reaction mixture to a suitable temperature
p) maintaining the reaction mixture at a suitable temperature
q) cooling the reaction mixture to a suitable temperature
r) stirring the reaction mixture at a suitable temperature
s) adding water to the reaction mixture at a suitable temperature
t) stirring the reaction mixture at a suitable temperature
u) filtering the reaction mixture under vacuum
v) washing the solid with a suitable organic solvent
w) suck drying the wet solid under vacuum
x) drying the wet solid at a suitable temperature under vacuum to obtain crystalline Dasatinib-Adenine co-crystal of Formula Ib Further, in step c), a suitable organic solvent selected from the group consisting of Amide solvents, preferably N,N-Dimethylacetamide.

Further, in step d) and step e), a suitable temperature selected from the range consisting of 40 to 80° C., preferably 70 to 80° C., more preferably 73 to 77° C.

Further, in step f), step g), step h), step q), step r), step s) and step t) a suitable temperature selected from the range consisting of 20 to 60° C., preferably 20 to 40° C., more preferably 20 to 30° C.

Further, in step o) and step p), a suitable temperature selected from the range consisting of 30 to 62° C., preferably 50 to 62° C., more preferably 58 to 62° C.

Further, in step g), step j), step n) and step v), a suitable organic solvent selected from the group consisting of Alcoholic solvents, preferably Methanol.

Further, in step x), a suitable temperature selected from the range consisting of 30 to 65° C., preferably 45 to 65° C., more preferably 50 to 60° C.

Sixteenth aspect of the present invention relates to the alternate process for the preparation of a crystalline Dasatinib-Adenine co-crystal Formula Ib, comprising the following steps, Treating the Dichloro intermediate of Formula II Formula II

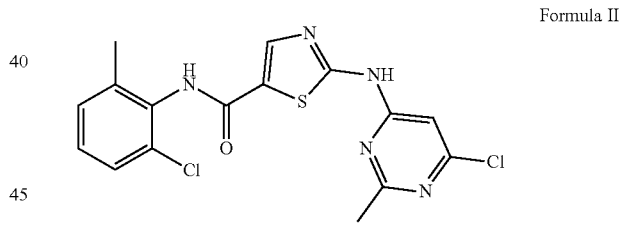

with 2-(piperazin-1-yl)ethan-1-ol of Formula III

Formula III

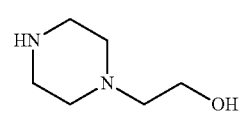

and Adenine,

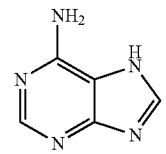

in a suitable solvent at suitable temperature, to obtain crystalline Dasatinib-Adenine co-crystal of Formula Ib, Formula Ib

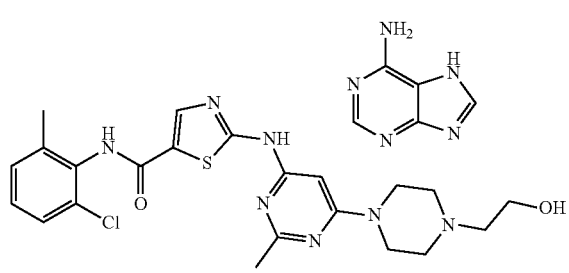

Further, the present invention relates to the alternate process for the preparation of crystalline Dasatinib-Adenine co-crystal of Formula Ib, further comprising the following steps,
a) charging Dichloro intermediate of Formula II into a reactor
b) adding 2-(piperazin-1-yl)ethan-1-ol of Formula III
c) adding Adenine
d) adding a suitable organic solvent
e) heating the reaction mass to a suitable temperature
f) maintaining the reaction mass at a suitable temperature
g) adding a suitable organic solvent at a suitable temperature
h) maintaining the reaction mass at a suitable temperature
i) cooling the reaction mass to a suitable temperature
j) stirring the reaction mixture at a suitable temperature
k) filtering the reaction mixture under vacuum
l) washing the solid with a suitable organic solvent
m) suck drying the wet solid under vacuum
n) drying the wet solid at a suitable temperature under vacuum to obtain crystalline Dasatinib-Adenine co-crystal of Formula Ib Further, in step d), step g) and step l), a suitable organic solvent is selected from the group consisting of alcoholic solvents, preferably Methanol.

Further, in step e), step f), step g) and step h), a suitable temperature is selected from the range consisting of 30 to 62° C., preferably 50 to 62° C., more preferably 58 to 62° C.

Further, in step i) and step j), a suitable temperature is selected from the range consisting of 10 to 40° C., preferably 10 to 30° C., more preferably 20 to 30° C.

Further, in step n), a suitable temperature is selected from the range consisting of 30 to 65° C., preferably 45 to 65° C., more preferably 50 to 60° C.

Seventeenth aspect of the present invention provides Dasatinib-alkanediol solvates.

Eighteenth aspect of the present invention provides crystalline Dasatinib-alkanediol solvate.

Nineteenth aspect of the present invention provides alkanediol solvent chosen from linear alkyl chain having carbon length C4-C7.

Twentieth aspect of the present invention provides alkanediol solvent selected preferably from alkyl chain having carbon length C4-C7 wherein the diols are vicinal.

Twenty first aspect of the present invention provides alkanediol solvent selected preferably from alkyl chain having carbon length C4-C7 wherein, the diols can be racemic and/or absolute stereoisomers.

Twenty second aspect of the present invention provides alkanediol solvent was selected preferably from alkyl chain having carbon length C4-C7 and most preferably, alkyl chain having carbon length C4 wherein, the diols can be racemic and/or absolute stereoisomers.

Twenty third aspect of the present invention provides Dasatinib-butanediol solvate.

Twenty fourth aspect of the present invention provides crystalline Dasatinib-butanediol solvate.

Twenty fifth aspect of the present invention provides a process for the preparation of a crystalline Dasatinib-Butanediol solvate of Formula Ic or Formula Id or Formula Ie or Formula g, comprising the following steps, Treating the Dichloro intermediate of Formula II Formula II

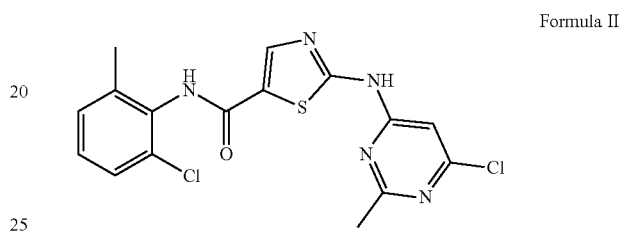

with 2-(piperazin-1-yl)ethan-1-ol of Formula III

Formula III

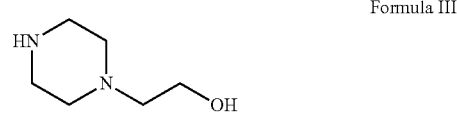

in the presence of a suitable Butanediol and a suitable organic base at suitable temperature, to obtain corresponding a crystalline Dasatinib-Butanediol solvate of Formula Ic or Formula Id or Formula Ie or Formula Ig Formula Ic (or) Id (or) Ie (or) Ig

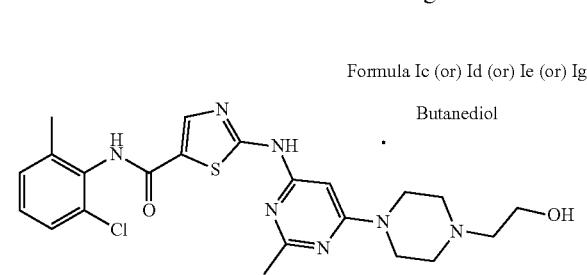

Wherein, Butanediol=(±)-1,2-Butane diol or (R)-1,2-Butanediol or (S)-1,2-Butanediol or (±)-2,3-Butanediol Formula Ic=Dasatinib-(±)-1,2-Butanediol
Formula Id=Dasatinib-(R)-1,2-Butanediol solvate
Formula Ie=Dasatinib-(S)-1,2-Butanediol solvate
Formula Ig=Dasatinib-(±)-2,3-Butanediol solvate Further, the present invention relates to the process for the preparation for crystalline Dasatinib-butane diol solvate of Formula I or Formula Id or Formula Ie or Formula Ig comprising following steps,
a) Charging Dichloro intermediate of Formula II into a reactor
b) Adding 2-(piperazin-1-yl)ethan-1-ol of Formula III
c) Optionally a suitable organic solvent and adding a suitable butanediol
d) Optionally adding a suitable organic base e) Heating the reaction mass to a suitable temperature
f) Maintaining the reaction mass at a suitable temperature
g) Cooling the reaction mass to a suitable temperature
h) Stirring the reaction mixture at a suitable temperature
i) Filtering the reaction mixture under vacuum
j) Suck drying the wet solid under vacuum
k) Optionally washing with wet solid with a suitable organic solvent
l) Optionally drying the wet solid at a suitable temperature under vacuum to obtain corresponding crystalline Dasatinib-butanediol solvate of Formula Ic or Formula Id or Formula Ie or Formula Ig.

Further according to step c), a suitable organic solvent selected from the group consisting of Amide solvents, preferably N,N-Dimethylacetamide.

Further according to step c), the suitable butanediol is selected from the group of vicinal Butanediol, preferably isomer and isomeric mixture of 1,2-butane diols or 2,3-butanediol, more preferably (±)-1,2-butanediol or (R)-1,2-butanediol or (S)-1,2-butanediol or (±)-2,3-butanediol Further according to step e) and step f), a suitable temperature is selected from the range consisting of 90 to 120° C., preferably 100 to 120° C., more preferably 110 to 120° C.

Further according to step g) and step h), a suitable temperature is selected from the range consisting of 30 to 65° C., preferably 50 to 65° C., more preferably 55 to 65° C.

Further according to step k), a suitable organic solvent is selected from the group consisting of Ether solvents, Hydrocarbon solvents preferably, hydrocarbon solvent, more preferably Toluene.

Further according to step l), a suitable temperature is selected from the range consisting of 20 to 45° C., preferably 30 to 45° C., more preferably 35 to 45° C.

Twenty sixth aspect of the present invention provides an alternate process for the preparation of crystalline Dasatinib-Butanediol solvate of Formula Ic or Formula Id or Formula Ie or Formula Ig comprising the following steps, Treating the Dichloro intermediate of Formula II

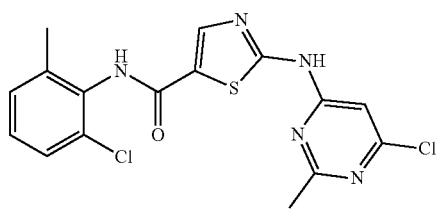

Formula II with 2-(piperazin-1-yl)ethan-1-ol of Formula III

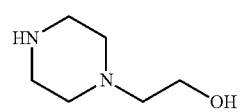

Formula III in the presence of suitable organic solvent and a suitable organic base at a suitable temperature to obtain Formula I (In-situ)

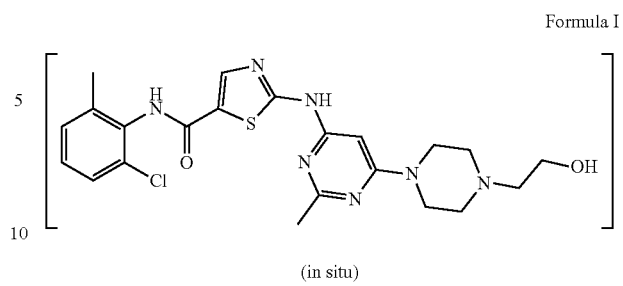

Formula I (in situ)

treating the mass containing the Formula I with a suitable Butanediol at a suitable temperature, to obtain crystalline Dasatinib-Butanediol solvate of Formula Ic or Formula Id or Formula Ie or Formula Ig,

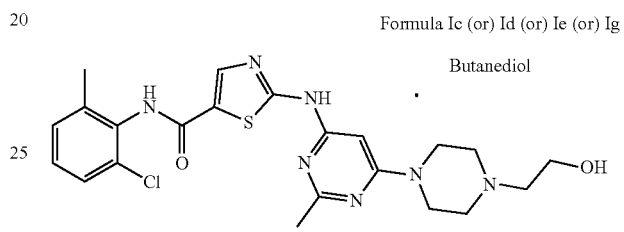

Formula Ic (or) Id (or) Ie (or) Ig

Butanediol

Wherein, Butanediol=(±)-1,2-Butane diol or (R)-1,2-Butanediol or (S)-1,2-Butanediol or (±)-2,3-Butanediol Formula Ic=Dasatinib-(±)-1,2-Butane diol solvate
Formula Id=Dasatinib-(R)-1,2-Butanediol solvate
Formula Ie=Dasatinib-(S)-1,2-Butanediol solvate
Formula Ig=Dasatinib-(±)-2,3-Butane diol solvate Further, the present invention relates to the process for the preparation for crystalline Dasatinib-butane diol solvate of Formula k or Formula Id or Formula Ie or Formula Ig comprising following steps, a) Charging Dichloro intermediate of Formula II into a reactor
b) Adding 2-(piperazin-1-yl)ethan-1-ol of Formula III
c) Adding a suitable organic solvent
d) Optionally addition suitable organic base
e) Heating the reaction mass to a suitable temperature
f) Maintaining the reaction mass at a suitable temperature
g) Adding a suitable Butanediol at a suitable temperature
h) Heating the reaction mass to a suitable temperature
i) Maintaining the reaction mass at a suitable temperature
j) Cooling the reaction mass to a suitable temperature
k) Stirring the reaction mixture at a suitable temperature
l) Filtering the reaction mixture under vacuum
m) Suck drying the wet solid under vacuum
n) Optionally washing with wet solid with as suitable organic solvent
o) Optionally drying the wet solid at a suitable temperature under vacuum to obtain crystalline Dasatinib-Butanediol solvate of Formula Ic or Formula Id or Formula Ie or Formula Ig.

Further according step c), a suitable organic solvent is selected from, Dimethyl sulfoxide, N,N-Dimethyl acetamide, preferably N,N-Dimethyl acetamide Further according to step d), a suitable organic base is selected from the group consisting of tertiary amine, preferably Diisopropylethylamine or Triethylamine, more preferably Triethylamine.

Further according to step e) step f) and step g), a suitable temperature is selected from the range consisting of 30 to 90° C., preferably, 60 to 90° C., more preferably 83 to 87° C.

Further according to step h) and step i), a suitable temperature is selected from the range consisting of 30 to 122° C., preferably, 90 to 122° C., more preferably 118 to 122° C.

Further according to step g), the suitable butanediol is selected from the group of vicinal Butanediol, preferably isomer and isomeric mixture of 1,2-butane diols or 2,3-butanediols, more preferably (=)-1,2-butanediol or (R)-1,2-butanediol or (S)-1,2-butanediol or (±)-2,3-butanediol Further according to step j) and step k), a suitable temperature is selected from the range consisting of 30 to 65° C., preferably 50 to 65° C., more preferably 55 to 65° C.

Further according to step n), a suitable organic solvent is selected from the group consisting of Ether solvents, Hydrocarbon solvents preferably, hydrocarbon solvent, more preferably Toluene.

Further according to step o), a suitable temperature is selected from the range consisting of 20 to 45° C. preferably 30 to 45° C., more preferably 35 to 45° C.

Twenty seventh aspect of the present invention provides the crystalline Dasatinib-(±)-1,2-Butanediol solvate.

Twenty eighth aspect of the present invention, the crystalline crystalline Dasatinib-(±)-1,2-Butanediol solvate of Formula Ic is further characterized by PXRD having the main 2-theta values 5.61±0.2, 8.05±0.2, 10.99±0.2, 11.22±0.2, 12.50±0.2, 13.53±0.2, 14.59±0.2, 14.99±0.2, 16.84±0.2, 17.25±0.2, 17.58±0.2, 18.23±0.2, 19.18±0.2, 19.83±0.2, 20.46±0.2, 21.32±0.2, 21.70±0.2, 22.05±0.2, 22.49±0.2, 23.44±0.2, 24.11±0.2, 24.78±0.2, 25.51±0.2, 26.16±0.2, 27.12±0.2, 27.56±0.2, 30.86±0.2, 32.48±0.2, 32.96±0.2, 35.29±0.2, 37.23±0.2, 39.53±0.2, 43.69±0.2 and the PXRD pattern in accordance with the FIG. 9.

TABLE 3

| Num. | Gonio | d | Int | I/Imax |
|---|---|---|---|---|
| 1 | 5.6129 | 15.7326 | 1968 | 100.0 |
| 2 | 8.0531 | 10.97 | 37 | 1.9 |
| 3 | 10.9986 | 8.03792 | 331 | 16.8 |
| 4 | 11.2278 | 7.87431 | 825 | 41.9 |
| 5 | 12.5005 | 7.07534 | 211 | 10.7 |
| 6 | 13.5312 | 6.5386 | 148 | 7.5 |
| 7 | 14.5921 | 6.06552 | 48 | 2.4 |
| 8 | 14.9888 | 5.90589 | 57 | 2.9 |
| 9 | 16.8432 | 5.2596 | 286 | 14.5 |
| 10 | 17.2507 | 5.13627 | 247 | 12.5 |
| 11 | 17.5868 | 5.03886 | 81 | 4.1 |
| 12 | 18.2315 | 4.8621 | 136 | 6.9 |
| 13 | 19.1891 | 4.62157 | 41 | 2.1 |
| 14 | 19.8307 | 4.47348 | 33 | 1.7 |
| 15 | 20.4695 | 4.33528 | 40 | 2.0 |
| 16 | 21.3272 | 4.16282 | 52 | 2.6 |
| 17 | 21.7065 | 4.09093 | 232 | 11.8 |
| 18 | 22.0552 | 4.02705 | 191 | 9.7 |
| 19 | 22.4974 | 3.94887 | 148 | 7.5 |
| 20 | 23.4493 | 3.79069 | 41 | 2.1 |
| 21 | 24.1118 | 3.68801 | 356 | 18.1 |
| 22 | 24.7884 | 3.58886 | 80 | 4.1 |
| 23 | 25.5180 | 3.48788 | 44 | 2.2 |
| 24 | 26.1639 | 3.40322 | 79 | 4.0 |
| 25 | 27.1239 | 3.28491 | 143 | 7.3 |
| 26 | 27.5627 | 3.2336 | 144 | 7.3 |
| 27 | 30.8607 | 2.89514 | 38 | 2.0 |
| 28 | 32.4825 | 2.7542 | 36 | 1.8 |
| 29 | 32.9697 | 2.7146 | 26 | 1.3 |
| 30 | 35.2984 | 2.54067 | 33 | 1.7 |
| 31 | 37.2388 | 2.41261 | 31 | 1.6 |
| 32 | 39.5349 | 2.27762 | 33 | 1.7 |
| 33 | 43.6962 | 2.06988 | 26 | 1.3 |

Twenty ninth aspect of the present invention, the crystalline crystalline Dasatinib-(±)-1,2-Butanediol solvate of Formula Ic is further characterized by DSC having endotherms at around 169.5 & 285.4° C. and the DSC pattern in accordance with the FIG. 8.

Thirtieth aspect of the present invention provides a process for the preparation of crystalline Dasatinib-(±)-1,2-butanediol solvate of Formula Ie, comprising the following steps, Treating the Dichloro intermediate of Formula II

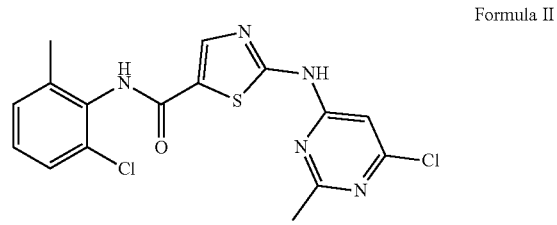 [SMILES: Cc1nc(Cl)cc(Nc2ncc(C(=O)Nc3c(C)cccc3Cl)s2)n1]

Formula II with 2-(piperazin-1-yl)ethan-1-ol of Formula III

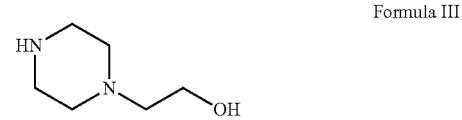

Formula III in the presence of a suitable organic solvent and (=)-1,2-Butanediol and a suitable organic base at a suitable temperature, to obtain corresponding crystalline Dasatinib-(±)-1,2-butanediol solvate of Formula Ic,

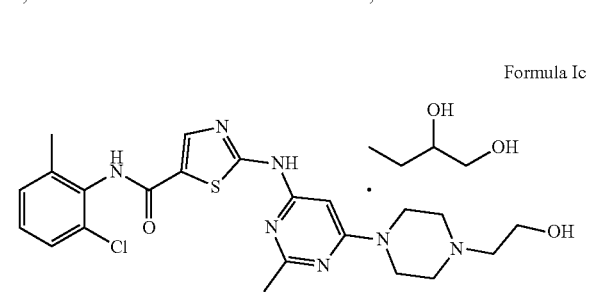

Formula Ic

Further, the present invention relates to the process for the preparation of a crystalline Dasatinib-(±)-1,2-butanediol solvate of Formula Ic, further comprising the following steps, a) charging Dichloro intermediate of Formula II into a reactor
b) adding 2-(piperazin-1-yl)ethan-1-ol of Formula III
c) optionally adding a suitable organic solvent and adding (±)-1,2-butanediol
d) optionally adding a suitable organic base
e) heating the reaction mass to a suitable temperature
f) maintaining the reaction mass at a suitable temperature
g) cooling the reaction mass to a suitable temperature
h) stirring the reaction mixture at a suitable temperature
i) filtering the reaction mixture under vacuum
j) suck drying the wet solid under vacuum
k) optionally washing with wet solid with a suitable organic solvent
l) optionally drying the wet solid at a suitable temperature under vacuum to obtain crystalline Dasatinib-(±)-1,2-Butanediol solvate of Formula Ic Further according to step c), a suitable organic solvent is selected from, Dimethyl sulfoxide, N,N-Dimethyl acetamide, preferably N,N-Dimethyl acetamide Further according to step e) and step f), a suitable temperature is selected from the range consisting of 90 to 120° C., preferably, 100 to 120° C., more preferably 110 to 120° C.

Further according step g) and step h), a suitable temperature is selected from the range consisting of 30 to 65° C., preferably, 50 to 65° C., more preferably 55 to 65° C.

Further according to step k), a suitable organic solvent is selected from the group consisting of Ether solvents, Hydrocarbon solvents preferably, hydrocarbon solvent, more preferably Toluene.

Further according to step l), a suitable temperature is selected from the range consisting of 20 to 45° C., preferably, 30 to 45° C., more preferably 35 to 45° C.

Thirty first aspect of the present invention provides an alternate process for the preparation of a crystalline Dasatinib-(±)-1,2-butanediol solvate of Formula Ic, comprising the following steps, Treating the Dichloro intermediate of Formula II

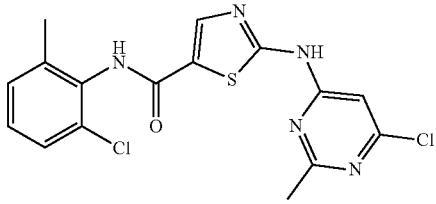

Formula II with 2-(piperazin-1-yl)ethan-1-ol of Formula III

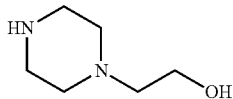

Formula III in the presence of suitable organic solvent and a suitable organic base at a suitable temperature to obtain Formula I (In-situ)

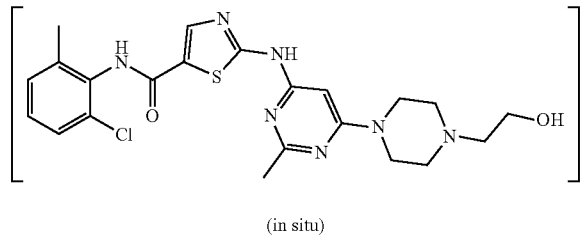

Formula I (in situ)

treating the mass containing the Formula I (in-situ) with (=)-1,2-Butanediol at a suitable temperature, to obtain a crystalline Dasatinib-(±)-1,2-butanediol solvate of Formula Ic,

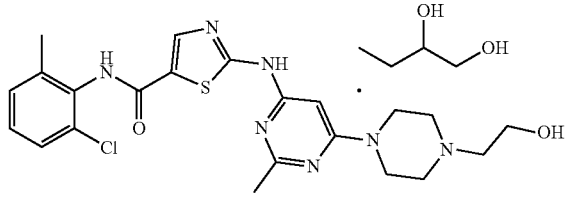

Formula Ic

Further, the present invention relates to the process for the preparation of a crystalline Dasatinib-(±)-1,2-butanediol solvate of Formula Ic, further comprising the following steps, a) charging Dichloro intermediate of Formula II into a reactor
b) adding 2-(piperazin-1-yl)ethan-1-ol of Formula III
c) adding a suitable organic solvent
d) optionally adding a suitable organic base
e) heating the reaction mass to a suitable temperature
f) maintaining the reaction mass at a suitable temperature
g) adding (±)-1,2-Butanediol
h) heating the reaction mass to a suitable temperature
i) maintaining the reaction mass at a suitable temperature
j) cooling the reaction mass to a suitable temperature
k) stirring the reaction mixture at a suitable temperature
l) filtering the reaction mixture under vacuum
m) suck drying the wet solid under vacuum
n) optionally washing with wet solid with as suitable organic solvent
o) optionally drying the wet solid at a suitable temperature under vacuum to obtain crystalline Dasatinib-(±)-1,2-butanediol solvate of Formula Ic.

Further according to step c), a suitable organic solvent is selected from, Dimethyl sulfoxide, N,N-Dimethyl acetamide, preferably N,N-Dimethyl acetamide Further according to step d), a suitable organic base is selected from the group consisting of tertiary amine, preferably Diisopropylethylamine or Triethylamine, more preferably Triethylamine.

Further according to step e) and step f), a suitable temperature is selected from the range consisting of 30 to 90° C., preferably 60 to 90° C., more preferably 83 to 87° C.

Further according to step h) and step i), a suitable temperature is selected from the range consisting of 30 to 122° C., preferably 90 to 122° C., more preferably 118 to 122° C.

Further according to step j) and step k), a suitable temperature is selected from the range consisting of 30 to 65° C., preferably 50 to 65° C., more preferably 55 to 65° C.

Further according to step n), a suitable organic solvent is selected from the group consisting of Ether solvents, Hydrocarbon solvents preferably, hydrocarbon solvent, more preferably Toluene.

Further according to step o), a suitable temperature is selected from the range consisting of 20 to 45° C., preferably 30 to 45° C., more preferably 35 to 45° C.

Thirty second aspect of the present invention provides the crystalline Dasatinib-(R)-1,2-Butanediol solvate.

Thirty third aspect of the present invention, the crystalline crystalline Dasatinib-(R)-1,2-Butanediol solvate of Formula Id is further characterized by PXRD having the main 2-theta values 5.69±0.2, 10.84±0.2, 11.30±0.2, 12.62±0.2, 13.45±0.2, 15.29±0.2, 17.15±0.2, 17.35±0.2, 18.07±0.2, 18.23±0.2, 19.41±0.2, 20.64±0.2, 21.44±0.2, 22.14±0.2, 23.90±0.2, 24.52±0.2, 25.97±0.2, 26.96±0.2, 27.19±0.2, 27.66±0.2, 31.22±0.2, 32.53±0.2, 35.60±0.2, 37.42±0.2, 46.71±0.2 and the PXRD pattern in accordance with the FIG. 12.

TABLE 4

| Num. | Gonio | d | Int | I/Imax |
|---|---|---|---|---|
| 1 | 5.6994 | 15.494 | 449 | 100.0 |
| 2 | 10.8489 | 8.14843 | 87 | 19.3 |
| 3 | 11.3075 | 7.81901 | 268 | 59.8 |
| 4 | 12.6216 | 7.00769 | 197 | 44.0 |
| 5 | 13.4568 | 6.57462 | 62 | 13.8 |
| 6 | 15.2976 | 5.78736 | 59 | 13.2 |
| 7 | 17.1589 | 5.16353 | 185 | 41.3 |
| 8 | 17.3559 | 3.10536 | 260 | 58.0 |
| 9 | 18.0714 | 4.90481 | 82 | 18.3 |
| 10 | 18.2353 | 4.8611 | 111 | 24.8 |
| 11 | 19.4145 | 4.56842 | 36 | 8.1 |
| 12 | 20.6469 | 4.29842 | 38 | 8.4 |
| 13 | 21.4450 | 4.14024 | 73 | 16.2 |
| 14 | 22.1425 | 4.01136 | 130 | 29.1 |
| 15 | 22.5174 | 3.94541 | 117 | 26.0 |
| 16 | 23.9075 | 3.71906 | 126 | 28.2 |
| 17 | 24.5281 | 3.62635 | 44 | 9.9 |
| 18 | 25.9746 | 3.42759 | 56 | 12.5 |
| 19 | 25.9674 | 3.30361 | 103 | 23.0 |
| 20 | 27.1908 | 3.27698 | 92 | 20.5 |
| 21 | 27.6631 | 3.22209 | 67 | 15.0 |
| 22 | 31.2182 | 2.86279 | 32 | 7.1 |
| 23 | 32.5391 | 2.74954 | 37 | 8.3 |
| 24 | 35.6055 | 2.51945 | 24 | 5.3 |
| 25 | 37.4285 | 2.40082 | 31 | 6.9 |
| 26 | 46.7133 | 1.94298 | 21 | 4.6 |

Thirty fourth aspect of the present invention, the crystalline crystalline Dasatinib-(R)-1,2-Butanediol solvate of Formula Id is further characterized by DSC having endotherms at around 156.6 & 286.6° C. and the DSC pattern in accordance with the FIG. 11.

Thirty fifth aspect of the present invention provides a process for the preparation of a crystalline Dasatinib-(R)-1,2-butanediol solvate of Formula Id, comprising the following steps, Treating the Dichloro intermediate of Formula II

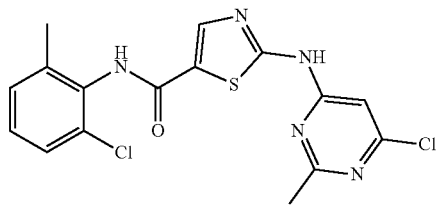

Formula II with 2-(piperazin-1-yl)ethan-1-ol of Formula III

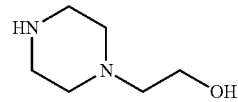

Formula III in the presence of a suitable organic solvent and (R)-1,2-butanediol and a suitable organic base at suitable temperature, to obtain a crystalline Dasatinib-(R)-1,2-butanediol solvate of Formula Id,

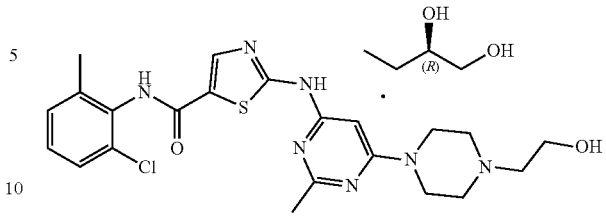

Formula-Id

Further, the present invention relates to the process for the preparation of a crystalline Dasatinib-(R)-1,2-butanediol solvate of Formula Id, further comprising the following steps,
a) charging Dichloro intermediate of Formula II into a reactor
b) adding 2-(piperazin-1-yl)ethan-1-ol of Formula III
c) optionally adding a suitable organic solvent and adding (R)-1,2-butanediol
d) optionally adding a suitable organic base
e) heating the reaction mass to a suitable temperature
f) maintaining the reaction mass at a suitable temperature
g) cooling the reaction mass to a suitable temperature
h) stirring the reaction mixture at a suitable temperature
i) filtering the reaction mixture under vacuum
j) suck drying the wet solid under vacuum
k) optionally washing with wet solid with a suitable organic solvent
l) optionally drying the wet solid at a suitable temperature under vacuum to obtain crystalline Dasatinib-(R)-1,2-Butanediol solvate of Formula Id Further according to step c), a suitable organic solvent is selected from, Dimethyl sulfoxide, N,N-Dimethyl acetamide, preferably N,N-Dimethyl acetamide Further according to step e) and step f), a suitable temperature is selected from the range consisting of 90 to 122° C., preferably 100 to 122° C., more preferably 118 to 122° C.

Further according to step g) and step h), a suitable temperature is selected from the range consisting of 30 to 65° C., preferably 50 to 65° C., more preferably 55 to 65° C.

Further according to step k), a suitable organic solvent is selected from the group consisting of Ether solvents, Hydrocarbon solvents preferably hydrocarbon solvent, more preferably Toluene.

Further according to step l), a suitable temperature is selected from the range consisting of 20 to 45° C., preferably 30 to 45° C., more preferably 35 to 45° C.

Thirty sixth aspect of the present invention provides an alternate process for the preparation of a crystalline Dasatinib-(R)-1,2-Butanediol solvate of Formula Id, comprising the following steps, Treating the Dichloro intermediate of Formula II

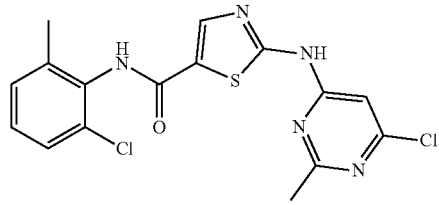

Formula II with 2-piperazin-1-yl)ethan-1-ol of Formula III

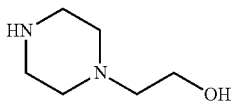

Formula III in the presence of a suitable organic solvent and a suitable organic base at a suitable temperature to obtain Formula I (In-situ)

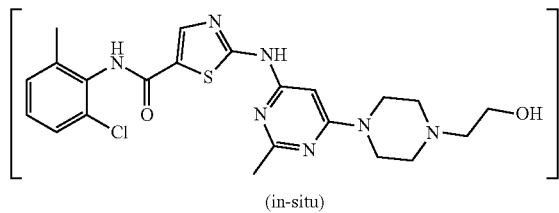

Formula 1

(in-situ)

treating the mass containing the Formula I with (R)-1,2-Butanediol at a suitable temperature, to obtain crystalline Dasatinib-(R)-1,2-butanediol solvate of Formula Id,

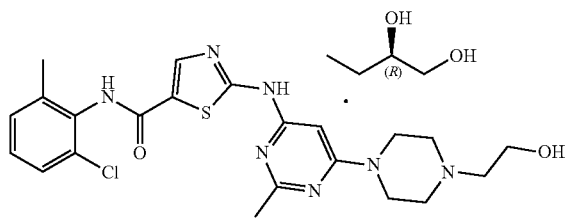

Formula-Id

Further, the present invention relates to the process for the preparation of a crystalline Dasatinib-(R)-1,2-butanediol solvate of Formula Id, further comprising the following steps,
a) charging Dichloro intermediate of Formula II into a reactor
b) adding 2-(piperazin-1-yl)ethan-1-ol of Formula III
c) adding a suitable organic solvent
d) optionally addition suitable organic base
e) heating the reaction mass to a suitable temperature
f) maintaining the reaction mass at a suitable temperature
g) adding (R)-1,2-Butanediol at a suitable temperature
h) heating the reaction mass to a suitable temperature
i) maintaining the reaction mass at a suitable temperature
j) cooling the reaction mass to a suitable temperature
k) stirring the reaction mixture at a suitable temperature
l) filtering the reaction mixture under vacuum
m) suck drying the wet solid under vacuum
n) optionally washing with wet solid with as suitable organic solvent
o) optionally drying the wet solid at a suitable temperature under vacuum to obtain crystalline Dasatinib-(R)-1,2-butanediol solvate of Formula Id Further according to step c), a suitable organic solvent is selected from Dimethyl sulfoxide, N,N-Dimethyl acetamide, preferably N,N-Dimethyl acetamide Further according to step d), a suitable organic base is selected from the group consisting of tertiary amine, preferably Diisopropylethylamine or Triethylamine, more preferably Triethylamine.

Further according to step e) and step f), a suitable temperature is selected from the range consisting of 30 to 90° C., preferably 60 to 90° C., more preferably 83 to 87° C.

Further according to step h) and step i), a suitable temperature is selected from the range consisting of 30 to 122° C., preferably 90 to 122° C., more preferably 118 to 122° C.

Further according to step j) and step k), a suitable temperature is selected from the range consisting of 30 to 65° C., preferably 50 to 65° C., more preferably 55 to 65° C.

Further according to step n), a suitable organic solvent is selected from the group consisting of Ether solvents, Hydrocarbon solvents preferably, hydrocarbon solvent, more preferably Toluene.

Further according to step o), a suitable temperature is selected from the range consisting of 20 to 45° C., preferably 30 to 45° C., more preferably 35 to 45° C.

Thirty seventh aspect of the present invention provides crystalline Dasatinib-(S)-1,2-Butanediol solvate.

Thirty eighth aspect of the present invention, the crystalline crystalline Dasatinib-(S)-1,2-Butanediol solvate of Formula Ie is further characterized by PXRD having the main 2-theta values 5.56±0.2, 8.10±0.2, 10.75±0.2, 11.18±0.2, 12.39±0.2, 13.34±0.2, 14.43±0.2, 15.07±0.2, 16.81±0.2, 17.12±0.2, 17.45±0.2, 18.02±0.2, 19.21±0.2, 19.61±0.2, 20.10±0.2, 20.43±0.2, 21.24±0.2, 21.89±0.2, 22.30±0.2, 23.70±0.2, 24.35±0.2, 25.07±0.2, 25.82±0.2, 26.72±0.2, 27.12±0.2, 27.45±0.2, 30.99±0.2, 32.33±0.2, 34.97±0.2, 35.52±0.2, 37.39±0.2, 40.97±0.2, 43.64±0.2, 46.54±0.2 and the PXRD pattern in accordance with the FIG. 13.

TABLE 5

| Num. | Gonio | d | Int | I/Imax |
|---|---|---|---|---|
| 1 | 5.5632 | 15.8729 | 1345 | 100.0 |
| 2 | 8.1023 | 10.9035 | 33 | 2.4 |
| 3 | 10.7531 | 8.22083 | 144 | 10.7 |
| 4 | 11.1800 | 7.90788 | 623 | 46.3 |
| 5 | 12.3993 | 7.13285 | 229 | 17.0 |
| 6 | 13.3473 | 6.62829 | 108 | 8.0 |
| 7 | 14.4390 | 6.12952 | 38 | 2.9 |
| 8 | 15.0774 | 5.87136 | 85 | 6.3 |
| 9 | 16.8152 | 5.26829 | 183 | 13.6 |
| 10 | 17.1202 | 5.17512 | 319 | 23.8 |
| 11 | 17.4552 | 5.17653 | 76 | 5.6 |
| 12 | 18.0232 | 4.91781 | 142 | 10.6 |
| 13 | 19.2158 | 4.61522 | 38 | 2.8 |
| 14 | 19.6114 | 4.52298 | 28 | 2.1 |
| 15 | 20.1017 | 4.41378 | 31 | 2.3 |
| 16 | 20.4359 | 4.34234 | 44 | 3.2 |
| 17 | 21.2468 | 4.1784 | 97 | 7.2 |
| 18 | 21.8969 | 4.0558 | 166 | 12.4 |
| 19 | 22.3074 | 3.98208 | 153 | 11.4 |
| 20 | 23.7051 | 3.75035 | 161 | 11.9 |
| 21 | 24.3576 | 3.65135 | 41 | 3.0 |
| 22 | 35.0753 | 3.54844 | 35 | 2.6 |
| 23 | 25.8029 | 3.44765 | 58 | 4.3 |
| 24 | 26.7244 | 3.33311 | 96 | 7.1 |
| 25 | 27.1240 | 3.2849 | 98 | 7.3 |
| 26 | 27.4580 | 3.24569 | 88 | 6.6 |
| 27 | 30.9917 | 2.88319 | 42 | 3.1 |
| 28 | 32.3337 | 2.76653 | 40 | 3.0 |
| 29 | 34.9751 | 2.56341 | 25 | 1.9 |
| 30 | 35.6234 | 2.52509 | 25 | 1.9 |
| 31 | 37.3963 | 3.40281 | 29 | 2.1 |
| 32 | 40.9758 | 2.2008 | 33 | 2.5 |
| 33 | 43.6448 | 2.0722 | 20 | 1.5 |
| 34 | 46.5436 | 1.94966 | 23 | 1.7 |

Thirty ninth aspect of the present invention provides for a process for the preparation of a crystalline Dasatinib-(S)-1,2-butanediol solvate of Formula Ie, comprising the following steps, Treating the Dichloro intermediate of Formula II

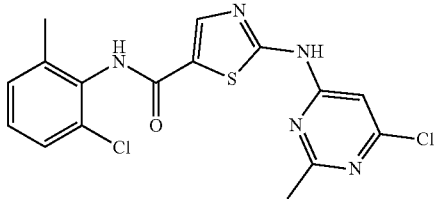

Formula II with 2-(piperazin-1-yl)ethan-1-ol of Formula III

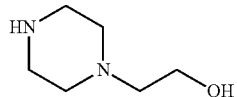

Formula III in the presence of a suitable organic solvent and (S)-1,2-Butanediol and a suitable organic base at suitable temperature, to obtain crystalline Dasatinib-(S)-1,2-butanediol solvate of Formula Ie,

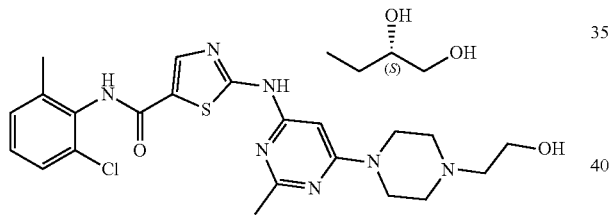

Formula Ie

Further, the present invention relates to a process for the preparation of a crystalline Dasatinib-(S)-1,2-butanediol solvate of Formula Ie, further comprising the following steps,
a) charging Dichloro intermediate of Formula II into a reactor
b) adding 2-(piperazin-1-yl)ethan-1-ol of Formula II
c) optionally adding a suitable organic solvent and adding (S)-1,2-butanediol
d) optionally adding a suitable organic base
e) heating the reaction mass to a suitable temperature
f) maintaining the reaction mass at a suitable temperature
g) cooling the reaction mass to a suitable temperature
h) stirring the reaction mixture at a suitable temperature
i) filtering the reaction mixture under vacuum
j) suck drying the wet solid under vacuum
k) optionally washing with wet solid with a suitable organic solvent
l) optionally drying the wet solid at a suitable temperature under vacuum to obtain crystalline Dasatinib-(S)-1,2-Butanediol solvate of Formula Ie Further according to step c), a suitable organic solvent is selected from, Dimethyl sulfoxide, N,N-Dimethyl acetamide, preferably N,N-Dimethyl acetamide Further according to step e) and step f), a suitable temperature is selected from the range consisting of 90 to 120° C., preferably 100 to 120° C., more preferably 110 to 120° C.

Further according to step g) and step h), a suitable temperature is selected from the range consisting of 30 to 65° C., preferably 50 to 65° C., more preferably 55 to 65° C.

Further according to step k), a suitable organic solvent is selected from the group consisting of Ether solvents, Hydrocarbon solvents preferably, hydrocarbon solvent, more preferably Toluene.

Further according to step l), a suitable temperature is selected from the range consisting of 20 to 45° C., preferably 30 to 45° C., more preferably 35 to 45° C.

Fortieth aspect of the present invention provides for an alternate process for the preparation of a crystalline Dasatinib-(S)-1,2-butanediol solvate of Formula Ie, comprising the following steps, Treating the Dichloro intermediate of Formula II

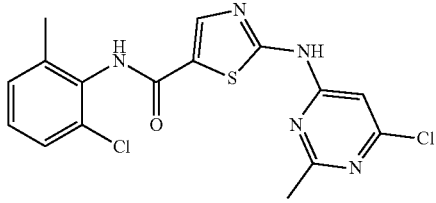

Formula II with 2-(piperazin-1-yl)ethan-1-ol of Formula III

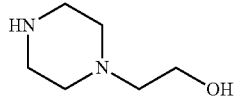

Formula III in the presence of suitable organic solvent and a suitable organic base at a suitable temperature to obtain Formula I (In-situ)

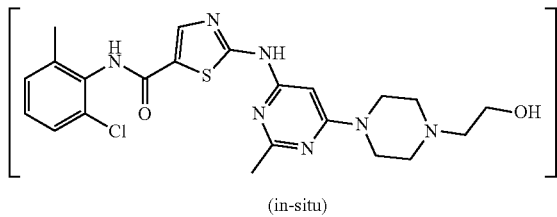

Formula I (in-situ)

treating the mass containing the Formula I (in-situ) with (S)-1,2-Butanediol at a suitable temperature, to obtain crystalline Dasatinib-(S)-1,2-butanediol solvate of Formula Ie, Formula Ie

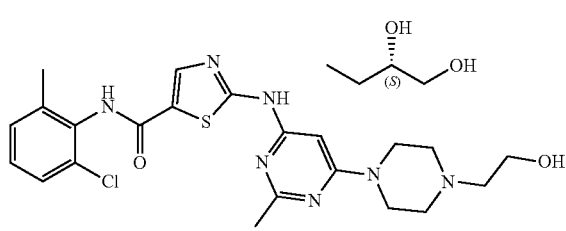

Further, the present invention relates to a process for the preparation of a crystalline Dasatinib-(S)-1,2-butanediol solvate of Formula Ie, further comprising the following steps,
a) charging Dichloro intermediate of Formula II into a reactor
b) adding 2-(piperazin-1-yl)ethan-1-ol of Formula III
c) adding a suitable organic solvent
d) optionally addition suitable organic base
e) heating the reaction mass to a suitable temperature
f) maintaining the reaction mass at a suitable temperature
g) adding (S)-1,2-Butanediol at a suitable temperature
h) heating the reaction mass to a suitable temperature
i) maintaining the reaction mass at a suitable temperature
j) cooling the reaction mass to a suitable temperature
k) stirring the reaction mixture at a suitable temperature
l) filtering the reaction mixture under vacuum
m) suck drying the wet solid under vacuum
n) optionally washing with wet solid with as suitable organic solvent
o) optionally drying the wet solid at a suitable temperature under vacuum to obtain crystalline Dasatinib-(S)-1,2-butanediol solvate of Formula Ie.

Further according to step c), a suitable organic solvent is selected from, Dimethyl sulfoxide, N,N-Dimethyl acetamide, preferably N,N-Dimethyl acetamide Further according to step d), a suitable organic base is selected from the group consisting of tertiary amine, preferably Diisopropylethylamine or Triethylamine, more preferably Triethylamine.

Further according to step e) and step f), a suitable temperature is selected from the range consisting of 30 to 90° C., preferably 60 to 90° C., more preferably 83 to 87° C.

Further according to step h) and step i), a suitable temperature is selected from the range consisting of 30 to 122° C., preferably 90 to 122° C., more preferably 118 to 122° C.

Further according to step j) and step k), a suitable temperature is selected from the range consisting of 30 to 65° C., preferably 50 to 65° C., more preferably 55 to 65° C.

Further according to step n), a suitable organic solvent is selected from the group consisting of Ether solvents, Hydrocarbon solvents preferably, hydrocarbon solvent, more preferably Toluene.

Further according to step o), a suitable temperature is selected from the range consisting of 20 to 45° C., preferably, 30 to 45° C., more preferably 35 to 45° C.

Forty first aspect of the present invention provides crystalline 2,3-Butanediol solvate.

Forty second aspect of the present invention, the crystalline Dasatinib-(±)-2, 3-Butanediol solvate of Formula Ig is further characterized by PXRD having the main 2-theta values 4.56±0.2, 5.67±0.2, 6.76±0.2, 8.13±0.2, 10.35±0.2, 11.35±0.2, 12.50±0.2, 13.09±0.2, 13.51±0.2, 14.26±0.2, 14.50±0.2, 15.30±0.2, 16.37±0.2, 16.70±0.2, 17.06±0.2, 17.29±0.2, 17.87±0.2, 19.15±0.2, 19.42±0.2, 20.02±0.2, 20.45±0.2, 20.80±0.2, 21.91±0.2, 22.97±0.2, 23.02±0.2, 23.53±0.2, 25.25±0.2, 26.16±0.2, 26.49±0.2, 27.2±00.2, 27.61±0.2, 27.95±0.2, 28.59±0.2, 30.36±0.2, 30.91±0.2, 31.43±0.2, 32.52±0.2, 32.99±0.2, 33.8±0.2, 33.98±0.2, 34.69±0.2, 35.20±0.2, 36.17±0.2, 36.52±0.2, 37.16±0.2, 37.79±0.2, 38.85±0.2, 39.81±0.2, 40.09±0.2, 40.92±0.2, 41.49±0.2, 43.34±0.2, 44.04±0.2, 44.36±0.2, 44.70±0.2, 45.76±0.2, 46.55±0.2, 47.18±0.2, 47.96±0.2, 49.11±0.2 and the PXRD pattern in accordance with the FIG. 16.

TABLE 6

| Num. | Gonio | d | Int | I/Imax |
|---|---|---|---|---|
| 1 | 4.5621 | 19.3538 | 1218 | 2.6 |
| 2 | 5.6733 | 15.5651 | 46723 | 100.0 |
| 3 | 6.7626 | 13.0603 | 1089 | 2.3 |
| 4 | 8.1329 | 10.8626 | 724 | 1.5 |
| 5 | 10.3500 | 8.54012 | 3819 | 8.2 |
| 6 | 11.3547 | 7.78657 | 26911 | 57.6 |
| 7 | 12.5047 | 7.07295 | 4435 | 9.5 |
| 8 | 13.0944 | 6.75574 | 3581 | 7.7 |
| 9 | 13.5166 | 6.54567 | 827 | 1.8 |
| 10 | 14.2635 | 6.20451 | 1168 | 2.5 |
| 11 | 14.5064 | 6.10118 | 759 | 1.6 |
| 12 | 15.3038 | 5.78503 | 1639 | 3.5 |
| 13 | 16.3767 | 5.40835 | 1053 | 2.3 |
| 14 | 16.7036 | 5.30325 | 1037 | 2.2 |
| 15 | 17.0649 | 5.19175 | 8366 | 17.9 |
| 16 | 17.2983 | 5.12223 | 9241 | 19.8 |
| 17 | 17.8747 | 4.95834 | 3837 | 8.2 |
| 18 | 19.1544 | 4.62986 | 994 | 2.1 |
| 19 | 19.4242 | 4.56617 | 584 | 1.3 |
| 20 | 20.0226 | 4.43103 | 1051 | 2.2 |
| 21 | 20.4515 | 4.33907 | 3340 | 7.1 |
| 22 | 20.8089 | 4.26534 | 666 | 1.4 |
| 23 | 21.9156 | 4.05237 | 4479 | 9.6 |
| 24 | 22.2790 | 3.98709 | 2903 | 6.2 |
| 25 | 23.0271 | 3.85923 | 2940 | 6.3 |
| 26 | 23.5386 | 3.77651 | 1052 | 2.3 |
| 27 | 25.2543 | 3.5237 | 1587 | 3.4 |
| 28 | 26.1681 | 3.40269 | 3851 | 8.2 |
| 29 | 26.4970 | 3.36119 | 1815 | 3.9 |
| 30 | 27.2053 | 3.27526 | 1785 | 3.8 |
| 31 | 27.6110 | 3.22805 | 2417 | 5.2 |
| 32 | 27.9542 | 3.18919 | 929 | 2.0 |
| 33 | 28.5974 | 3.11892 | 560 | 1.2 |
| 34 | 30.3668 | 2.94109 | 576 | 1.2 |
| 35 | 30.9190 | 2.88981 | 511 | 1.1 |
| 36 | 31.4393 | 2.84317 | 1342 | 2.9 |
| 37 | 32.5271 | 2.75052 | 1203 | 2.6 |
| 38 | 32.9934 | 2.7127 | 516 | 1.1 |
| 39 | 33.8802 | 2.64978 | 581 | 1.2 |
| 40 | 33.9810 | 2.63609 | 562 | 1.2 |
| 41 | 34.6907 | 2.58377 | 595 | 1.3 |
| 42 | 35.2088 | 2.54692 | 529 | 1.1 |
| 43 | 36.1707 | 2.48137 | 550 | 1.2 |
| 44 | 36.5245 | 2.45814 | 455 | 1.0 |
| 45 | 37.1603 | 2.41753 | 512 | 1.1 |
| 46 | 37.7906 | 2.37865 | 577 | 1.2 |
| 47 | 38.8510 | 2.31613 | 458 | 1.0 |
| 48 | 39.8156 | 2.26221 | 670 | 1.4 |
| 49 | 40.0922 | 2.24724 | 595 | 1.3 |
| 50 | 40.9296 | 2.20318 | 448 | 1.0 |
| 51 | 41.4902 | 2.17469 | 655 | 1.4 |
| 52 | 43.3423 | 2.08596 | 382 | 0.8 |
| 53 | 44.0184 | 2.05414 | 491 | 1.1 |
| 54 | 44.3676 | 2.0401 | 422 | 0.9 |
| 55 | 44.7003 | 2.02569 | 414 | 0.9 |
| 56 | 45.7654 | 1.98099 | 402 | 0.9 |
| 57 | 46.5583 | 1.94908 | 394 | 0.8 |
| 58 | 47.1824 | 1.92475 | 406 | 0.9 |
| 59 | 47.9681 | 1.89504 | 403 | 0.9 |
| 60 | 49.1109 | 1.85358 | 359 | 0.8 |

Forty third aspect of the present invention, the crystalline crystalline Dasatinib-(±)-2, 3-Butanediol solvate of Formula Ig is further characterized by DSC having endotherms at around 171.2 & 284.6° C. and the DSC pattern in accordance with the FIG. 15.

Forty fourth aspect of the present invention provides for the preparation of a crystalline Dasatinib-(±)-2,3-butanediol solvate of Formula Ig, comprising the following steps, Treating the Dichloro intermediate of Formula II

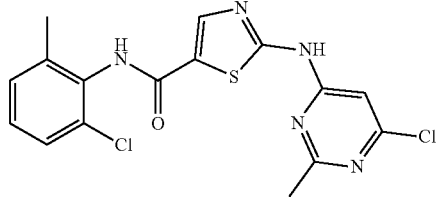

Formula II with 2-(piperazin-1-yl)ethan-1-ol of Formula III

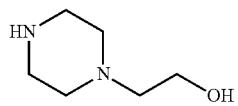

Formula III in the presence of a suitable organic solvent and (±)-2,3-Butanediol and a suitable organic base at suitable temperature, to obtain a crystalline Dasatinib-(±)-2,3-butanediol solvate of Formula I,

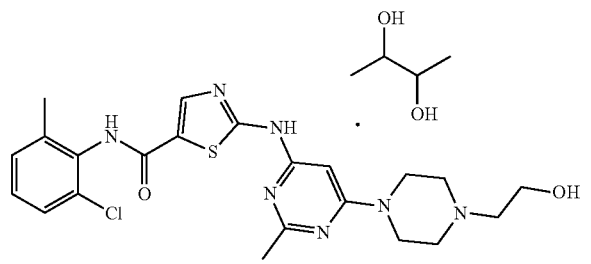

Formula Ig

Further, the present invention relates to a process for the preparation of crystalline Dasatinib-(±)-2,3-butanediol solvate of Formula Ig, further comprising the following steps,
a) charging Dichloro intermediate of Formula II into a reactor
b) adding 2-(piperazin-1-yl)ethan-1-ol of Formula III
c) optionally adding a suitable organic solvent and adding a (±)-2,3-butanediol
d) optionally adding a suitable organic base
e) heating the reaction mass to a suitable temperature
f) maintaining the reaction mass at a suitable temperature
g) cooling the reaction mass to a suitable temperature
h) stirring the reaction mixture at a suitable temperature
i) filtering the reaction mixture under vacuum
j) suck drying the wet solid under vacuum
k) optionally washing with wet solid with a suitable organic solvent
l) optionally drying the wet solid at a suitable temperature under vacuum to obtain crystalline Dasatinib-(±)-2,3-butanediol solvate of Formula Ig.

Further according to step c), a suitable organic solvent is selected from, Dimethyl sulfoxide, N,N-Dimethyl acetamide, preferably N,N-Dimethyl acetamide Further according to step e) and step f), a suitable temperature is selected from the range consisting of 90 to 120° C., preferably 100 to 120° C., more preferably 110 to 120° C.

Further according to step g) and step h), a suitable temperature is selected from the range consisting of 30 to 65° C., preferably 50 to 65° C., more preferably 55 to 65° C.

Further according to step k), a suitable organic solvent is selected from the group consisting of Ether solvents, Hydrocarbon solvents, preferably hydrocarbon solvent, more preferably Toluene.

Further according to step l), a suitable temperature is selected from the range consisting of 20 to 45° C., preferably 30 to 45° C., more preferably 35 to 45° C.

Forty fifth aspect of the present invention provides an alternate process for the preparation of a crystalline Dasatinib-(±)-2,3-butanediol solvate of Formula Ig comprising the following steps, Treating the Dichloro intermediate of Formula II

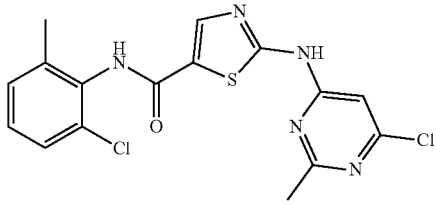

Formula II with 2-(piperazin-1-yl)ethan-1-ol of Formula III

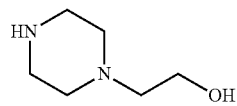

Formula III in the presence of suitable organic solvent and a suitable organic base at a suitable temperature to obtain Formula I (In-situ)

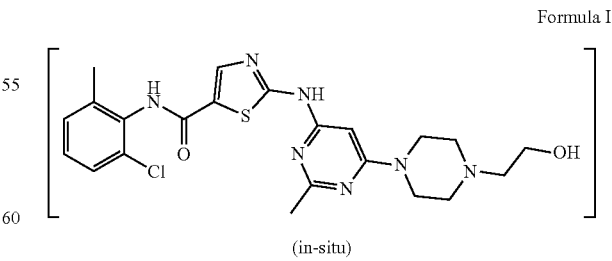

Formula I (in-situ)

treating the mass containing the Formula I (in-situ) with (=)-2,3-Butanediol at a suitable temperature, to obtain a crystalline Dasatinib-(±)-2,3-butanediol solvate of Formula I.

Formula Ig

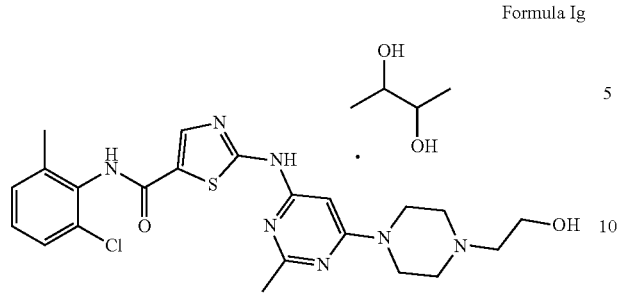

Further, the present invention relates to an alternate process for the preparation of a crystalline Dasatinib-(±)-2,3-butanediol solvate of Formula Ig, comprising the following steps,
  a) Charging Dichloro intermediate of Formula II into a reactor
  b) Adding 2-(piperazin-1-yl)ethan-1-ol of Formula III
  c) Adding a suitable organic solvent
  d) Optionally addition suitable organic base
  e) Heating the reaction mass to a suitable temperature
  f) Maintaining the reaction mass at a suitable temperature
  g) Adding (±)-2,3-Butanediol at a suitable temperature
  h) Heating the reaction mass to a suitable temperature
  i) Maintaining the reaction mass at a suitable temperature
  j) Cooling the reaction mass to a suitable temperature
  k) Stirring the reaction mixture at a suitable temperature
  l) Filtering the reaction mixture under vacuum
  m) Suck drying the wet solid under vacuum
  n) Optionally washing with wet solid with as suitable organic solvent
  o) Optionally drying the wet solid at a suitable temperature under vacuum to obtain crystalline Dasatinib-(±)-2,3-butanediol solvate of Formula Ig.

Further according to step c), a suitable organic solvent is selected from, Dimethyl sulfoxide, N,N-Dimethyl acetamide, preferably N,N-Dimethyl acetamide Further according to step d), a suitable organic base is selected from the group consisting of tertiary amine, preferably Diisopropylethylamine or Triethylamine, more preferably Triethylamine.

Further according to step e) and step f), a suitable temperature is selected from the range consisting of 30 to 90° C., preferably, 60 to 90° C., more preferably 83 to 87° C.

Further according to step h) and step i), a suitable temperature is selected from the range consisting of 30 to 122° C., preferably, 90 to 122° C., more preferably 118 to 122° C.

Further according to step j) and step k), a suitable temperature is selected from the range consisting of 30 to 65° C., preferably, 50 to 65° C., more preferably 63 to 65° C.

Further according to step n), a suitable organic solvent is selected from the group consisting of Ether solvents, Hydrocarbon solvents preferably, hydrocarbon solvent, more preferably Toluene.

Further according to step o), a suitable temperature is selected from the range consisting of 20 to 45° C., preferably, 30 to 45° C., more preferably 35 to 45° C.

Forty sixth aspect of the present invention provides a process for the preparation of Amorphous Dasatinib of Formula I, comprising the following steps, Treating the Dichloro intermediate of Formula II Formula II

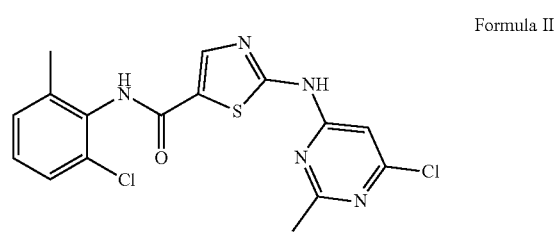 [SMILES: Cc1nc(Cl)cc(Nc2ncc(C(=O)Nc3c(C)cccc3Cl)s2)n1]

with 2(piperazin-1-yl)ethan-1-ol of Formula III

Formula III

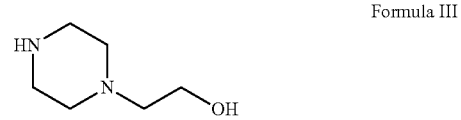

in the presence of a suitable organic solvent and a suitable organic base at a suitable temperature to obtain Dasatinib of Formula I (in-situ)

Formula I

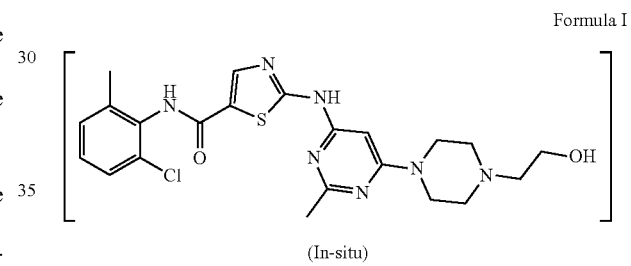

(In-situ)

followed by treating the reaction mass with a suitable Butanediol to obtain a crystalline Dasatinib-Butanediol solvate of Formula Ic or Formula Id or Formula Ie or Formula Ig, Formula Ic (or) Id (or) Ie (or) Ig
Butanediol

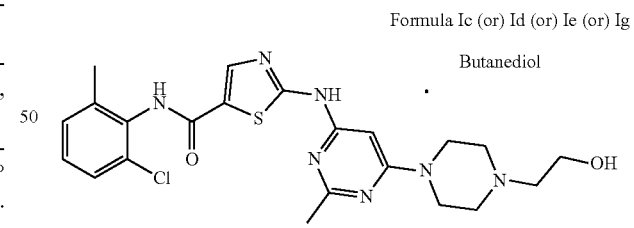

Wherein, Butanediol=(±)-1,2-Butane diol or (R)-1,2-Butanediol or (S)-1,2-Butanediol or (±)-2,3-Butanediol Formula Ic=Dasatinib-(±)-1,2-Butane diol solvate
Formula Id=Dasatinib-(R)-1,2-Butanediol solvate
Formula Ie=Dasatinib-(S)-1,2-Butanediol solvate
Formula Ig=Dasatinib-(±)-2,3-Butane diol solvate Treating a crystalline Dasatinib-Butanediol solvate of Formula I or Formula Id or Formula Ie or Formula Ig in a suitable acid aq. solution and treating with aq. Ammonia solution to obtain Amorphous Dasatinib of Formula I

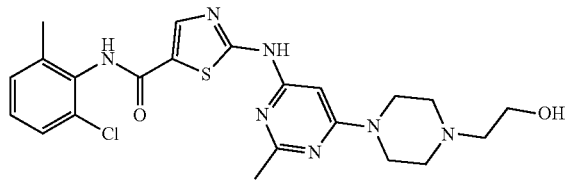

Formula I

Further, the present invention relates to a process for the preparation of Amorphous Dasatinib of Formula I, further comprising the following steps,
a) Charging Dichloro intermediate of Formula II into a reactor
b) Adding 2-(piperazin-1-yl)ethan-1-ol of Formula III
c) Adding a suitable organic solvent
d) Optionally adding a suitable organic base
e) Heating the reaction mass to a suitable temperature
f) Maintaining the reaction mass at a suitable temperature
g) Adding suitable Butanediol at a suitable temperate
h) Heating the reaction mass to a suitable temperature
i) Maintaining the reaction mass at a suitable temperature
j) Cooling the reaction mass to a suitable temperature
k) Stirring the reaction mixture at a suitable temperature
l) Filtering the reaction mixture under vacuum
m) Suck drying the wet solid under vacuum
n) Optionally washing with wet solid with as suitable organic solvent
o) Optionally drying the wet solid
p) Contacting the wet solid of Dasatinib-Butanediol solvate of Formula Ic or Formula Id or Formula Ie or Formula Ig with a suitable acid and water at a suitable temperature
q) Cooling the mass to a suitable temperature
r) Treating the mass with aq. Ammonia solution at suitable temperature
s) Warming the mass to a suitable temperature
t) Maintaining the mass at suitable temperature
u) Filtering and washing the wet solid with water
v) Drying the wet solid at a suitable temperature under vacuum to obtain Amorphous Dasatinib of Formula I Further according to step c), a suitable organic solvent is selected from the group consisting of Sulfoxide, Amide solvents, preferably Dimethyl sulfoxide, N,N-Dimethyl acetamide, more preferably N,N-Dimethyl acetamide.

Further according to step d), a suitable organic base is selected from the group consisting of tertiary amine, preferably N,N-Diisopropylethylamine, Triethylamine, more preferably Triethylamine.

Further according to step e), step f) and step g) a suitable temperature is selected from the range consisting of 30 to 90° C., preferably 80 to 90° C., more preferably 83 to 87° C.

Further according to step g) suitable butanediol is selected from the group consisting of vicinal butanediol, more preferably isomer/isomeric mixture of 2,3-Butanediol or isomer/isomeric mixture of 1,2-butanediol, most preferably (1)-1,2-Butanediol or (R)-1,2-Butanediol or (S)-1,2-Butanediol or (±)-2,3-Butanediol.

Further according to step h) and step i), a suitable temperature is selected from the range consisting of 90 to 122° C., preferably 100 to 122° C., more preferably 118 to 122° C.

Further according to step j) and step k), a suitable temperature is selected from the range consisting of 30 to 67° C., preferably 50 to 67° C., more preferably 63 to 67° C.

Further according to step n), a suitable organic solvent is selected from the group consisting of Ether solvents, Hydrocarbon solvents, preferably hydrocarbon solvent, more preferably Toluene.

Further according to step p), step s) and step t) a suitable temperature is selected from the range consisting of 10 to 30° C., preferably 15 to 20° C., more preferably 20 to 30° C.

Further according to step q) and step r) a suitable temperature is selected from the range consisting of 5 to 30° C., preferably 5 to 20° C., more preferably 5 to 15° C.

Further according to step v), a suitable temperature is selected from the range consisting of 30 to 60° C., preferably, 40 to 60° C., more preferably 50 to 60° C.

The input for the process for the preparation of Amorphous Dasatinib according to one 30 aspect of present invention is a crystalline Dasatinib-Butanediol solvate of Formula Ic or Formula Id or Formula Ie or Formula Ig preferably Dasatinib-(±)1,2-Butanediol solvate or crystalline Dasatinib-(R)-1,2-Butanediol solvate or crystalline Dasatinib-(S)-1,2-Butanediol solvate or crystalline Dasatinib-(±)-2,3-Butanediol solvate. Wherein, Formula Ic is Dasatinib-(±)-1,2-Butane diol solvate, Formula Id is Dasatinib-(R)-1,2-Butanediol solvate, Formula Ie is Dasatinib-(S)-1,2-Butanediol solvate, Formula Ig is Dasatinib-(±)-2,3-Butane diol solvate.

Forty seventh aspect of the present invention provides a process for the preparation of Amorphous Dasatinib, comprising the following steps, Treating the Dichloro intermediate of Formula II

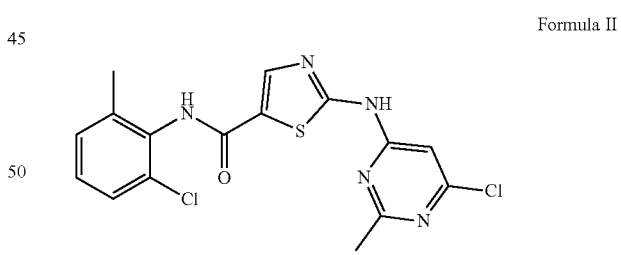

Formula II with 2-(piperazin-1-yl)ethan-1-ol of Formula III

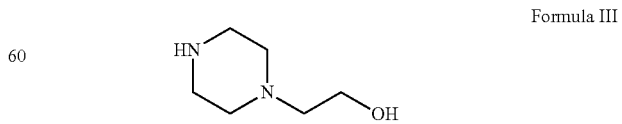

Formula III in the presence of a suitable organic solvent and a suitable organic base at a suitable temperature, to obtain a crystalline Dasatinib-(±)-1,2-Butanediol solvate of Formula Ic,

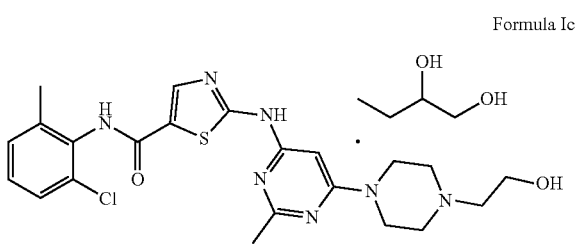

Formula Ic treating a crystalline Dasatinib-(±)-1,2-Butanediol solvate of Formula Ic with a suitable acid aqueous solution and treating with aq. Ammonia solution to obtain Amorphous Dasatinib.

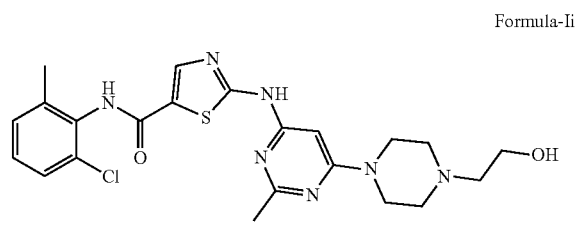

Formula-Ii

Further, the present invention relates to a process for the preparation of Amorphous Dasatinib, further comprising the following steps,
a) charging Dichloro intermediate of Formula II into a reactor
b) adding 2-(piperazin-1-yl)ethan-1-ol of Formula III
c) adding a suitable organic solvent
d) optionally adding a suitable organic base
e) heating the reaction mass to a suitable temperature
f) maintaining the reaction mass at a suitable temperature
g) adding (±)-1,2-Butanediol at a suitable temperate
h) heating the reaction mass to a suitable temperature
i) maintaining the reaction mass at a suitable temperature
j) cooling the reaction mass to a suitable temperature
k) stirring the reaction mixture at a suitable temperature
l) filtering the reaction mixture under vacuum
m) suck drying the wet solid under vacuum
n) optionally washing the wet solid with as suitable organic solvent
o) optionally drying the wet solid
p) Contacting the wet solid of Dasatinib-(±)-1,2-Butanediol solvate of Formula Ie with water and citric acid at a suitable temperature
q) cooling the mass to a suitable temperature
r) treating the mass with aq. Ammonia solution at suitable temperature
s) warming the mass to a suitable temperature
t) maintaining the mass at suitable temperature
u) filtering and washing the wet solid with water
v) drying the wet solid at a suitable temperature under vacuum to obtain Amorphous Dasatinib.

Further according to step c), a suitable organic solvent is selected from the group consisting of Sulfoxide, Amide solvents, preferably Dimethyl sulfoxide, N,N-Dimethyl acetamide, more preferably N,N-Dimethyl acetamide.

Further according to step d), a suitable organic base is selected from the group consisting of tertiary amine, preferably N,N-Diisopropylethylamine, Triethylamine, more preferably Triethylamine.

Further according to step e), step f) and step g) a suitable temperature is selected from the range consisting of 30 to 90° C., preferably 80 to 90° C., more preferably 83 to 87° C.

Further according to step h) and step i), a suitable temperature is selected from the range consisting of 90 to 122° C., preferably 100 to 122° C., more preferably 118 to 122° C.

Further according in step j) and step k), a suitable temperature is selected from the range consisting of 30 to 67° C., preferably 50 to 67° C., more preferably 63 to 67° C.

Further according to step n), a suitable organic solvent is selected from the group consisting of Ether solvents, Hydrocarbon solvents, preferably hydrocarbon solvent, more preferably Toluene.

Further according to step p), step s) and step t) a suitable temperature is selected from the range consisting of 10 to 30° C., preferably 15 to 20° C., more preferably 20 to 30° C.

Further according to step q) and step r) a suitable temperature is selected from the range consisting of 5 to 30° C., preferably 5 to 20° C., more preferably 5 to 15° C.

Further according to step v), a suitable temperature is selected from the range consisting of 30 to 60° C., preferably 40 to 60° C., more preferably 50 to 60° C.

According to the one of the aspects of present invention the input for the process for the preparation of Amorphous Dasatinib is Dasatinib-(±)1,2-Butanediol solvate Forty eighth aspect of the present invention provides a process for the preparation of Amorphous Dasatinib, comprising the following steps, Treating the Dichloro intermediate of Formula II

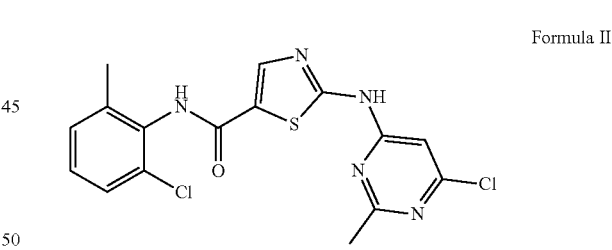

Formula II with 2-(piperazin-1-yl)ethan-1-ol of Formula III

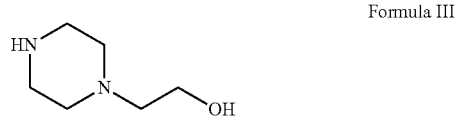

Formula III in the presence of a suitable organic solvent and a suitable organic base at a suitable temperature, to obtain crystalline Dasatinib-(R)-1,2-Butanediol solvate of Formula Id,

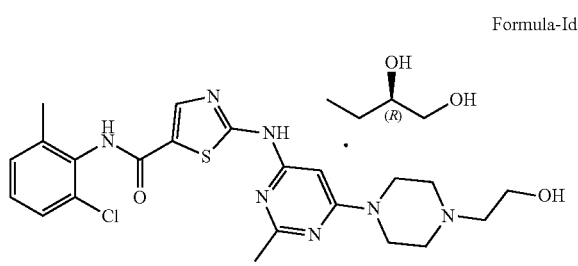

Formula-Id

Contacting a crystalline Dasatinib-(R)-1,2-Butanediol solvate of Formula Id with a suitable acid aqueous solution, treating with Aq. Ammonia solution to obtain Amorphous Dasatinib.

Further, the present invention relates to a process for the preparation of Amorphous Dasatinib, further comprising the following steps,
  a) charging Dichloro intermediate of Formula II into a reactor
  b) adding 2-(piperazin-1-yl)ethan-1-ol of Formula III
  c) adding a suitable organic solvent
  d) optionally adding a suitable organic base
  e) heating the reaction mass to a suitable temperature
  f) maintaining the reaction mass at a suitable temperature
  g) adding (R)-1,2-Butanediol at a suitable temperate
  h) heating the reaction mass to a suitable temperature
  i) maintaining the reaction mass at a suitable temperature
  j) cooling the reaction mass to a suitable temperature
  k) stirring the reaction mixture at a suitable temperature
  l) filtering the reaction mixture under vacuum
  m) suck drying the wet solid under vacuum
  n) optionally washing with wet solid with as suitable organic solvent
  o) optionally drying the wet solid
  p) contacting the wet solid of Dasatinib-(R)-1,2-Butanediol solvate of Formula Id with water and citric acid at suitable temperature
  q) cooling the mass to a suitable temperature
  r) treating the mass with aq. Ammonia solution at suitable temperature
  s) warning the mass to a suitable temperature
  t) maintaining the mass at suitable temperature
  u) filtering and washing the wet solid with water
  v) drying the wet solid at a suitable temperature under vacuum to obtain Amorphous Dasatinib.

Further according to step c), a suitable organic solvent is selected from the group consisting of Sulfoxide, Amide solvents, preferably Dimethyl sulfoxide, N,N-Dimethyl acetamide, more preferably N,N-Dimethyl acetamide.

Further according to step d), a suitable organic base is selected from the group consisting of tertiary amine, preferably N,N-Diisopropylethylamine, Triethylamine, more preferably Triethylamine.

Further according to step e), step f) and step g) a suitable temperature is selected from the range consisting of 30 to 90° C., preferably 80 to 90° C., more preferably 83 to 87° C.

Further according to step h) and step i), a suitable temperature is selected from the range consisting of 90 to 122° C., preferably 100 to 122° C., more preferably 118 to 122° C.

Further according to step j) and step k), a suitable temperature is selected from the range consisting of 30 to 67° C., preferably 50 to 67° C., more preferably 63 to 67° C.

Further according to step n), a suitable organic solvent is selected from the group consisting of Ether solvents, Hydrocarbon solvents, preferably hydrocarbon solvent, more preferably Toluene.

Further according to step p), step s) and step t) a suitable temperature is selected from the range consisting of 10 to 30° C., preferably 15 to 20° C., more preferably 20 to 30° C.

Further according to step q) and step r) a suitable temperature is selected from the range consisting of 5 to 30° C., preferably 5 to 20° C., more preferably 5 to 15° C.

Further according to step v), a suitable temperature is selected from the range consisting of 30 to 60° C., preferably 40 to 60° C. more preferably 50 to 60° C.

Forty ninth aspect of the present invention provides a process for the preparation of Amorphous Dasatinib, comprising the following steps, Treating the Dichloro intermediate of Formula II

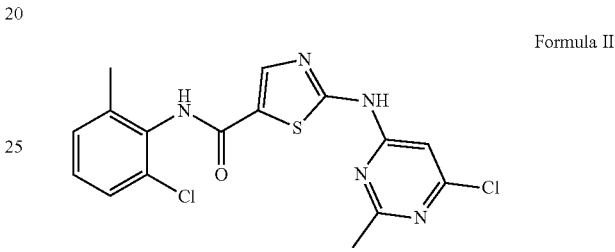

Formula II with 2-(piperazin-1-yl)ethan-1-ol of Formula III

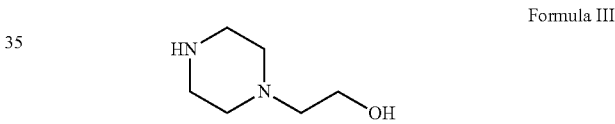

Formula III in the presence of a suitable organic solvent and a suitable organic base at a suitable temperature, to obtain a crystalline Dasatinib-(S)-1,2-Butanediol solvate of Formula Ie,

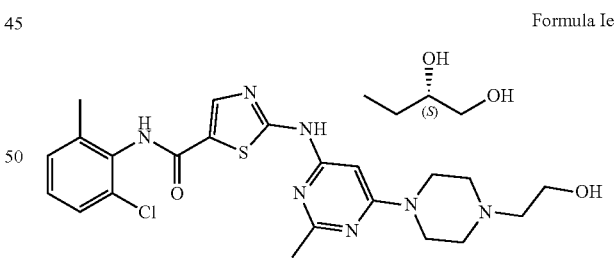

Formula Ie treating a crystalline Dasatinib-(S)-1,2-Butanediol solvate of Formula Ie with a suitable acid aqueous solution, treating with aq. Ammonia solution to obtain Amorphous Dasatinib Further, the present invention relates to a process for the preparation of Amorphous Dasatinib, further comprising the following steps,
  a) charging Dichloro intermediate of Formula II into a reactor
  b) adding 2-(piperazin-1-yl)ethan-1-ol of Formula III
  c) adding a suitable organic solvent
  d) optionally adding a suitable organic base
  e) heating the reaction mass to a suitable temperature f) maintaining the reaction mass at a suitable temperature
g) adding (S)-1,2-Butanediol at a suitable temperate
h) heating the reaction mass to a suitable temperature
i) maintaining the reaction mass at a suitable temperature
j) cooling the reaction mass to a suitable temperature
k) stirring the reaction mixture at a suitable temperature
l) filtering the reaction mixture under vacuum
m) suck drying the wet solid under vacuum
n) optionally washing with wet solid with as suitable organic solvent
o) optionally drying the wet solid
p) contacting the wet solid of Dasatinib-(S)-1,2-Butanediol solvate of Formula Ie with water and citric acid at suitable temperature
q) cooling the mass to a suitable temperature
r) treating the mass with aq. Ammonia solution at suitable temperature
s) warming the mass to a suitable temperature
t) maintaining the mass at suitable temperature
u) filtering and washing the wet solid with water
v) drying the wet solid at a suitable temperature under vacuum to obtain Amorphous Dasatinib.

Fiftieth aspect of the present invention provides a process for the preparation of Amorphous Dasatinib, comprising the following steps, Treating the Dichloro intermediate of Formula II

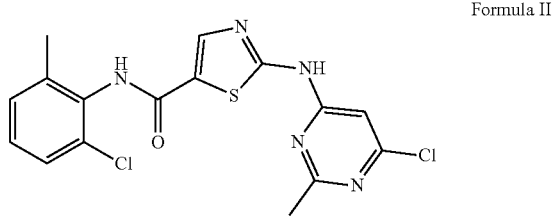 [SMILES: Cc1nc(Cl)cc(Nc2ncc(C(=O)Nc3c(C)cccc3Cl)s2)n1]

Formula II with 2-(piperazin-1-yl)ethan-1-ol of Formula III

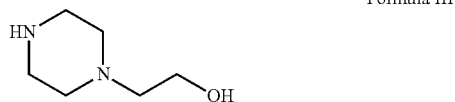

Formula III in the presence of a suitable organic solvent and a suitable organic base at a suitable temperature, to obtain a crystalline Dasatinib-(±)-2,3-Butanediol solvate of Formula Ig,

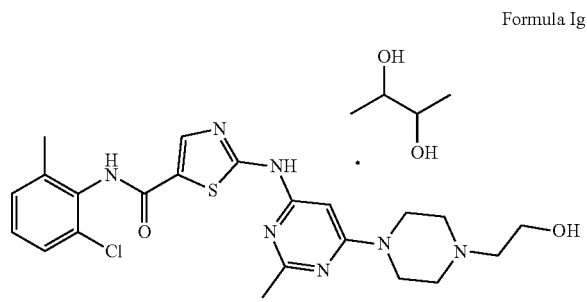

Formula Ig treating crystalline Dasatinib-(±)-2,3-Butanediol solvate of Formula Ig with a suitable acid aqueous solution, treating with aq. Ammonia solution to obtain Amorphous Dasatinib Further, the present invention relates to a process for the preparation of Amorphous Dasatinib, further comprising the following steps,
a) charging Dichloro intermediate of Formula II into a reactor
b) adding 2-(piperazin-1-yl)ethan-1-ol of Formula III
c) adding a suitable organic solvent
d) optionally adding a suitable organic base
e) heating the reaction mass to a suitable temperature
f) maintaining the reaction mass at a suitable temperature
g) adding (±)-2,3-Butanediol at a suitable temperate
h) heating the reaction mass to a suitable temperature
i) maintaining the reaction mass at a suitable temperature
j) cooling the reaction mass to a suitable temperature
k) stirring the reaction mixture at a suitable temperature
l) filtering the reaction mixture under vacuum
m) suck drying the wet solid under vacuum
n) optionally washing with wet solid with as suitable organic solvent
o) optionally drying the wet solid
p) contacting the wet solid of Dasatinib-(±)-2,3-Butanediol solvate of Formula Ig with water and citric acid at suitable temperature
q) cooling the mass to a suitable temperature
r) treating the mass with aq.Ammonia solution at suitable temperature
s) warming the mass to a suitable temperature
t) maintaining the mass at suitable temperature
u) filtering and washing the wet solid with water
v) drying the wet solid at a suitable temperature under vacuum to obtain Amorphous Dasatinib.

Fifty first aspect of the present invention provides a process for the preparation of Anhydrous Dasatinib, comprising the following steps, Treating the Dichloro intermediate of Formula II

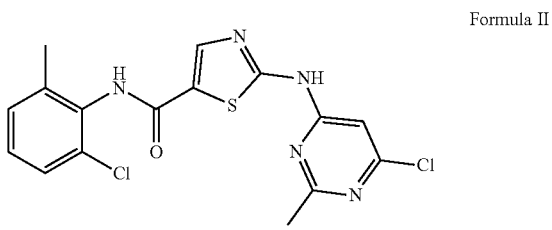 [SMILES: Cc1nc(Cl)cc(Nc2ncc(C(=O)Nc3c(C)cccc3Cl)s2)n1]

Formula II with 2-(piperazin-1-yl)ethan-1-ol of Formula III

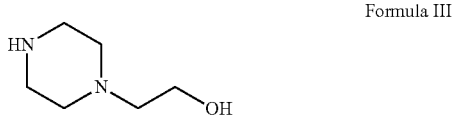

Formula III in the presence of a suitable organic solvent at a suitable temperature, to obtain crystalline Anhydrous Dasatinib.

Further, the present invention relates to a process for the preparation of Anhydrous Dasatinib, further comprising the following steps,
a) charging Dichloro intermediate of Formula II into a reactor
b) adding 2-(piperazin-1-yl)ethan-1-ol of Formula III
c) adding a suitable organic solvent
d) heating the reaction mass to a suitable temperature
e) maintaining the reaction mass at a suitable temperature f) adding a suitable organic solvent at a suitable temperate
g) maintaining the reaction mass at a suitable temperature
h) cooling the reaction mass to a suitable temperature
i) stirring the reaction mixture at a suitable temperature
j) filtering the reaction mixture under vacuum
k) washing with wet solid with as suitable organic solvent
l) suck drying the wet solid under vacuum
m) drying the wet solid at a suitable temperature under vacuum to obtain Anhydrous Dasatinib.

Further according to step c), step f) and step k), a suitable organic solvent is selected from the group consisting Alcohol solvents, preferably Methanol Further according to step d), step e), step f) and step g), a suitable temperature is selected from the range consisting of 50 to 69° C., preferably 60 to 69° C., more preferably 65 to 69° C.

Further according to step h) and step i), a suitable temperature is selected from the range consisting of 5 to 30° C., preferably 10 to 30° C., more preferably 20 to 30° C.

Further according to step m), a suitable temperature is selected from the range consisting of 30 to 60° C., preferably 40 to 60° C., more preferably 50 to 60° C.

Fifty second aspect of the present invention provides a process for the preparation of Dasatinib Monohydrate, The process for the preparation of Dasatinib Monohydrate, comprising the following steps, Treating the Dichloro intermediate of Formula II Formula II with 2-(piperazin-1-yl)ethan-1-ol of Formula III Formula III in the presence of a suitable organic solvent at a suitable temperature, to obtain crystalline Anhydrous Dasatinib, Treating Anhydrous Dasatinib with suitable solvent(s) at a suitable temperature to obtain Dasatinib Monohydrate.

Further, the present invention relates to a process for the preparation of Anhydrous Dasatinib, further comprising the following steps,
a) charging Dichloro intermediate of Formula II into a reactor b) adding 2-(piperazin-1-yl)ethan-1-ol of Formula III
c) adding a suitable organic solvent
d) heating the reaction mass to a suitable temperature
e) maintaining the reaction mass at a suitable temperature
f) adding a suitable organic solvent at a suitable temperate
g) maintaining the reaction mass at a suitable temperature
h) cooling the reaction mass to a suitable temperature
i) stirring the reaction mixture at a suitable temperature
j) filtering the reaction mixture under vacuum
k) washing the wet solid with as suitable organic solvent
l) suck drying the wet solid under vacuum
m) drying the wet solid at a suitable temperature under vacuum to obtain Anhydrous Dasatinib
n) Treating the Anhydrous Dasatinib with suitable solvent(s) at a suitable temperature
o) maintaining the reaction mass at a suitable temperature
p) cooling the mass to a suitable temperature
q) maintaining the reaction mass at a suitable temperature
r) filtering and washing the wet solid with suitable solvent
s) drying the wet solid at a suitable temperature under vacuum to obtain Dasatinib Monohydrate.

Further according to step c), step f) and step k), a suitable organic solvent is selected from the group consisting Alcohol solvents, preferably Methanol.

Further according to step d), step e), step f) and step g), a suitable temperature is selected from the range consisting of 50 to 69° C., preferably 60 to 69° C., more preferably 65 to 69° C.

Further according to step h), step i), step p) and step q), a suitable temperature is selected from the range consisting of 5 to 30° C., preferably 10 to 30° C., more preferably 20 to 30° C.

Further according to step m) and step s), a suitable temperature is selected from the range consisting of 30 to 60° C., preferably 40 to 60° C., more preferably 50 to 60° C.

Further according to step n) and step o), a suitable temperature is selected from the range consisting of 50 to 90° C., preferably 60 to 90° C., more preferably 80 to 90° C.

Accordingly, the different crystalline Dasatinib forms of the present invention are prepared and characterised by orthogonal analytical tools.

Characterization Techniques:

FT-IR, DSC, 1H NMR and PXRD techniques were used for characterising the co-crystal. The infrared spectroscopy, presents a great quantity of information about the chemical bonds and interaction. It is a fast analysis method, non-destructive.

The Powder X-ray diffraction is one of the most used techniques to determine different crystalline structures. This technique can distinguish the presence of a new crystallographic motif, which can be a polymorph or a co-crystal. It is a non-destructive method and presents diffractions patterns unique for each structure.

The differential scanning calorimetry is a characterization method based on the heat of reaction involved in different thermal events. For the pharmaceutical industry, the DSC is mostly used to obtain melting points of the API and thus, determine its purity. For the co-crystal analysis, there is a clear difference between the melting point of the co-former and the co-crystal itself.

Instrumental Parameters:

The $^1$H-NMR spectrum recorded in Bruker 400 MHz spectrometer using DMSO-d6 as solvent and chemical shifts are reported in ppm downfield from TMS.

DSC was performed on a Discovery DSC (TA instruments). About 3-5 mg of sample placed in crimped aluminium sample pan to be positioned on auto sampler. The temperature range was from 30-350 OC @ 10° C./min. Samples were purged by a stream of nitrogen flowing at 50 mL/min.

Equilibrate: 30° C.
Ramp: 10° C./min
Range: 30° C.-350° C.

The FT-IR spectrum (Fourier transform R spectroscopy) was recorded using the Fisher Scientific (NICOLET-iS50-FTIR), equipped with a KBr splitter and a DTGS KBr detector. The spectrum was recorded in the range of 4000 cm−1 to 400 cm−1

The powder X-ray powder diffractogram (XRPD) was obtained by using the instrument XRD BRUKER D8 ADVANCE, equipped with LYNXEYE detector with 40 mA current intensity and 40 kV voltage.

The sample was arranged on a Si-Zero background Sample holder and analysed using the following parameters:
Scanning range (°): 3.000 to 60.000
Step size (°): 0.03
Scan type: Locked coupled
Scanning mode: continuous
Count time per step (s): 0.5
Delay time (s): 0
Divergent slit: 0.300
Antiscatter slit: 0.300

Advantages of Present Invention

An API can exist in a variety of solid state forms, which include: polymorphs; solvates; hydrates, salts; co-crystals and amorphous forms. Each form exhibits unique physio-chemical properties that can profoundly influence the bio-availability, stability, manufacturability and other performance characteristics of the Formulated API.

Crystalline forms when compared to the amorphous form often show desired unique physical and/or biological characteristics which usually contributes in the manufacture or Formulation of the active compound, to the purity levels and uniformity required for regulatory approval. Hence, it is desirable to provide the pharmaceutically active ingredient in a substantially pure, crystalline and stable form of API.

Furthermore, the provision of further crystalline forms of a pharmaceutically useful compound offers an opportunity to improve the performance profile of a pharmaceutical product. In particular, not all solid forms of a pharmaceutically useful compound are equally suited for development of a pharmaceutical dosage form. It is therefore desirable to widen the reservoir of materials a Formulation scientist can select from, such that he can design a new dosage form of a drug having improved characteristics.

In simple terms, Co-crystals are an important class of pharmaceutical materials that can enhance solubility and dissolution by forming a crystal of a drug and other benign molecule or co-former with specific stoichiometric compositions.

According to Almarsson and Zaworotko the definition of pharmaceutical co-crystals-co-crystals are those that are formed between an active pharmaceutical ingredient (API) and a co-crystal former (CF), which is a solid under ambient conditions, and is not limited to two components. The components of the crystal interact by hydrogen bond or other noncovalent and non-ionic interactions (Ö. Almarsson, M. J. Zaworotko, "Crystal engineering of the composition of pharmaceutical phases. Do pharmaceutical co-crystals represent anew path to improved medicines?" *Chem. Commun.* 2004, 17, pp. 1889-1896).

Dasatinib is a drug with poor solubility in water. Hence, there exists a real need to improve the aqueous solubility of Dasatinib for better bioavailability.

Generally, the poor solubility of drugs in water can be improved using formation of their respective co-crystals (*International Journal of Pharmaceutics.* 2013, 453, 101).

The solution to the technical problem underlying the present invention is the provision of a crystalline forms comprising Dasatinib-Thymine co-crystal, Dasatinib-Adenine co-crystal and the provision of processes for obtaining the same.

In an endeavor to achieve stable crystalline co-crystals of Dasatinib, different co-formers have been screened. Co-formers have been selected by keeping in mind the basicity of Dasatinib. Accordingly, Piperazine, Methyl paraben, Thymine & Adenine were attempted for co-crystal formation. However, our results indicated co-crystal formation with co-formers namely Thymine & Adenine. The crystalline co-crystal obtained has been characterized by orthogonal analytical tools namely 1H NMR. DSC, PXRD and FT-R.

It is therefore an object of the present invention to provide a highly reproducible and economical process of providing Dasatinib-Thymine co-crystal of Formula Ia and Dasatinib-Adenine co-crystal of Formula Ib in substantially pure forms. Furthermore, it would be desirable to provide crystalline solid forms of Dasatinib-Thymine co-crystal of Formula Ia and Dasatinib-Adenine co-crystal of Formula Ib showing improved physical and/or biological characteristics.

Advantages of Usage of Thymine & Adenine as Co-Formers

Thymine is one of the pyrimidine bases found in DNA and Adenine is one of the purine bases found in DNA and is a constituent of numerous coenzymes.
$LD_{50}$ value for thymine is 3500 mg/Kg (Organism: rat, Route: oral) & $LD_{50}$ value for Adenine is 227 mg/Kg (Organism: rat, Route: oral).
Both Thymine & Adenine are thermally stable (melting points of both Thymine & Adenine are greater than 300° C.).
Both Thymine & Adenine are chemically stable.
Both Thymine & Adenine are non-hygroscopic.
Both Thymine & Adenine are easy to handle as they are a free flowing powders.
Both Thymine & Adenine have availability of Hydrogen bond donors and acceptors Advantages of Dasatinib-Thymine & Dasatinib-Adenine Co-Crystals Literature mentions about better solubility of anhydrous Dasatinib (2.40 times) compared to Monohydrate form (*Crys. Growth Des.* 2012, 12, 2122-2126). WO2013186726A2 mentions about the advantages in solubility of dasatinib co-crystals over Monohydrate and anhydrous forms.
Dasatinib-Thymine co-crystal & Dasatinib-Adenine co-crystals of present invention have the considerably higher solubility in water and aqueous buffer solution in comparison to the Dasatinib Monohydrate.

The present invention relates to Dasatinib-Thymine co-crystal & Dasatinib-Adenine co-crystals which has relatively less hygroscopicity in comparison with the anhydrous Dasatinib.

The processes of the present invention for the formation of co-crystals does not involve the need to use Dasatinib monohydrate as the input material.

One of the processes of the present invention involves one-pot synthesis of Dasatinib-Thymine co-crystal formation without the isolation of Dasatinib as intermediate.

The processes of the present invention for the preparation of Dasatinib-Thymine co-crystal & Dasatinib-Adenine co-crystals are scale-up friendly.

The process of the present invention for the preparation of Dasatinib-Thymine co-crystal & Dasatinib-Adenine co-crystals does not involve the necessity of inert condition, hence economical and easy to operate.

The process of the present invention does not involve additional operations during workup such as layer separation and evaporations hence economical, time saving and easy to operate.

Advantages of Dasatinib Butanediol Solvate

Economic and scalable process
Eco-friendly reagents and solvents are used
Direct isolation Dasatinib-Butanediol solvate without isolating any solid form of Dasatinib
Usage of less volume (5.00 v) of butane diols for the formation of Dasatinib-Butanediol solvate
Controlling the Dasatinib-N-oxide impurity without using any antioxidants in the reaction
Direct isolation of substantially pure Dasatinib-Butanediol solvate without any additional purification
Elimination of the laborious workup such us layer separation, concentration, trituration and re-crystallisation etc.

Advantages of Process for Preparation of Dasatinib Amorphous Form from Butanediol Solvate Economic and scalable process
Eco-friendly reagent and solvents are used
Direct isolation Amorphous Dasatinib without isolating any solid form of Dasatinib
Usage of less volumes (around 5.00 to 10.0 v) of solvent for the formation of Amorphous Dasatinib
Controlling the Dasatinib-N-oxide impurity without using any antioxidants in the reaction
Isolation of substantially pure Amorphous Dasatinib without any additional purification
Elimination of the laborious workup such us layer separation, concentration, trituration and re-crystallisation etc.
Usage of mild organic acid (solid) and mild base for the formation of Amorphous Dasatinib
reparation of Amorphous Dasatinib without isolation any acid addition salts
Preparation procedure of Amorphous Dasatinib does not usage of any polymers
Preparation procedure of Amorphous Dasatinib does not involve the usage of special technologies like spray drying, ball milling and etc.

The dasatinib process impurities well controlled by the present invention in a cost effective manner are as below.

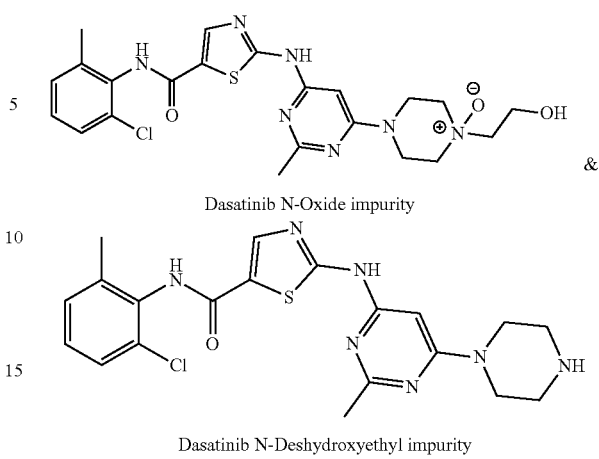

Dasatinib N-Oxide impurity

&

Dasatinib N-Deshydroxyethyl impurity

BRIEF DESCRIPTION OF THE FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure wherein.

Figure 1:
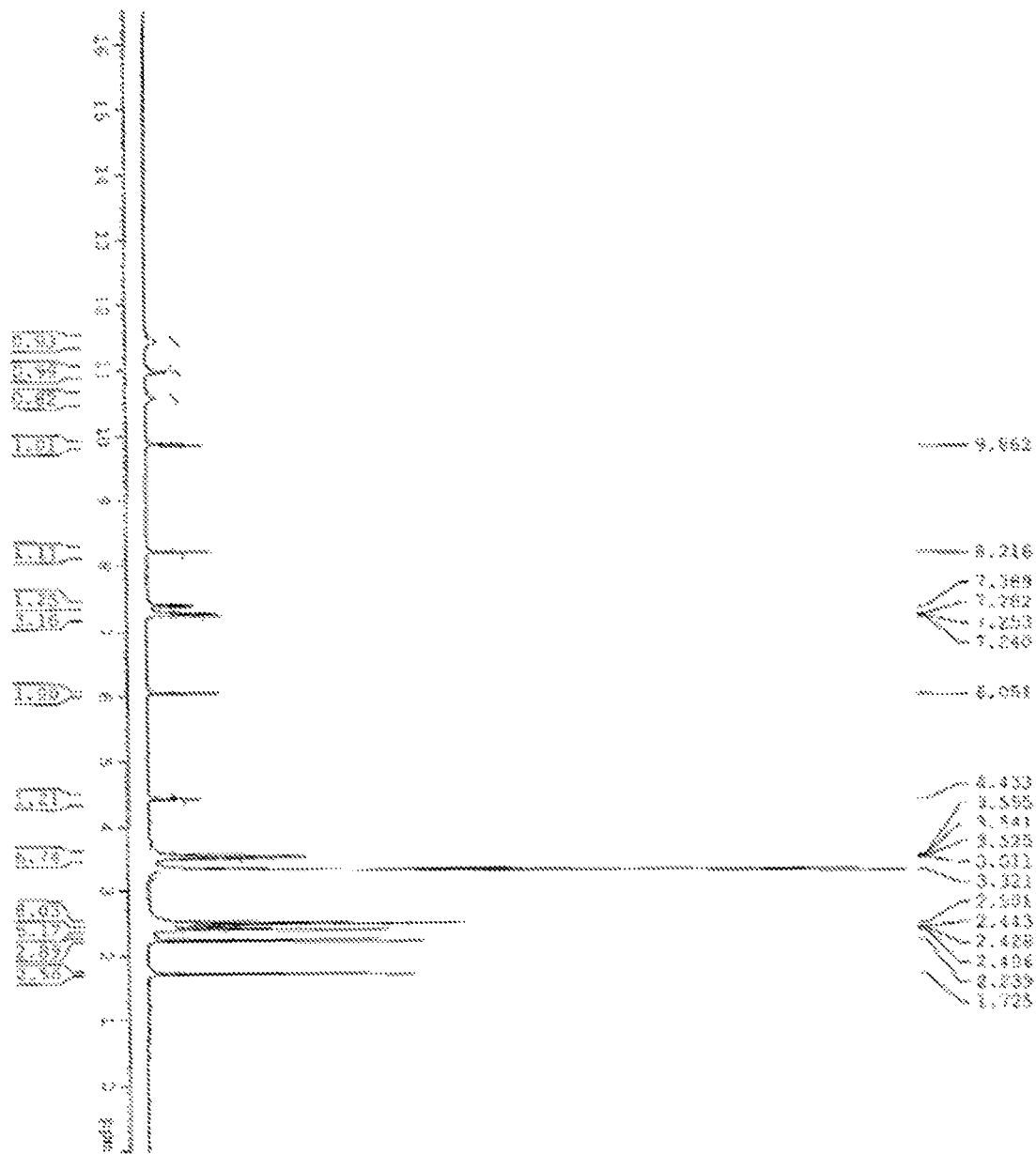
FIG. 1: Illustrates the $^1$H NMR pattern of the crystalline Dasatinib-Thymine co-crystal of Formula Ia.
Figure 2:
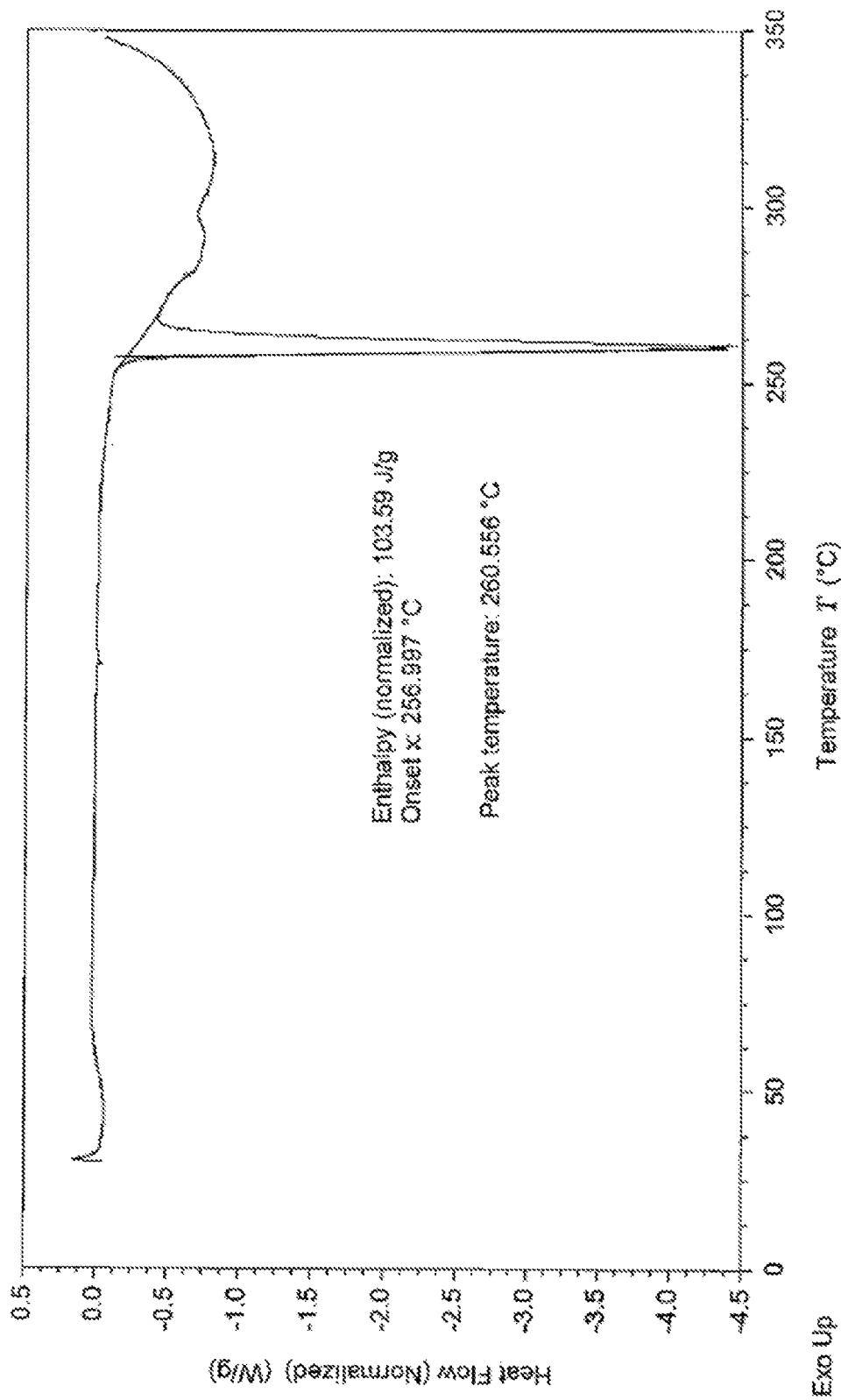
FIG. 2: Illustrates the DSC thermogram of the crystalline Dasatinib-Thymine co-crystal of Formula Ia.
Figure 3:
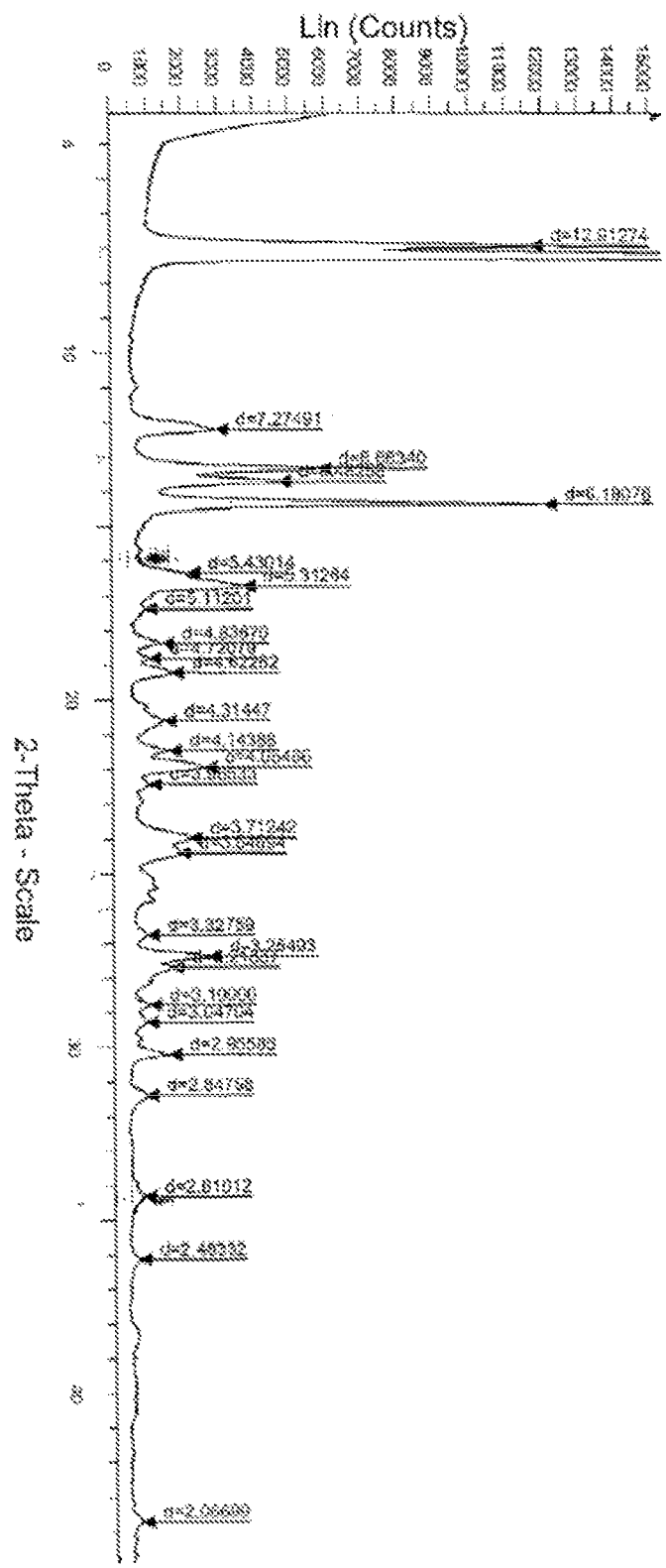
FIG. 3: Illustrates the PXRD of crystalline the Dasatinib-Thymine co-crystal of Formula Ia.
Figure 4:
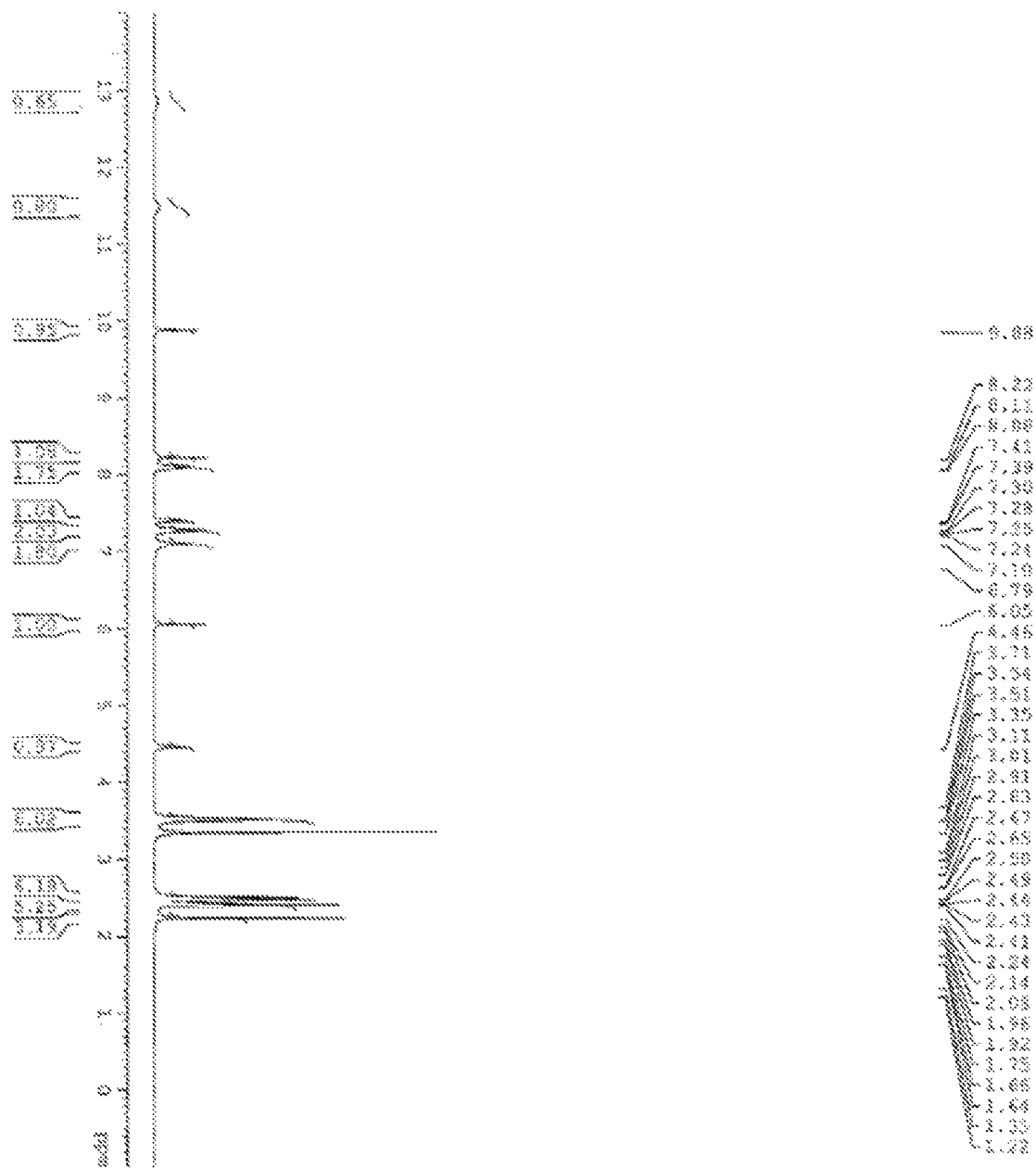
FIG. 4: Illustrates the $^1$H NMR pattern of the crystalline Dasatinib-Adenine co-crystal of Formula Ib.
Figure 5:
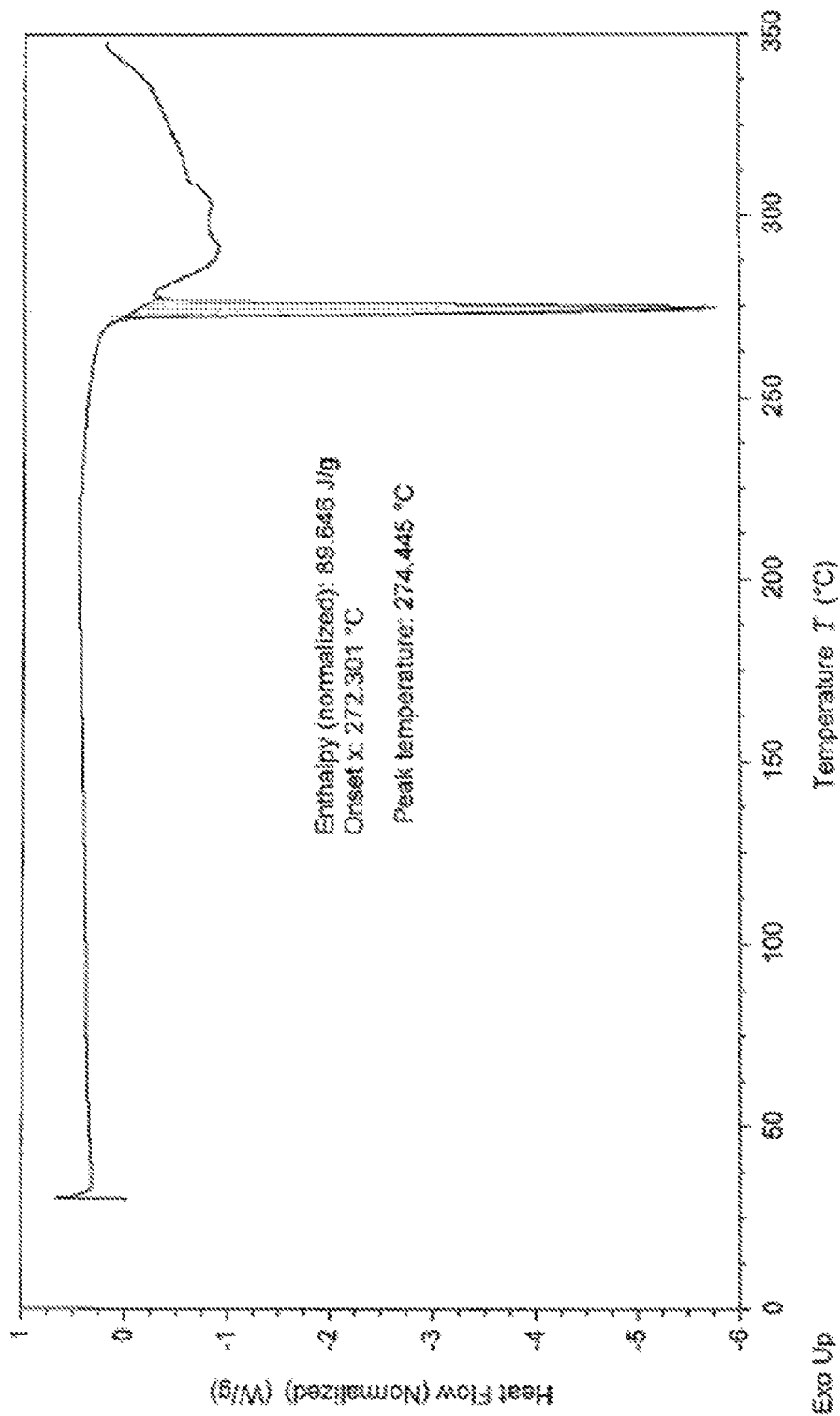
FIG. 5: Illustrates the DSC thermogram of the crystalline Dasatinib-Adenine co-crystal of Formula Ib.
Figure 6:
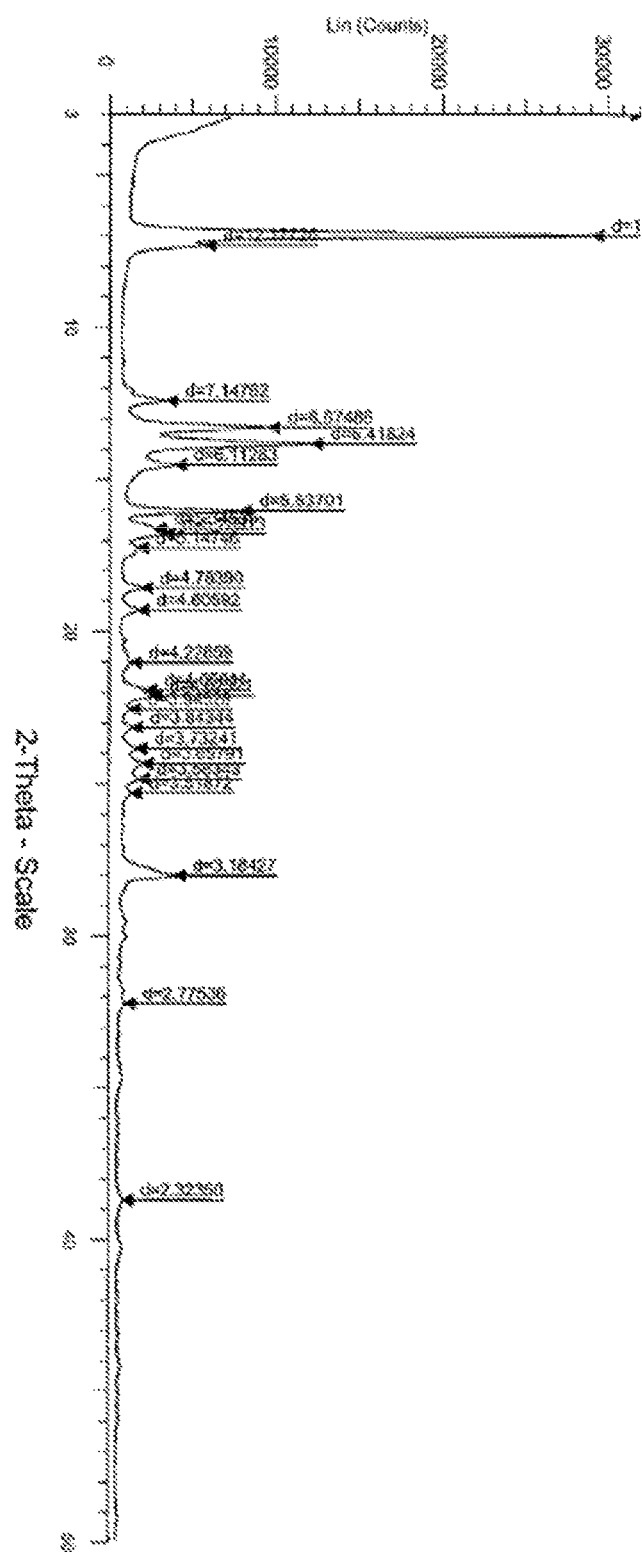
FIG. 6: Illustrates the PXRD of crystalline the Dasatinib-Adenine co-crystal of Formula Ib.
Figure 7:
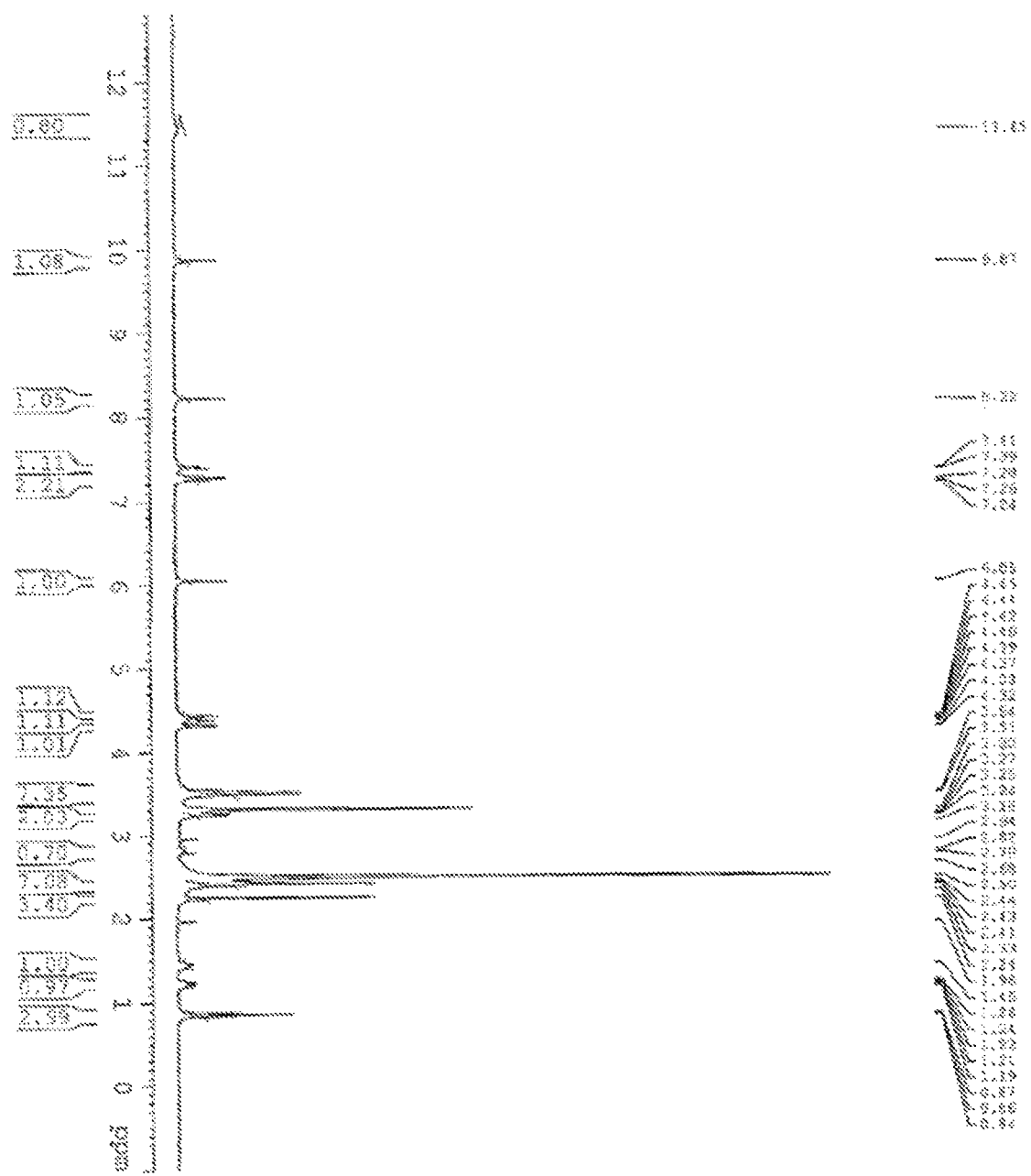
FIG. 7: Illustrates the $^1$H NMR pattern of the crystalline Dasatinib-(±)-1,2-Butanediol solvate of Formula Ic.
Figure 8:
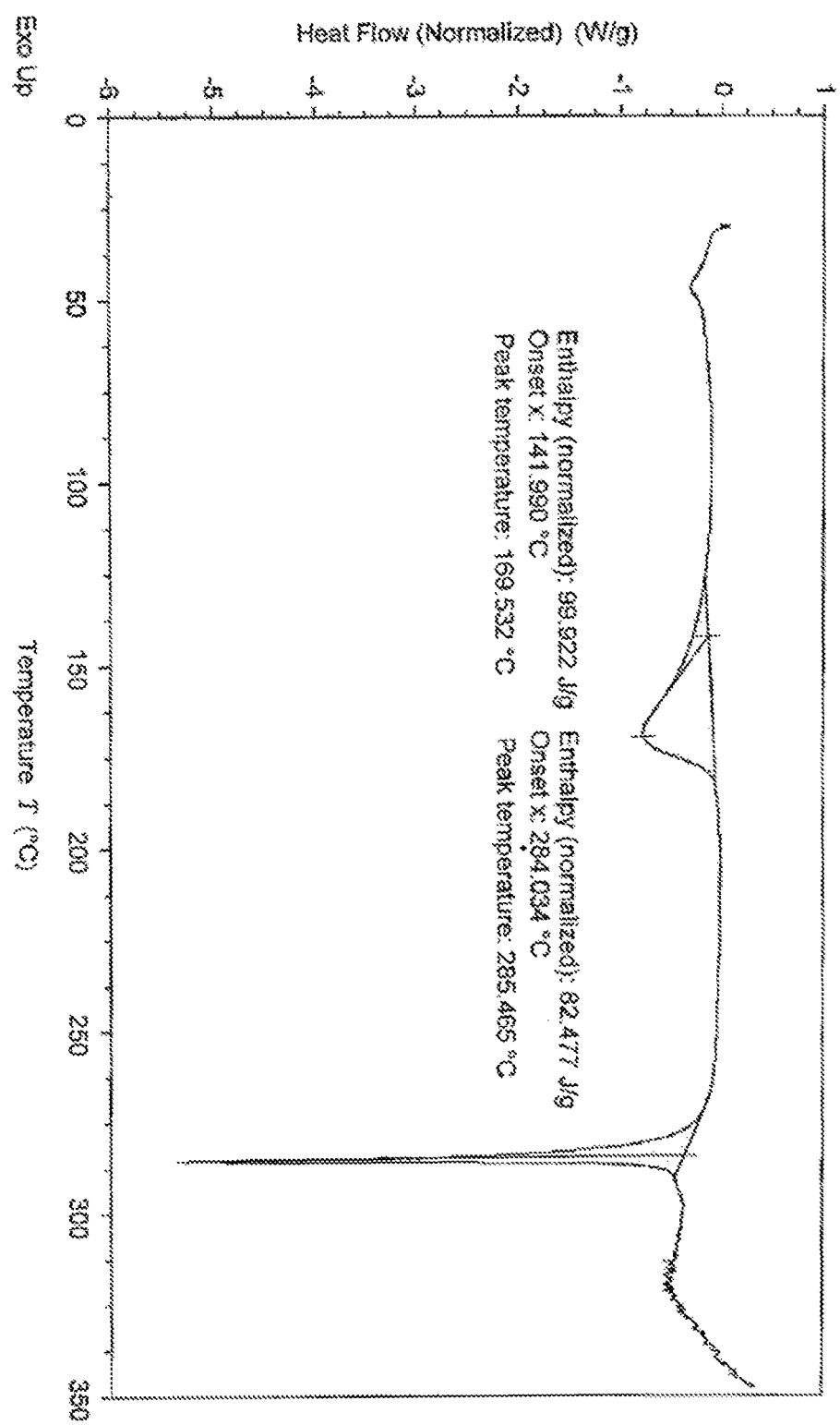
FIG. 8: Illustrates the DSC thermogram of the crystalline Dasatinib-(±)-1,2-Butanediol solvate of Formula Ic.
Figure 9:
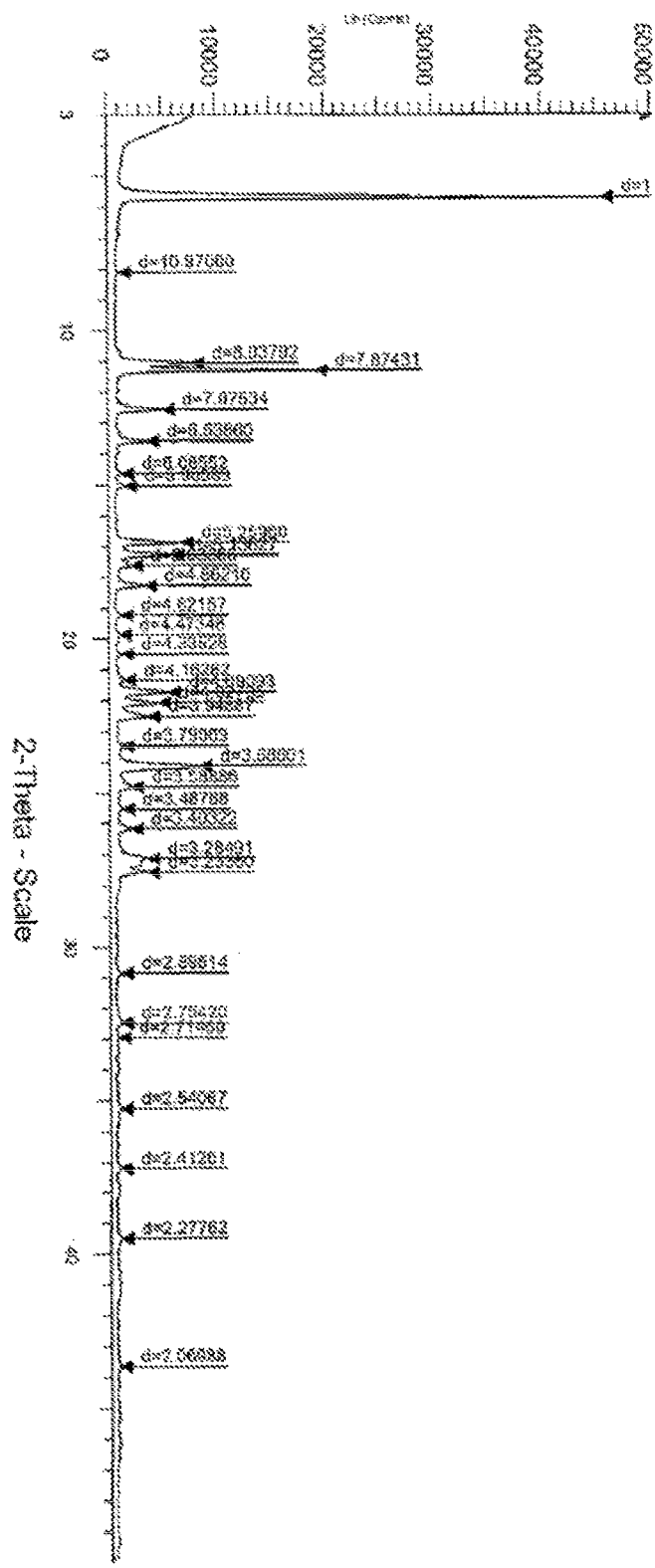
FIG. 9: Illustrates the PXRD of crystalline the Dasatinib-(±)-1,2-Butanediol solvate of Formula Ic.
Figure 10:
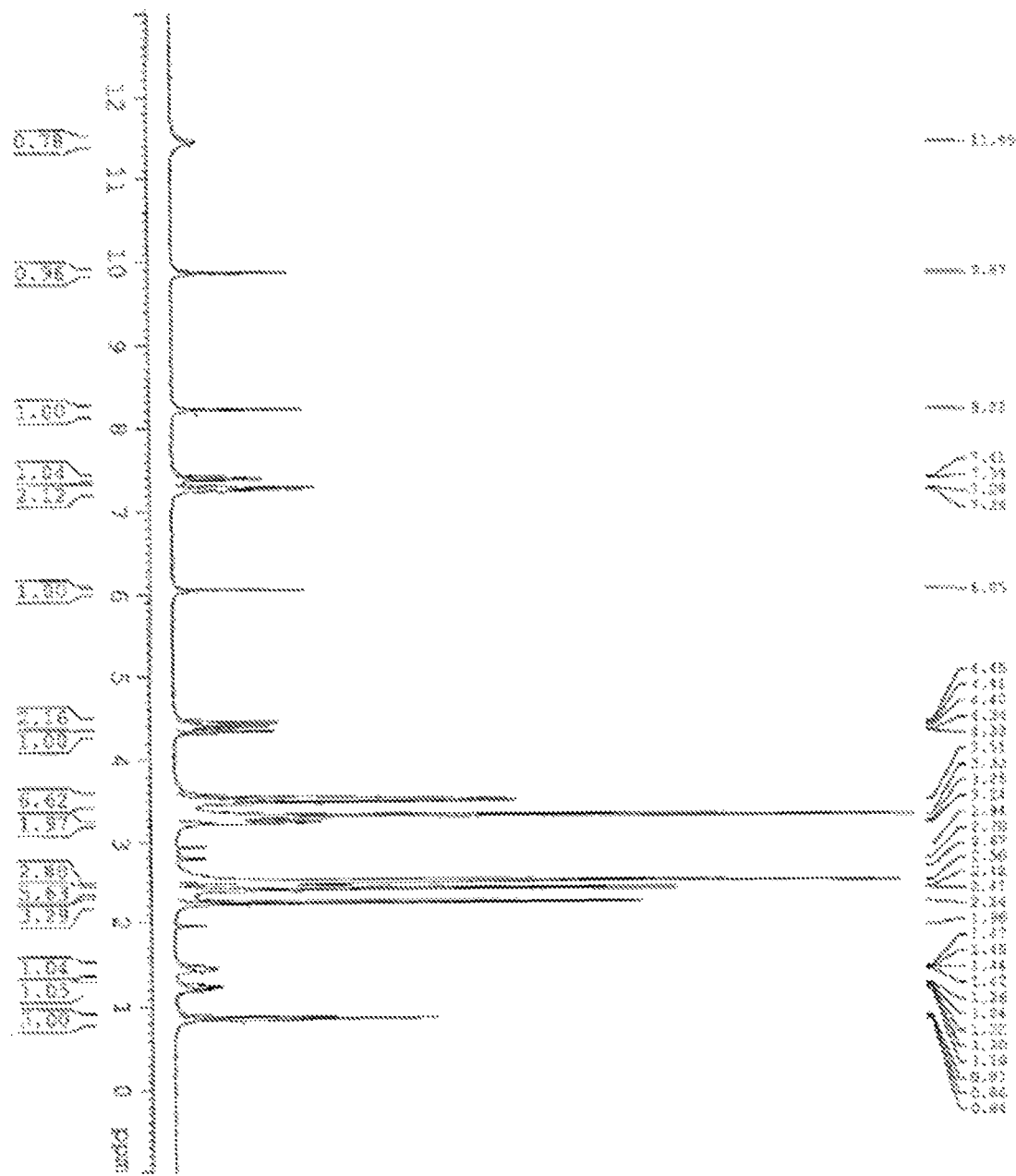
FIG. 10: Illustrates the $^1$H NMR pattern of the crystalline Dasatinib-(R)-1,2-Butanediol solvate of Formula Id.
Figure 11:
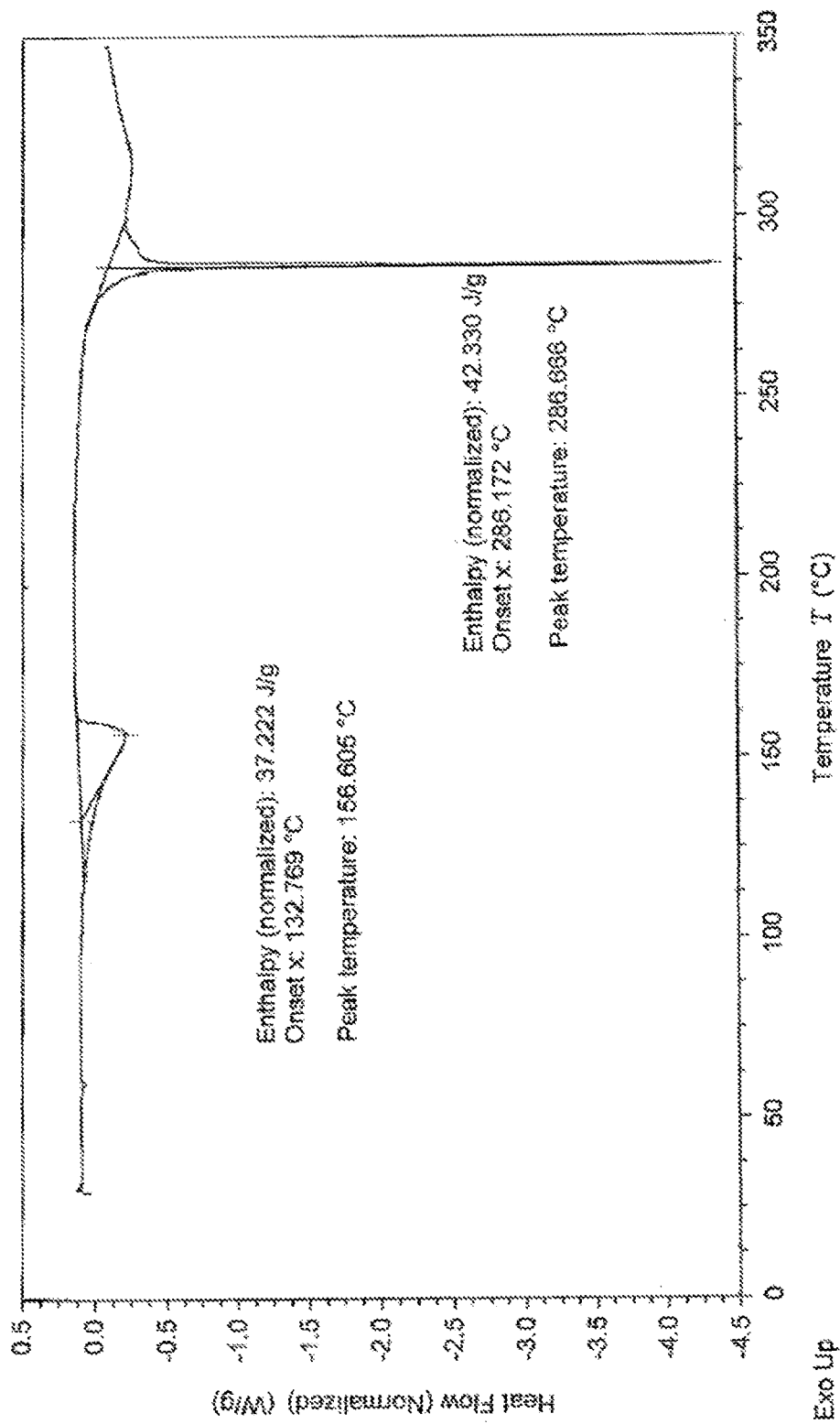
FIG. 11: Illustrates the DSC thermogram of the crystalline Dasatinib-(R)-1,2-Butanediol solvate of Formula Id.
Figure 12:
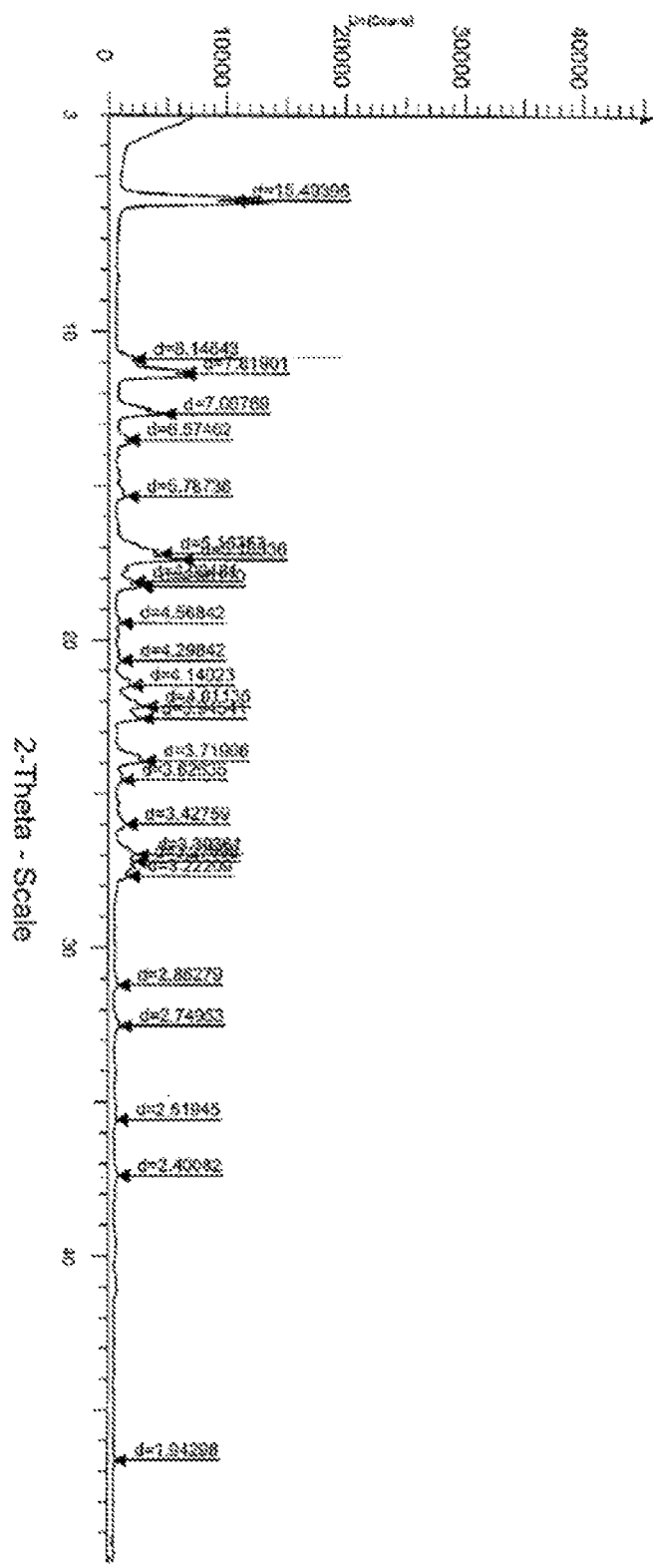
FIG. 12: Illustrates the PXRD of the crystalline Dasatinib-(R)-1,2-Butanediol solvate of Formula Id.
Figure 13:
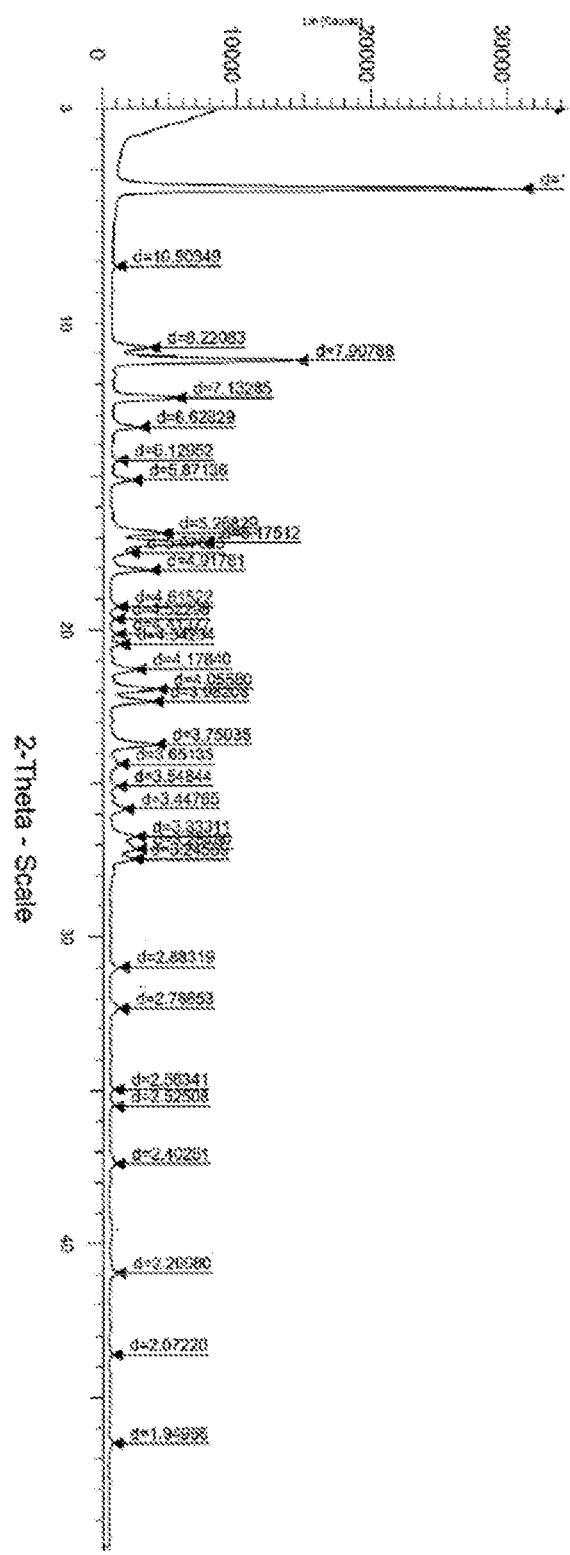
FIG. 13: Illustrates the PXRD of the crystalline Dasatinib-(S)-1,2-Butanediol solvate of Formula Ie.
Figure 14:
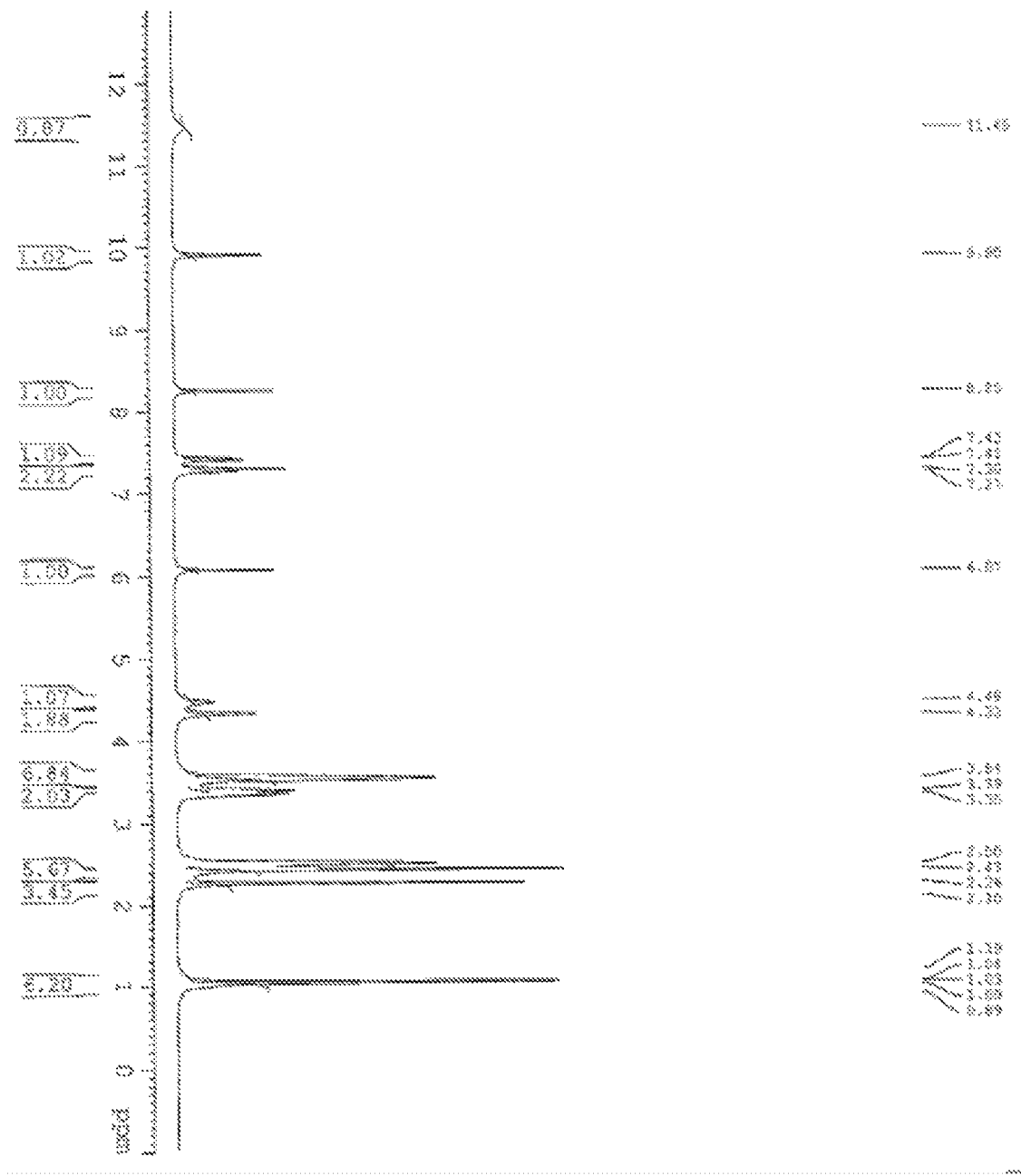
FIG. 14: Illustrates the $^1$H NMR pattern of the crystalline Dasatinib-(±)-2,3-Butanediol solvate of Formula Ig.
Figure 15:
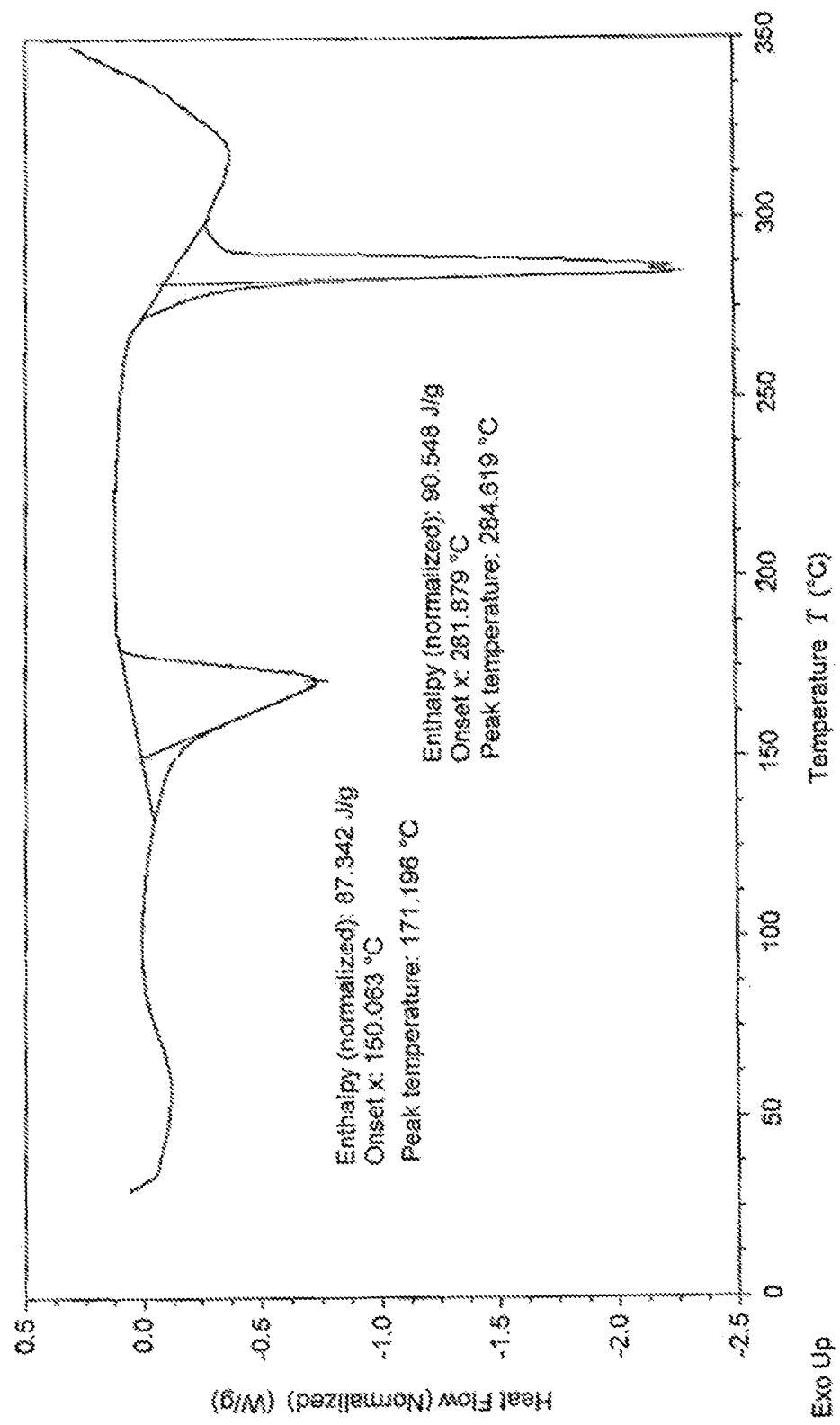
FIG. 15: Illustrates the DSC thermogram of the crystalline Dasatinib-(±)-2,3-Butanediol solvate of Formula Ig.
Figure 16:
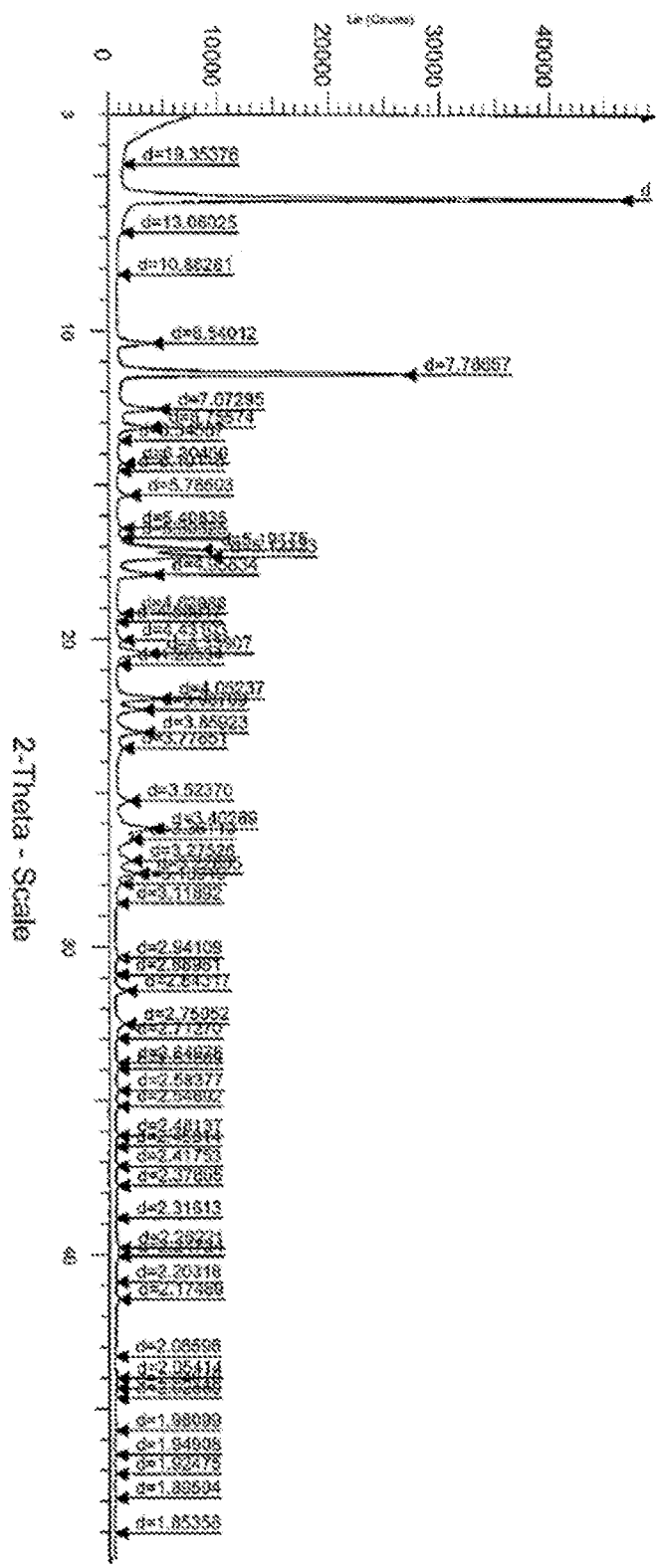
FIG. 16: Illustrates the PXRD of crystalline the Dasatinib-(±)-2,3-Butanediol solvate of Formula Ig.
Figure 17:
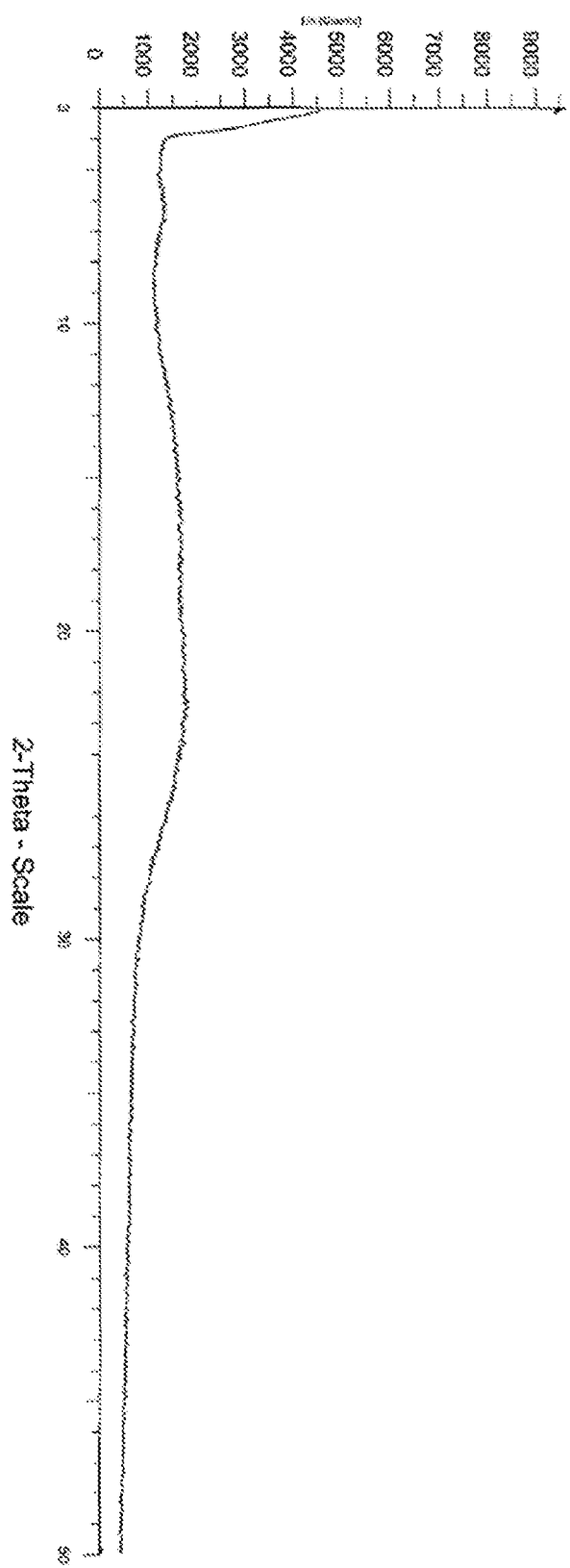
FIG. 17: Illustrates the PXRD of amorphous Dasatinib.

The method of analysis of the compounds represented in the figures as above are as below:

PXRD Analysis

About 300 mg of powder sample was taken onto the sample holder and was tightly packed on the sample holder uniformly by means of glass slide and Powder X-ray diffraction was recorded on Bruker D8 Advance diffractometer (Bruker-AXS, Karlsruhe, Germany) using Cu-Kα X-radiation ($\lambda$=1.5406 Å) at 40 kV and 30 mA powder. X-ray diffraction patterns were collected over the 2θ range 3-50° at a scan rate of 1°/min.

DSC Analysis

DSC was performed on a Mettler Toledo DSC 822e module. 4-6 mg of sample was placed in crimped but vented aluminium sample pans. The temperature range was from 30-250° C. @ 10° C./min. Samples were purged by a stream of nitrogen flowing at 80 mL/min.

IR Analysis

IR was performed on a Fisher Scientific (NICOLET-iS50-FTIR). About 5 mg of sample was spread over the region of diamond ATR sampling station and collected the sample spectrum between 4000 cm−1 to 400 cm−1 to obtain a spectrum of suitable intensity (above 60% transmission at 2000 cm−1).

DETAILED DESCRIPTION OF THE INVENTION

The embodiments of the present invention are further described using specific examples herein after. The examples are provided for better understanding of certain embodiments of the invention and not, in any manner, to limit the scope thereof. Possible modifications and equivalents apparent to those skilled in the art using the teachings of the present description and the general art in the field of the invention shall also form the part of this specification and are intended to be included within the scope of it.

Schemes:

Scheme-1
Preparation of Dasatinib-co-crystals of Formula B from Formula II
(using DMAc and Methanol as the solvents) One-pot synthesis

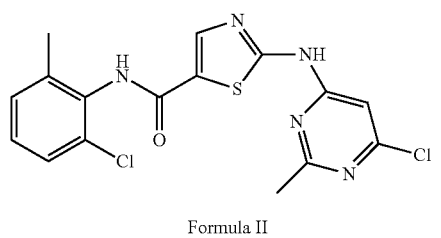

Formula II

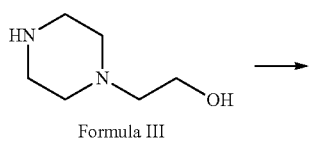

Formula III

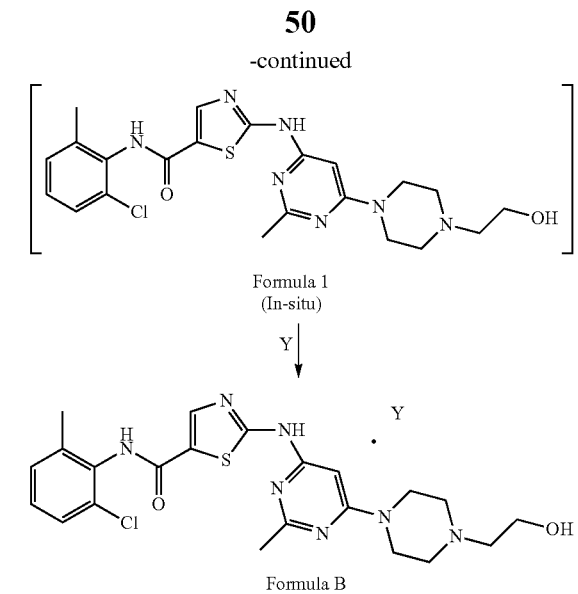

Wherein, Y is Thymine or Adenine
Formula Ia = Co-crystal of Formula I with Thymine
Formula Ib = Co-crystal of Formula I with Adenine General procedure: To a glass vessel equipped with a stirrer, condenser and a thermometer probe were added the Formula II, Formula III and a suitable first organic solvent and the mass was heated to suitable temperature. The resulting reaction mass (containing Formula I) was cooled and a co-former selected from Thymine or Adenine was added to the reaction mass. A suitable second organic solvent was added to the reaction mass at constant rate under stirring. The mass was heated to a suitable temperature and the resulting suspension was maintained at the same temperature under stirring. The mass was cooled and Water was added to the reaction mass at a constant rate under stirring. The reaction mass was maintained at 25±5° C. The mass was filtered and the solid was washed, suck dried and dried under vacuum to obtain Dasatinib-co-crystal of Formula B as a crystalline solid.

Example 1a: Preparation of Dasatinib-Thymine Co-Crystal of Formula Ia from Formula II (Using DMAc and Methanol as the Solvents) One-Pot Synthesis

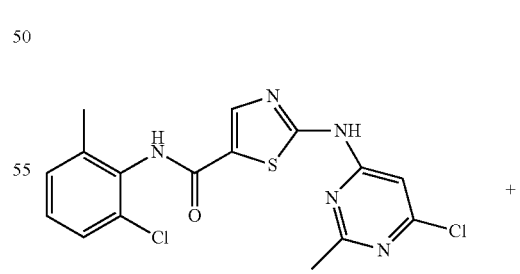

Formula II

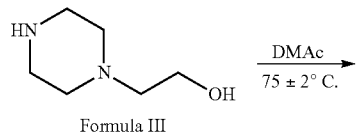

Formula III

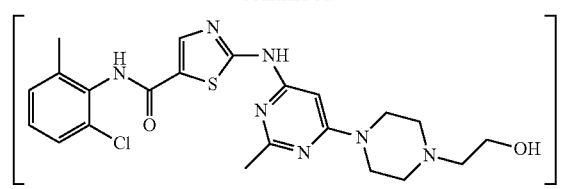

Formula I
(In-situ)

Thymine
Methanol
60 ± 2° C.
Water

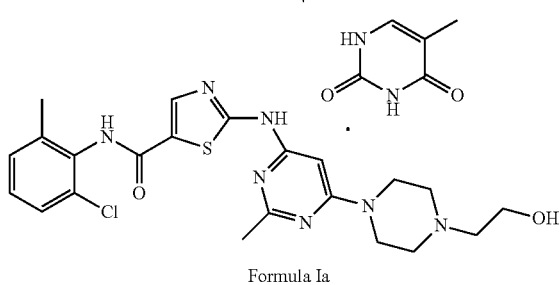

Formula Ia

To a 100 mL glass vessel equipped with a stirrer, condenser and a thermometer probe were added the Formula II (2.00 g, 0.0051 mol, 1.00 equiv.), Formula III (6.00 mL, 3.00 vol) and N,N-dimethyl acetamide (2.00 mL, 1.00 vol) and the mass was heated to 75±2° C. The reaction mass was maintained at 75±2° C. under stirring. The resulting reaction mass (containing Formula I) was cooled to 25±5° C. and Thymine (0.96 g, 0.007 mol, 1.50 equiv.) was added to the reaction mass at 25±5° C. under stirring. Methanol (60.0 mL, 30.0 vol) was added to the reaction mass at constant rate at 25±5° C. under stirring. The mass was heated to 60±2° C. and the resulting suspension was maintained at the same temperature under stirring. The mass was cooled to 25±5° C. and maintained at the same temperature. Water (15 mL, 7.50 vol) was added to the reaction mass at a constant rate under stirring. The reaction mass was maintained at 25±5° C. The mass was filtered and the solid was washed with Methanol (10.0 mL, 5.00 vol), suck dried and dried at 50±5° C. under vacuum to obtain Dasatinib-Thymine co-crystal of Formula Ia as a crystalline solid.

Example-1b: Preparation of Dasatinib-Adenine Co-Crystal of Formula Ib from Formula II (Using DMAc and Methanol as the Solvents)—One-Pot Synthesis

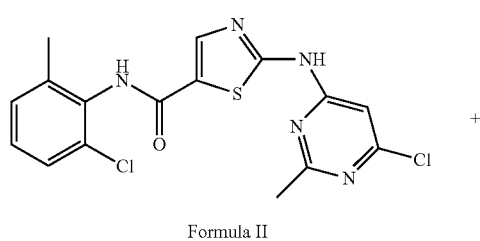

Formula II

+

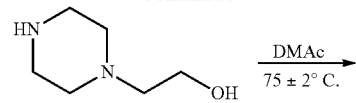

Formula III

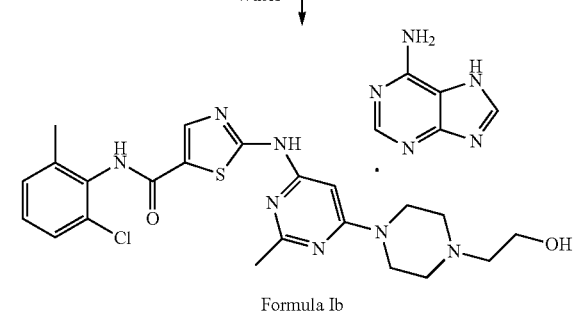

Formula I
(In-situ)

Adenine
Methanol
60 ± 2° C.
Water

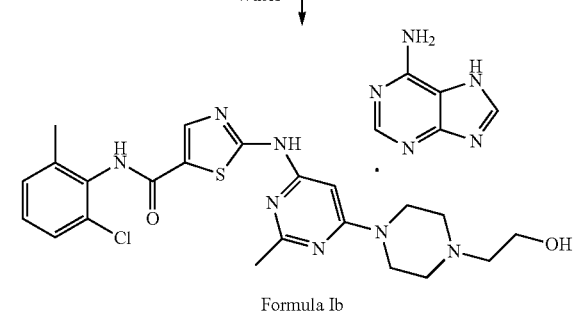

Formula Ib

To a 500 mL glass vessel equipped with a stirrer, condenser and a thermometer probe were added the Formula II (10.0 g, 0.0254 mol, 1.00 equiv.), Formula III (30.0 mL, 3.00 vol) and N, N-dimethyl acetamide (10.0 mL, 1.00 vol) and the mass was heated to 75±5° C. The reaction mass was maintained at 75±5° C. under stirring. The reaction mass was cooled to 25±5° C. and Adenine (5.14 g, 0.038 mol, 1.50 equiv.) was added to the reaction mass at 25±5° C. under stirring. Methanol (300 mL, 30.0 vol) was added to the reaction mass at constant rate at 25±5° C. under stirring. The mass was heated to 60±2° C. and the resulting suspension was maintained at the same temperature under stirring. The mass was cooled to 25±5° C. and maintained at the same temperature. Water (130 mL, 13.0 vol) was added to the reaction mass at a constant rate under stirring. The reaction mass was maintained at 25±5° C. The mass was filtered and the solid was washed with Methanol (70.0 mL, 7.00 vol), suck dried and dried at 50±5° C. under vacuum to obtain Dasatinib-Adenine co-crystal of Formula Ib as a crystalline solid.

Example-1c

To a 3 L glass vessel equipped with a stirrer, condenser and a thermometer probe were added the Formula II (50.0 g, 0.127 mol, 1.00 equiv.), Formula III (150 mL, 3.00 vol) and N,N-dimethyl acetamide (50.0 mL, 1.00 vol) and the mass was heated to 75±5° C. The reaction mass was maintained at 75±5° C. under stirring. The reaction mass was cooled to 25±5° C. and Adenine (25.7 g, 0.190 mol, 1.50 equiv.) was added to the reaction mass at 25±5° C. under stirring. Methanol (1500 mL, 30.0 vol) was added to the reaction mass at constant rate at 25±5° C. under stirring. The mass was heated to 60±2° C. and the resulting suspension was maintained at the same temperature under stirring. The mass was cooled to 25±5° C. and maintained at the same temperature. Water (650 mL, 13.0 vol) was added to the reaction mass at a constant rate under stirring. The reaction mass was maintained at 25±5° C. The mass was filtered and the solid was washed with Methanol (350 mL, 7.00 vol), suck dried and dried at 50±5° C. under vacuum to obtain Dasatinib-Adenine co-crystal of Formula Ib as a crystalline solid.

Scheme-2
Preparation of Dasatinib-co-crystal of Formula B from Formula II
(using wet Dasatinib)

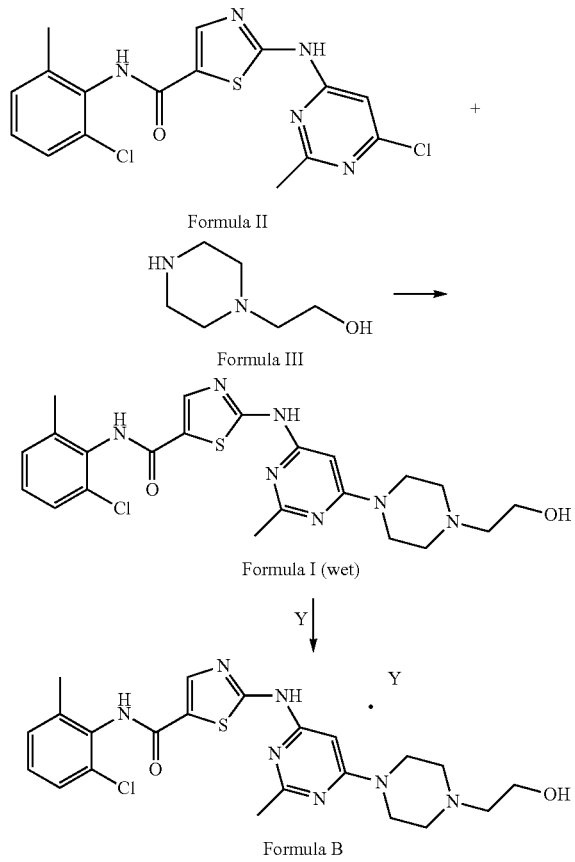

Wherein, Y is Thymine or Adenine
Formula Ia = Co-crystal of Formula I with Thymine
Formula Ib = Co-crystal of Formula I with Adenine To a glass vessel equipped with a stirrer, condenser and a thermometer probe were added the Formula II, Formula III and a suitable first organic solvent and the mass was heated to a suitable temperature. The reaction mass was cooled and a suitable second organic solvent was added at a constant rate under stirring. The mass was filtered. Formula I (wet), was charged into a glass vessel equipped with a stirrer, condenser and a thermometer probe. Co-former selected from Thymine or adenine was added. The mass was heated to a suitable temperature and the resulting suspension was maintained at the same temperature under stirring. The mass was cooled and Water was added to the reaction mass at a constant rate under stirring. The mass was filtered and the solid was washed with Methanol, suck dried and dried under vacuum to obtain Dasatinib-co-crystal of Formula B as a crystalline solid.

Example 2a: Preparation of Dasatinib-Thymine
Co-Crystal of Formula Ia from Formula II (Using
Wet Dasatinib)

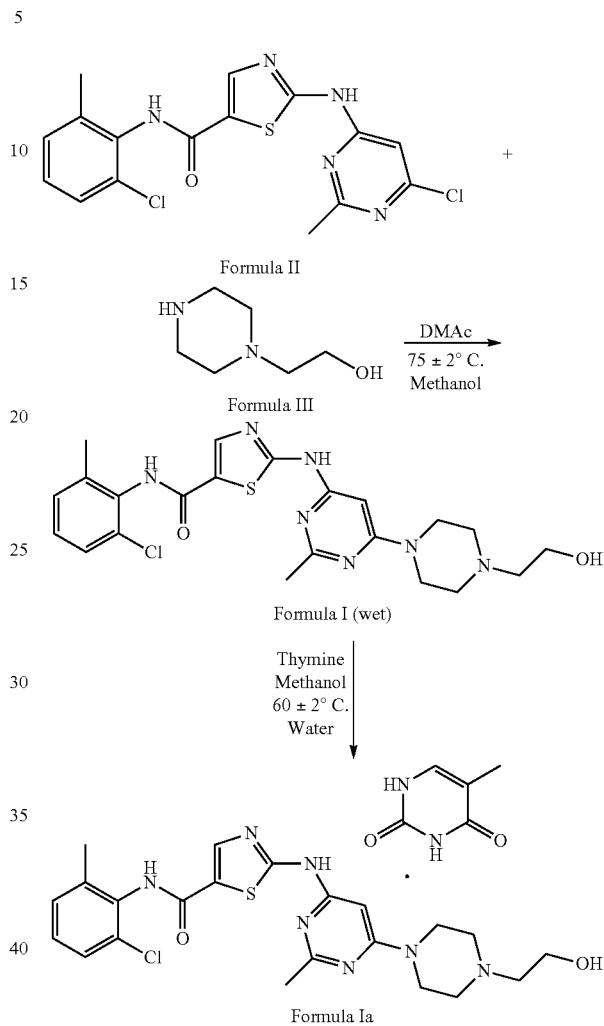

To a 100 mL glass vessel equipped with a stirrer, condenser and a thermometer probe were added the Formula II (2.00 g, 0.0051 mol, 1.00 equiv.), Formula III (6.00 mL, 3.00 vol) and N,N-dimethyl acetamide (2.00 mL, 1.00 vol) and the mass was heated to 752° C. The reaction mass was maintained at 75*2° C. under stirring. The reaction mass was cooled to 25±5° C. and Methanol (50.0 mL, 25.0 vol) was added at a constant rate under stirring. The resulting slurry was stirred at 25±5° C. The mass was filtered and the solid was washed with Methanol (10.0 mL, 5.00 vol). Formula I (wet) (2.00 g, 0.0041 mol), was charged into a 100 mL glass vessel equipped with a stirrer, condenser and a thermometer probe. Thymine (0.77 g, 0.006 mol, 1.50 equiv.) and Methanol (60.0 mL, 30.0 vol) were added at 25±5° C. The mass was heated to 60±2° C. and the resulting suspension was maintained at the same temperature under stirring. The mass was cooled to 25±5° C. and maintained at the same temperature. Water (15 mL, 7.50 vol) was added to the reaction mass at a constant rate under stirring. The reaction mass was maintained at 25±5° C. The mass was filtered and the solid was washed with Methanol (10.0 mL, 5.00 vol), suck dried and dried at 50±5° C. under vacuum to obtain Dasatinib-Thymine co-crystal of Formula Ia as a crystalline solid.

Scheme-3
Preparation of Dasatinib-co-crystal of Formula B from Formula II
(using Methanol as the solvent) One-pot synthesis

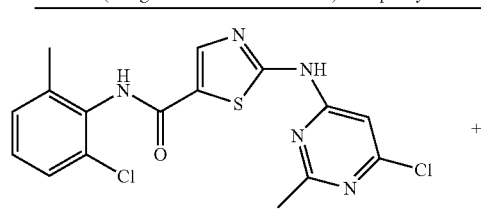

Formula II

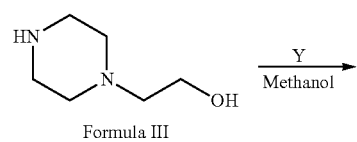

Formula III

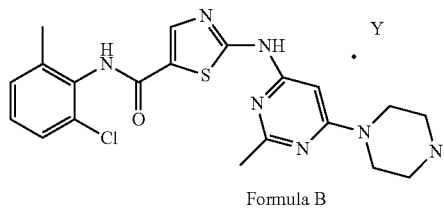

Formula B

Wherein, Y is Thymine or Adenine
Formula Ia = Co-crystal of Formula I with Thymine
Formula Ib = Co-crystal of Formula I with Adenine To a glass vessel equipped with a stirrer, condenser and a thermometer probe were added the Formula II, Formula III, a suitable coformer selected from Thymine or adenine and Methanol. The reaction mass was heated to a suitable temperature. The mass was cooled and filtered and the solid was washed with Methanol, suck dried and dried under vacuum to obtain Dasatinib-co-crystal of Formula B as a crystalline solid.

Example 3a: Preparation of Dasatinib-Thymine Co-Crystal of Formula Ia from Formula II (Using Methanol as the Solvent) One-Pot Synthesis

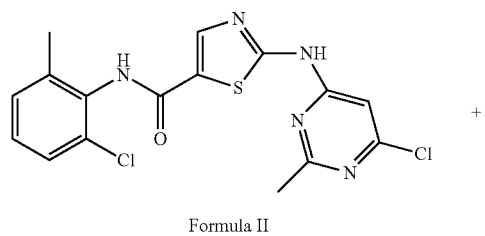

Formula II

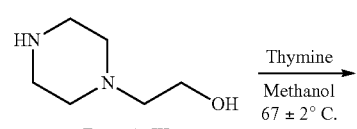

Formula III

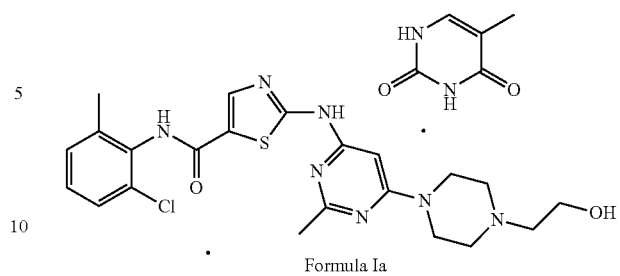

Formula Ia

To a 1 L glass vessel equipped with a stirrer, condenser and a thermometer probe were added the Formula II (50.0 g, 0.127 mol, 1.00 equiv.), Formula III (200 mL, 4.00 vol), Thymine (15.99 g, 0.127 mol, 1.00 equiv.) and Methanol (300 mL, 6.00 vol). The reaction mass was heated to 67±2° C. The reaction mass was maintained at 65±2° C. under stirring. After completion of the reaction, Methanol (200 mL, 4.00 vol) was added to the reaction mass at constant rate. The reaction mass was maintained at the same temperature under stirring. The mass was cooled to 25±5° C. and maintained at the same temperature. The mass was filtered and the solid was washed with Methanol (250 mL, 5.00 vol), suck dried and dried at 505° C. under vacuum to obtain Dasatinib-Thymine co-crystal of Formula Ia as a crystalline solid (57.5 g, 91.38% w.r.t Formula II, 99.91% AUC, N-Oxide impurity: <0.15% AUC, N-Deshydroxyethyl impurity: <0.15% AUC).

Scheme-4
Preparation of Dasatinib-butane diol solvates of
Formula Ic, Id, Ie & Ig from Anhydrous Dasatinib
(using Butanediol as the solvent) - One-pot synthesis

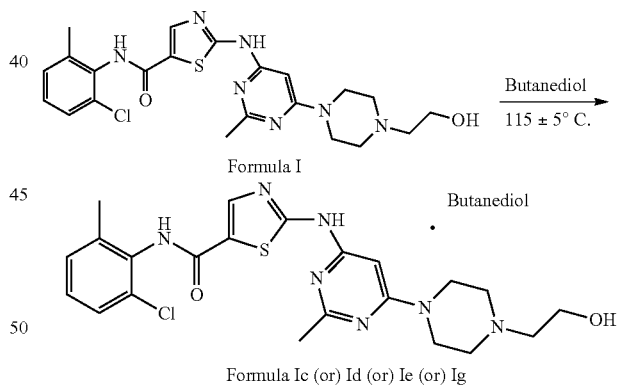

Formula Ic (or) Id (or) Ie (or) Ig

Wherein, Butanediol = (±)-1,2-butanediol or (R)-1,2-butanediol or (S)-1,2-butanediol or (±)-2,3-butanediol
Formula Ic = (±)-1,2-butanediol solvate of Formula I
Formula Id = (R)-1,2-butanediol solvate of Formula I
Formula Ie = (S)-1,2-butanediol solvate of Formula I
Formula Ig = (±)-2,3-butanediol solvate of Formula I To a glass vessel equipped with a stirrer, condenser and a thermometer probe were added the Formula I, and Butanediol and the mass was heated to 115±5° C. The reaction mass was maintained at 115±5° C. under stirring. The reaction mass was cooled to 60±5° C. and maintained at the same temperature. The mass was filtered and dried under vacuum to obtain Dasatinib-Butanediol solvate of Formula Ic or Id or Ie or Ig as a crystalline solid.

Example 4a: Preparation of Crystalline Dasatinib-(±)-1,2-Butanediol Solvate of Formula Ic from Anhydrous Dasatinib To a 50 mL glass vessel equipped with a stirrer, condenser and a thermometer probe were added the Formula I (1.00 g, 0.002 mol), and (±)-1,2-Butanediol (10.0 mL, 10.0 vol) and the mass was heated to 115±5° C. The reaction mass was maintained at 115±5° C. under stirring. The reaction mass was cooled to 60±5° C. and maintained at the same temperature. The mass was filtered and dried under vacuum to obtain Dasatinib-(±)-1,2-Butanediol solvate of Formula Ic as a crystalline solid.

Example 4b: Preparation of Crystalline Dasatinib-(R)-1, 2-Butanediol Solvate of Formula Id from Anhydrous Dasatinib To a 50 mL glass vessel equipped with a stirrer, condenser and a thermometer probe were added the Formula I (1.00 g, 0.002 mol), and (R)-1, 2-Butanediol (10.0 mL, 10.0 vol) and the mass was heated to 115±5° C. The reaction mass was maintained at 115±5° C. under stirring. The reaction mass was cooled to 60±5° C. and maintained at the same temperature. The mass was filtered and dried under vacuum to obtain Dasatinib-(R)-1, 2-Butanediol solvate of Formula Id as a crystalline solid.

Example 4c: Preparation of Crystalline Dasatinib-(±)-2,3-Butanediol Solvate of Formula Ig from Anhydrous Dasatinib To a 50 mL glass vessel equipped with a stirrer, condenser and a thermometer probe were added the Formula I (2.00 g, 0.0021 mole, 1.00 equiv.), and (±)-2,3-butanediol (15.0 mL, 15.0 vol) and the mass was heated to 115±5° C. The reaction mass was maintained at 115±5° C. under stirring for 1 to 2 h (Clear solution). The reaction mass was cooled to 60±5° C. and maintained at the same temperature for 3 to 4 h. The mass was filtered and dried under vacuum for 10-15 h to obtain Dasatinib-2, 3-butanediol solvate of Formula Ig as a crystalline solid.

Scheme-5
Preparation of Dasatinib-butanediol solvates of Formula Ic, Id, Ie and Ig from Formula II (using DIPEA and Butanediol as the solvent) - One-pot synthesis

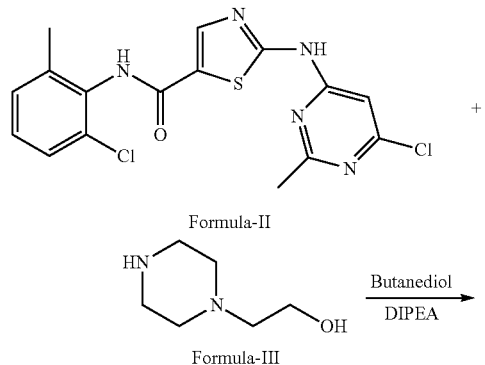

Formula-II

Formula-III

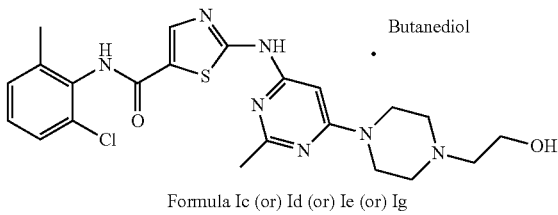

Formula Ic (or) Id (or) Ie (or) Ig

Wherein, Butanediol = (±)-1,2-butanediol or (R)-1,2-butanediol or (S)-1,2-butanediol or (±)-2,3-butanediol
Formula Ic = (±)-1,2-butanediol solvate
Formula Id = (R)-1,2-butanediol solvate
Formula Ie = (S)-1,2-butanediol solvate
Formula Ig = (±)-2,3-butanediol solvate To a glass vessel equipped with a stirrer, condenser and a thermometer probe were added the Formula-II, Formula-III, N,N-Diisopropyl ethyl amine and Butanediol was added and the mass was heated to a suitable temperature. The mass was cooled and filtered. The solid was washed, suck dried under vacuum to obtain Dasatinib-Butanediol solvate of Formula-Ic or Id or Ie or Ig as a crystalline solid.

Example 5a: Preparation of Crystalline Dasatinib-(S)-1,2-Butanediol Solvate of Formula Ie from Formula II (Using DIPEA and Butanediol as the Solvent)—One-Pot Synthesis To a 5 L glass vessel equipped with a stirrer, condenser and a thermometer probe were added the Formula-II (300.0 g, 0.7608 mol.), Formula-III (300 mL, 1.00 vol), N,N-Diisopropyl ethyl amine (688 g, 5.32 mol) and (S)-1,2-Butanediol (1500 mL, 5.00 vol) was added and the mass was heated to 115±5° C. The reaction mass was maintained at 115±5° C. under stirring for 13 to 15 h. The mass was cooled to 60±5° C. and maintained at the same temperature for 1 to 2 h. The mass was filtered and the solid was washed with Diisopropyl ether (1500 mL, 5.00 vol), suck dried under vacuum for 1-2 h and material was dried at 40° C. under vacuum for 12-15 h to obtain Dasatinib-(S)-1,2-Butanediol solvate of Formula-Ie as a crystalline solid.

Scheme-6
Preparation of Dasatinib-Butanediol solvates of Formula Ic, Id, Ie and Ig from Formula II (using Butanediol and DMAc as the solvents) - One-pot synthesis

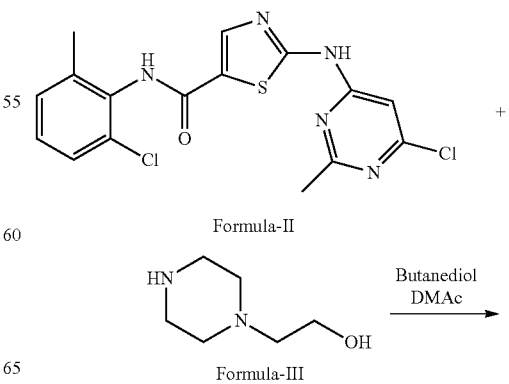

Formula-II

Formula-III

-continued

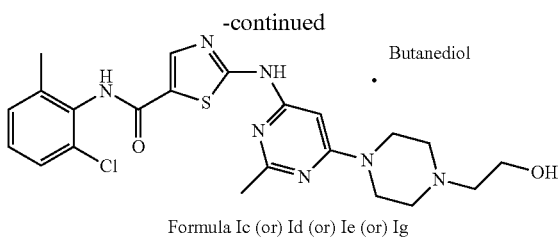

Formula Ic (or) Id (or) Ie (or) Ig

Wherein, Butanediol = (±)-1,2-butanediol or (R)-1,2-butanediol or (S)-1,2-butanediol or (±)-2,3-butanediol
Formula Ic = (±)-1,2-butanediol solvate
Formula Id = (R)-1,2-butanediol solvate
Formula Ie = (S)-1,2-butanediol solvate
Formula Ig = (±)-2,3-butanediol solvate To a glass vessel equipped with a stirrer, condenser and a thermometer probe were added the Formula II, Formula III, N,N-dimethyl acetamide and Butanediol and the mass was heated to a suitable temperature. The reaction mass was cooled and Butanediol was added. The mass was heated again to a suitable temperature. The mass was cooled and filtered and the solid and dried under vacuum obtain Dasatinib-Butanediol solvate of Formula Ic or Id or Ie or Ig as a crystalline solid.

Example 6a: Preparation of Crystalline Dasatinib-(±)-1,2-Butanediol Solvate of Formula Ic from Formula II (One-Pot Synthesis)

To a 100 mL glass vessel equipped with a stirrer, condenser and a thermometer probe were added the Formula II (5.00 g, 0.0127 mol), Formula III (5.00 mL, 1.00 vol), N,N-dimethyl acetamide (2.50 mL, 0.50 vol) and (±)-1,2-Butanediol (5.00 mL, 1.00 vol) and the mass was heated to 115±5° C. The reaction mass was maintained at 115±5° C. under stirring. The reaction mass was cooled to 25±5° C. and (±)-1,2-Butanediol (20.0 mL, 4.00 vol) was added. The mass was heated to 115±5° C. and the resulting mass was maintained at the same temperature under stirring. The mass was cooled to 60±5° C. and maintained at the same temperature. The mass was filtered and the solid was washed with (±)-1,2-Butanediol (5.00 mL, 1.00 vol), dried under vacuum obtain Dasatinib-(±)-1,2-Butanediol solvate of Formula Ic as a crystalline solid.

Scheme-7
Preparation of Dasatinib-butanediol solvates of Formula Ic, Id, Ie and Ig from Formula II via in aitu Formula I (using DMAc and butane diols as the solvents)
One-pot synthesis

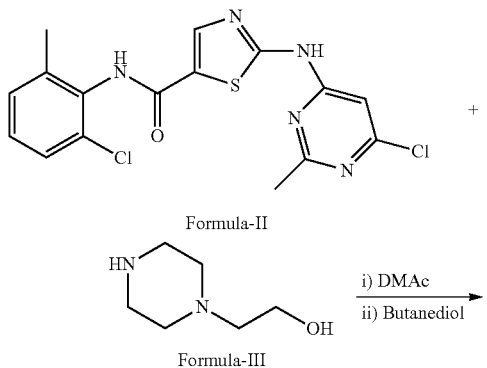

-continued

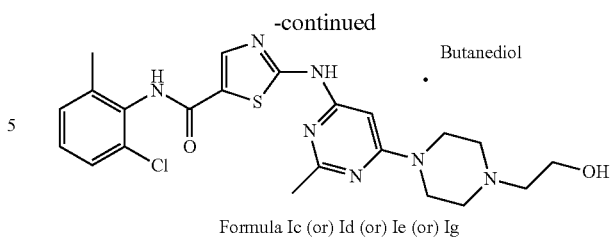

Formula Ic (or) Id (or) Ie (or) Ig

Wherein, Butanediol = (±)-1,2-butanediol or (R)-1,2-butanediol or (S)-1,2-butanediol or (±)-2,3-butanediol
Formula Ic = Dasatinib-(±)-1,2-butanediol solvate
Formula Id = Dasatinib-(R)-1,2-butanediol solvate
Formula Ie = Dasatinib-(S)-1,2-butanediol solvate
Formula Ig = Dasatinib-(±)-2,3-butanediol solvate To a glass vessel equipped with a stirrer, condenser and a thermometer probe were added the Formula II, Formula III, N,N-dimethyl acetamide and the mass was heated to a suitable temperature. (R)-1,2-Butanediol was added to the mass and the mass was heated to a suitable temperature. The mass was cooled, filtered and suck dried under vacuum to obtain Dasatinib-Butanediol solvate of Formula Ic or Id or Ie or Ig as a crystalline solid.

Example-7a: Preparation of Crystalline Dasatinib-(R)-1,2-Butanediol Solvate of Formula Id from Formula II (One-Pot Synthesis)

To a 50 mL glass vessel equipped with a stirrer, condenser and a thermometer probe were added the Formula II (1.00 g, 0.0025 mol) of Formula III (1.00 mL, 1.00 vol), N,N-dimethyl acetamide (1.20 mL, 1.20 vol) and the mass was heated to 90±5° C. The reaction mass was maintained at 90±5° C. under stirring for 1 to 2 h. (R)-1,2-Butanediol (10.00 mL, 10.00 vol) was added to the mass and the mass was heated to 115±5° C. The reaction mass was maintained at 115±5° C. under stirring for 1 to 2 h. The mass was cooled to 60±5° C. and maintained at the same temperature for 2 to 3 h. The mass was filtered and suck dried under vacuum for 12-15 h to obtain Dasatinib-(R)-1,2-Butanediol solvate Formula Id as crystalline solid.

Example-7b: Preparation of Crystalline Dasatinib-(S)-1,2-Butanediol Solvate of Formula Ie from Formula II (One-Pot Synthesis)

To a 500 mL glass vessel equipped with a stirrer, condenser and a thermometer probe were added the Formula-II (20.0 g, 0.0508 mol.), Formula-III (20.00 mL, 1.00 vol), N,N-dimethyl acetamide (20.00 mL, 1.00 vol), mass was heated to 80±5° C. and stirred at 80±5° C. for 3-4 h. (S)-1,2-Butanediol (100 mL, 5.00 vol) was added and the mass was heated to 115±5° C. The reaction mass was maintained at 115±5° C. under stirring for 1 to 2 h. The mass was cooled to 60±5° C. and maintained at the same temperature for 1 to 2h. The mass was filtered and the solid was washed with (S)-1,2-Butanediol (20.0 mL, 1.00 vol), suck dried under vacuum for 1-2 h and material was dried at 40° C. under vacuum for 12-15 h to obtain Dasatinib-(S)-1,2-Butanediol solvate Formula Ie as a crystalline solid.

Scheme-8
Preparation of Amorphous Dasatinib from Formula II using crystalline Dasatinib-Butanediol solvate of Formula Ic (or) Id (or) Ie (or) Ig

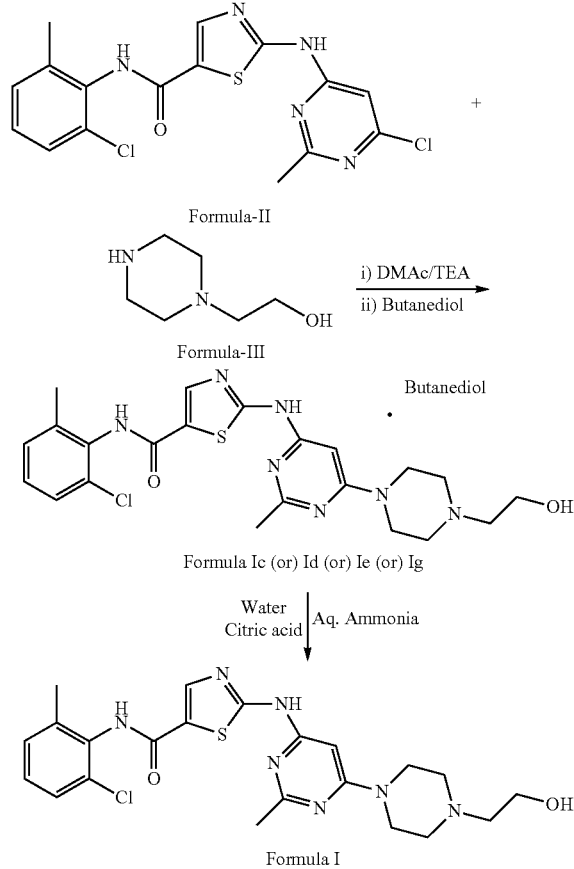

Wherein, Butanediol = (±)-1,2-butanediol or (R)-1,2-butanediol or (S)-1,2-butanediol or (±)-2,3-butanediol
Formula Ic = (±)-1,2-butanediol solvate
Formula Id = (R)-1,2-butanediol solvate
Formula Ie = (S)-1,2-butanediol solvate
Formula Ig = (±)-2,3-butanediol solvate Step-1: Preparation of Crystalline Dasatinib-Butanediol Solvate of Formula Ic or Id or Ie or Ig from Formula II To a glass vessel equipped with a stirrer, condenser and a thermometer probe were added the Formula II, Formula III, N, N-Dimethyl acetamide and Triethylamine at 25±5° C. under stirring. The reaction mass was heated to a suitable temperature. After completion of the reaction, the reaction mass was cooled to and Butanediol was added to the reaction mass under stirring. The mass was heated to a suitable temperature. The mass was cooled and filtered, washed the solid with a suitable solvent and dried to obtain Dasatinib-Butanediol solvate of Formula Ic or Id or Ie or Ig as a crystalline solid.

Step-2: Preparation of Amorphous Dasatinib from Crystalline Dasatinib-1,2-Butanediol solvate of Formula I or Id or Ie or Ig To a 2 L glass vessel equipped with a stirrer, addition funnel and a thermometer probe were added of Formula Ic or Id or Ie or Ig, (obtained by the Example-8, Step-1) Water and Citric acid were added to the reaction mass. The mass was cooled and Aqueous Ammonia was added very slowly into the reaction mass at a constant rate under stirring. The reaction mass was warmed, filtered, the solid was washed with water and dried under vacuum to obtain Amorphous Dasatinib.

Example-5a: Preparation of Amorphous Dasatinib from Formula II Using Crystalline Dasatinib-(±)-1, 2-Butanediol Solvate Formula Ic Step-1: Preparation of Crystalline Dasatinib-(±)-1, 2-Butanediol Solvate of Formula Ic from Formula II To a 1 L glass vessel equipped with a stirrer, condenser and a thermometer probe were added the Formula II (100 g, 0.253 mol), Formula III (100 mL, 1.00 vol), N,N-Dimethyl acetamide (100 mL, 1.00 vol) and Triethylamine (51.33 g, 0.507 mol) was added and the mass was heated to 85±2° C. The reaction mass was maintained at 85±2° C. under stirring. To the mass was (±)-1, 2-Butanediol (500 mL, 5.00 vol) was added and the mass was heated to 120±2° C. The reaction mass was maintained at same temperature under stirring. The mass was cooled to 65*2° C., filtered, the solid was washed with Toluene (500 mL, 5.0 vol) and dried under vacuum to obtain Dasatinib-(±)-1, 2-Butanediol solvate of Formula Ic as a crystalline solid (120 g).

Step-2: Preparation of Amorphous Dasatinib from Crystalline Dasatinib-(±)-1,2-Butanediol Solvate of Formula Ic To a 1 L glass vessel equipped with a stirrer and a thermometer probe were added the Formula Ic (120 g, obtained by the Example-8b, Step-1), Water (1200 mL, 10.0 vol), Citric acid (73.50 g, 0.507 mol) at 25±5° C. The mass was cooled to 10±5° C. under stirring. Aqueous Ammonia was added very slowly into the reaction mass at a constant rate under stirring. The reaction mass was warmed to 25±5° C., the solid material was filtered, washed with water (1000 mL, 10.0 vol) and dried at 55±5° C. under vacuum to obtain to obtain Amorphous Dasatinib as a solid (94.5 g, 76.35% w.r.t. Formula II, 99.8% AUC, N-Oxide impurity: <0.15% AUC, N-Deshydroxyethyl impurity: <0.15% AUC).

Example 9: Preparation of Anhydrous Dasatinib from Formula II

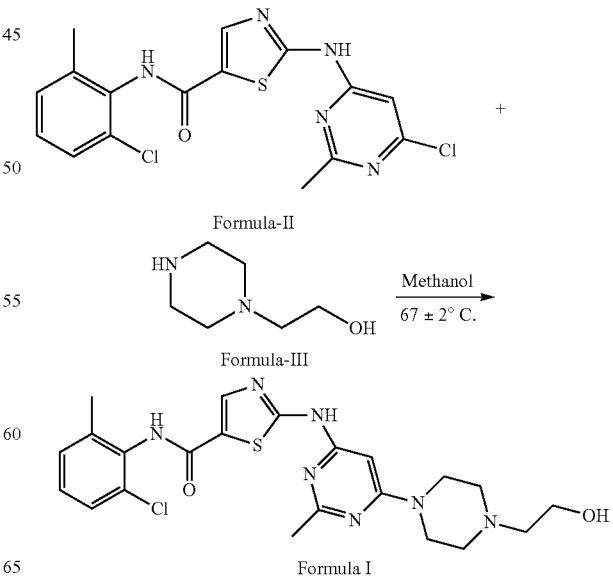

To a 2 L glass vessel equipped with a stirrer, condenser and a thermometer probe were added the Formula II (50.0 g, 0.127 mol), Formula III (200 mL, 4.00 vol) and Methanol (300 mL, 6.00 vol) was added and the mass was heated to 67±2° C. The reaction mass was maintained at 67±2° C. under stirring. Methanol (200 mL, 4.00 vol) and water (100 mL, 2.00 vol) were added. The mass was cooled to 25±5° C. and maintained at the same temperature. The mass was filtered and the solid was washed with methanol (250 mL, 5.00 vol) and dried at 55±5° C. under vacuum to obtain Anhydrous Dasatinib as a crystalline solid (45.0 g, 72.71% w.r.t. Formula II, 99.85% AUC, N-Oxide impurity: <0.15% AUC, N-Deshydroxyethyl impurity: <0.15% AUC)

Example 10: Preparation of Amorphous Dasatinib from Formula II Using Anhydrous Dasatinib

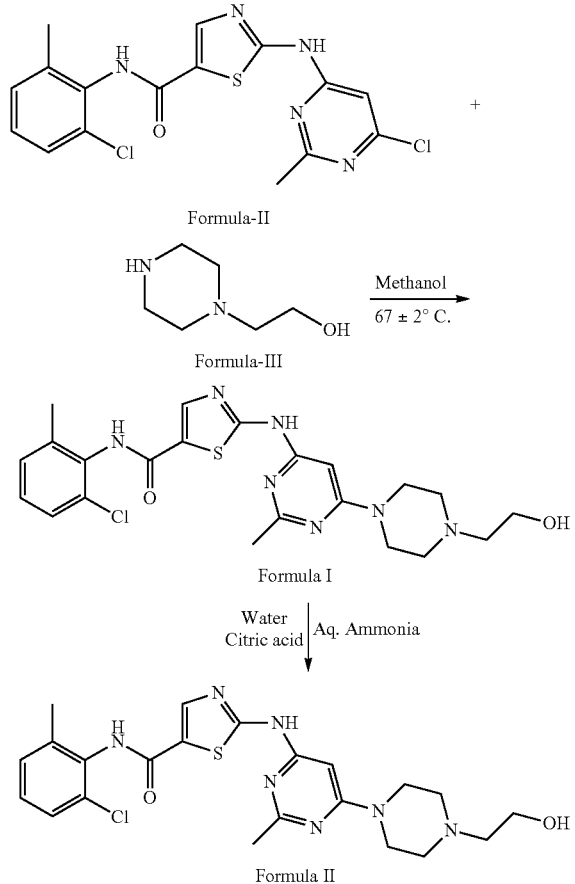

To a 5 L glass vessel equipped with a stirrer and a thermometer probe were added the anhydrous Dasatinib (250 g, 0.512 mol, 1.00 equiv. obtained by using the representative procedure of Example-9), Water (2500 mL, 10.0 vol), Citric acid (590 g, 3.073 mol, 6.00 equiv.) at 25±5° C. The mass neutralised with Aq. Ammonia solution (625 ml, 2.5 vol) at 25±5° C. The solid material was filtered, washed with water (1250 mL, 5.0 vol), suck dried, and dried at 505° C. under vacuum to obtain Amorphous Dasatinib of Formula I as a solid (235 g).

Example-11: Preparation of Dasatinib Monohydrate from Formula II Using Anhydrous Dasatinib

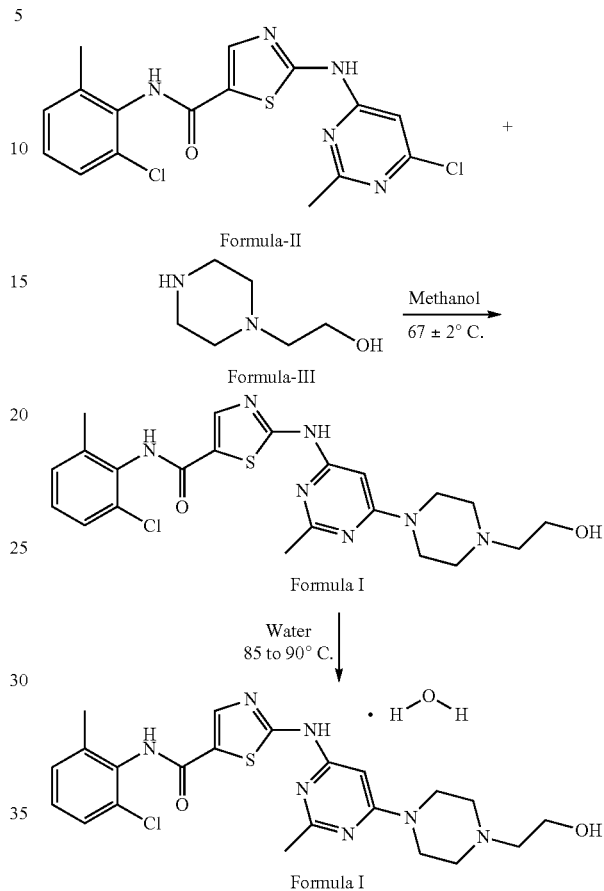

Step-1: Preparation of Anhydrous Dasatinib from Formula II

To a 3 L glass vessel equipped with a stirrer, condenser and a thermometer probe were added the Formula II (150 g, 0.380 mol), Formula III (600 mL, 4.00 vol) and Methanol (900 mL, 6.00 vol) and the mass was heated to 67±2° C. The reaction mass was maintained at 67±2° C. under stirring. Methanol (300 mL, 2.00 vol) and water (300 mL, 2.00 vol) were added into the reaction mass. The reaction mass was cooled to 25±5° C. and maintained at the same temperature. The mass was filtered, the solid was washed with Methanol (750 mL, 5.00 vol) and dried at 55±5° C. under vacuum to obtain Anhydrous Dasatinib as a crystalline solid (142 g, 76.5% wrt Formula II).

Step-2: Preparation of Dasatinib Monohydrate from Anhydrous Dasatinib

To a 500 mL glass vessel equipped with a stirrer, condenser and a thermometer probe were added Anhydrous Dasatinib (40.0 g, obtained by the Example-18, Step-1) and water (400 mL, 10.0 vol). The mass was heated between 85 and 90° C. and maintained at the same temperature under stirring. The mass was cooled to 25±5° C. and maintained at the same temperature. The mass was filtered, the solid was washed with water (200 mL, 5.00 vol) and dried at 55±5° C. under vacuum to obtain Dasatinib Monohydrate as a crystalline solid (38.0 g, 91.62%, 99.92% AUC, N-Oxide impurity: <0.15% AUC, N-Deshydroxyethyl impurity: <0.15% AUC).

The invention claimed is:

1. A dasatinib butanediol solvate.

2. A crystalline dasatinib butanediol solvate, of Formula Ic or Id or Ie or Ig

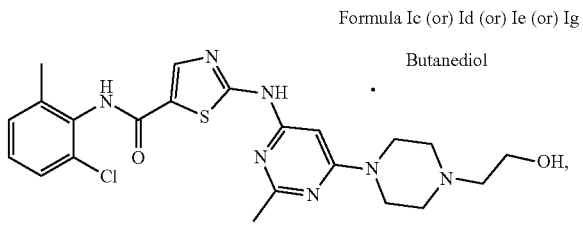 [SMILES: Cc1nc(Nc2ncc(C(=O)Nc3c(C)cccc3Cl)s2)cc(N2CCN(CCO)CC2)n1]

Formula Ic (or) Id (or) Ie (or) Ig · Butanediol wherein Butanediol is selected from (±)-1, 2-Butanediol (Ic) or (R)-1, 2-Butanediol (Id) or (S)-1, 2-Butanediol (Ie) or (±)-2, 3-Butanediol (Ig).

3. The crystalline dasatinib (±)-1,2-Butanediol solvate of Formula Ic of claim 2

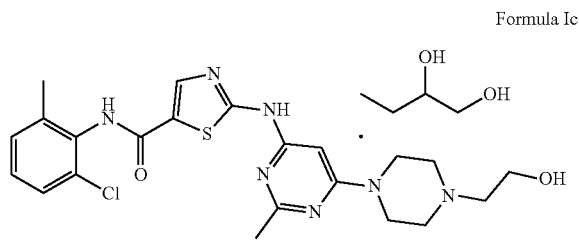

Formula Ic which is characterised by an XPRD pattern comprising peaks at approximately 5.61±0.2, 10.99±0.2, 11.22±0.2, and 24.11±0.2 degrees 2θ.

4. The crystalline dasatinib (±)-1,2-Butanediol solvate of Formula Ic of claim 2

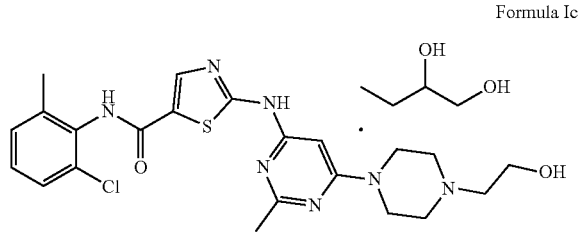

Formula Ic which is characterised by a differential scanning calorimetry thermogram having peaks approximately at 169 and 285° C.

5. The crystalline dasatinib (R)-1,2-Butanediol solvate of Formula Id of claim 2

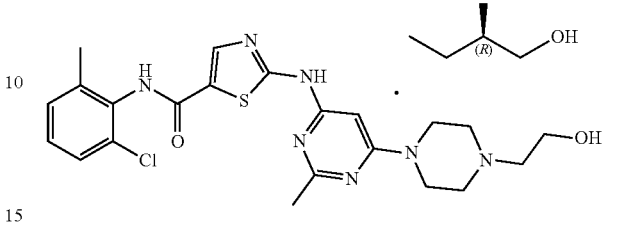

Formula Id which is characterised by an XPRD pattern comprising peaks at approximately 5.69±0.2, 11.30±0.2, 12.62±0.2, and 17.35±0.2 degrees 2θ.

6. The crystalline dasatinib (S)-1,2-Butanediol solvate of Formula Ie of claim 2

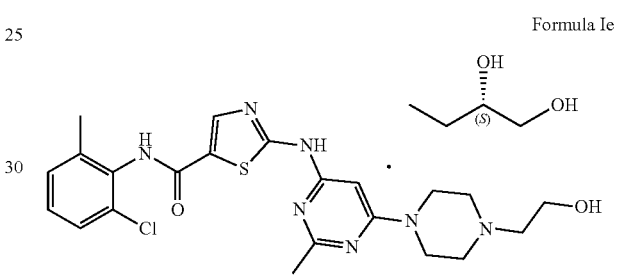

Formula Ie which is characterised by an XPRD pattern comprising peaks at approximately 5.56±0.2, 11.18±0.2, 16.81±0.2, and 17.12±0.2 degrees 2θ.

7. The crystalline dasatinib (±)-2, 3-Butanediol solvate of Formula Ig of claim 2

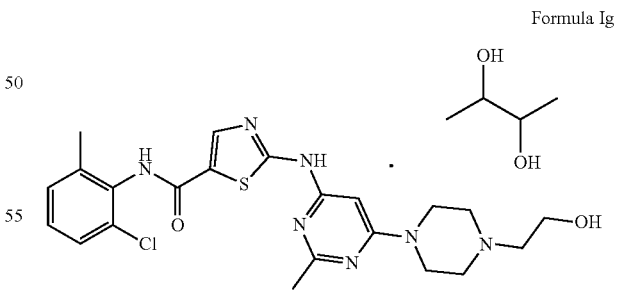

Formula Ig which is characterised by an XPRD pattern comprising peaks at approximately 5.67±0.2, 11.35±0.2, 17.06±0.2, and 17.29±0.2 degrees 2θ.

8. A process for the preparation of crystalline Dasatinib-Butanediol solvate of Formula Ic or Id or Ie or Ig, comprising the following steps, treating the dichloro intermediate of Formula II

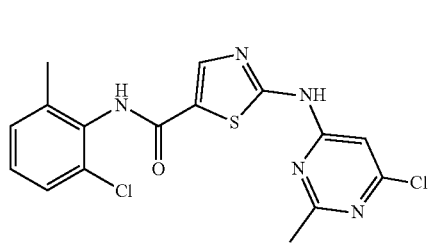

Formula II with 2-(piperazin-1-yl) ethan-1-ol of Formula III

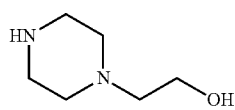

Formula III in the presence of suitable organic solvent and a suitable organic base at a suitable temperature to obtain Formula I (In-situ)

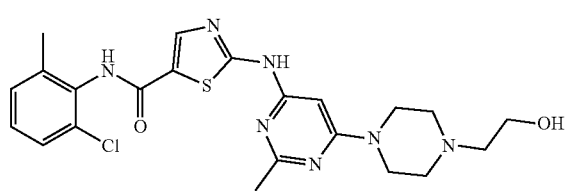 [SMILES: Cc1nc(Nc2ncc(C(=O)Nc3c(C)cccc3Cl)s2)cc(N2CCN(CCO)CC2)n1 ; O]

Formula I treating the mass containing the Formula I with a suitable Butanediol, to obtain crystalline Dasatinib-Butanediol solvate of Formula Ic or Id or Ie or Ig,

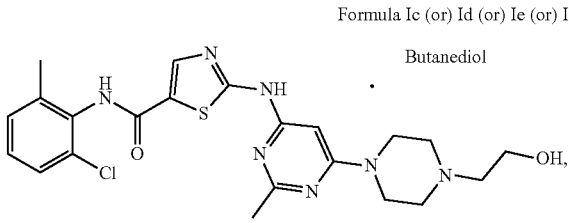

Formula Ic (or) Id (or) Ie (or) Ig
Butanediol wherein
Formula Ic=Dasatinib-(±)-1, 2-Butane diol solvate,
Formula Id=Dasatinib-(R)-1, 2-Butanediol solvate,
Formula Ie=Dasatinib-(S)-1, 2-Butanediol solvate, and
Formula Ig=Dasatinib-(±)-2, 3-Butane diol solvate.

9. The process of claim 8, wherein the suitable organic base is selected from the group consisting of tertiary amines.

10. The process of claim 9, wherein the tertiary amine is N,N-diisopropylethylamine or triethylamine.

11. The process of claim 8, wherein the suitable organic solvent is selected from dimethyl sulfoxide and N,N-dimethyl acetamide.

12. A process for the preparation of amorphous Dasatinib, comprising the following steps, treating the dichloro intermediate of Formula II

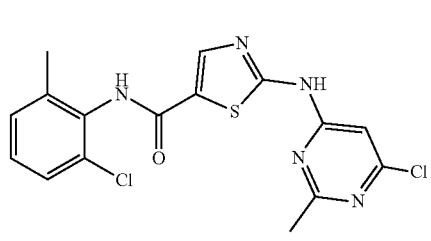

Formula II with 2-(piperazin-1-yl) ethan-1-ol of Formula III

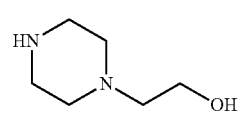

Formula III in the presence of a suitable organic solvent and a suitable organic base to obtain Dasatinib of Formula I (in-situ)

[
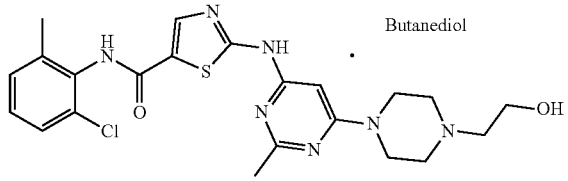
]

Formula I (In-situ)

followed by treating the reaction mass with a suitable Butanediol to obtain a crystalline Dasatinib-Butanediol solvate of Formula Ic or Id or Ie or Ig, Formula Ic (or) Id (or) Ie (or) Ig
Butanediol Formula Ic = Dasatinib-(±) - 1, 2-Butane diol solvate,
Formula Id = Dasatinib-(R) - 1, 2-Butanediol solvate,
Formula Ie = Dasatinib-(S) - 1, 2-Butanediol solvate, and
Formula Ig = Dasatinib-(±) - 2, 3-Butane diol solvate, and treating the crystalline Dasatinib-Butanediol solvate of Formula Ic or Id or Ie or Ig with a citric acid solution followed by treating with an aqueous ammonia solution to obtain amorphous Dasatinib.

13. The process for the preparation of amorphous Dasatinib of claim 12, wherein the suitable organic solvent is selected from the group consisting of sulfoxide and amide solvents.

14. The process for the preparation of amorphous Dasatinib of claim 12, wherein the suitable organic base is selected from the group consisting of tertiary amines.

\* \* \* \* \*